(12) United States Patent
Wu

(10) Patent No.: US 9,110,013 B2
(45) Date of Patent: Aug. 18, 2015

(54) GATED VOLTAMMETRY METHODS

(71) Applicant: Bayer HealthCare LLC, Whippany, NJ (US)

(72) Inventor: Huan-Ping Wu, Granger, IN (US)

(73) Assignee: Bayer HealthCare LLC, Whippany, NJ (US)

( * ) Notice: Subject to any disclaimer, the term of this patent is extended or adjusted under 35 U.S.C. 154(b) by 0 days.

(21) Appl. No.: 14/136,286

(22) Filed: Dec. 20, 2013

(65) Prior Publication Data

US 2014/0151246 A1   Jun. 5, 2014

Related U.S. Application Data

(60) Division of application No. 13/780,589, filed on Feb. 28, 2013, now Pat. No. 8,647,489, which is a division of application No. 12/037,715, filed on Feb. 26, 2008, now Pat. No. 8,404,100, which is a continuation of application No. PCT/US2006/035129, filed on Sep. 11, 2006.

(60) Provisional application No. 60/722,584, filed on Sep. 30, 2005.

(51) Int. Cl.

| G01N 27/327 | (2006.01) |
| G01N 27/413 | (2006.01) |
| A61B 5/145 | (2006.01) |
| A61B 5/1486 | (2006.01) |
| C12Q 1/00 | (2006.01) |
| G01N 33/543 | (2006.01) |

(52) U.S. Cl.
CPC ............ G01N 27/413 (2013.01); A61B 5/1486 (2013.01); A61B 5/14532 (2013.01); C12Q 1/001 (2013.01); G01N 27/3273 (2013.01); G01N 33/5438 (2013.01)

(58) Field of Classification Search
CPC .............. G01N 27/327–27/3274; G01N 27/48
USPC ......... 205/775, 777.5, 778, 792; 435/4–40.52
See application file for complete search history.

(56) References Cited

U.S. PATENT DOCUMENTS

| 3,420,205 A | 1/1969 | Morrison |
| 3,505,136 A | 4/1970 | Attwood |

(Continued)

FOREIGN PATENT DOCUMENTS

| CA | 2423837 | 10/2000 |
| CA | 2358993 | 5/2001 |

(Continued)

OTHER PUBLICATIONS

EPO, "Search Report and Written Opionion for PCT/US2006/035129", Jan. 10, 2007, Publisher: International Searching Authority.

(Continued)

*Primary Examiner* — J. Christopher Ball
(74) *Attorney, Agent, or Firm* — Nixon Peabody LLP

(57) ABSTRACT

A sensor system, device, and methods for determining the concentration of an analyte in a sample is described. Gated voltammetric pulse sequences including multiple duty cycles of sequential excitations and relaxations may provide a shorter analysis time and/or improve the accuracy and/or precision of the analysis. The disclosed pulse sequences may reduce analysis errors arising from the hematocrit effect, variance in cap-gap volumes, non-steady-state conditions, mediator background, a single set of calibration constants, under-fill, and changes in the active ionizing agent content of the sensor strip.

31 Claims, 21 Drawing Sheets

(56) References Cited

U.S. PATENT DOCUMENTS

| | | | |
|---|---|---|---|
| 3,510,268 | A | 5/1970 | Hach |
| 3,551,295 | A | 12/1970 | Dyer |
| 3,562,041 | A | 2/1971 | Robertson |
| 3,573,139 | A | 3/1971 | Eiji Mori et al. |
| 3,621,381 | A | 11/1971 | Eckfeldt |
| 3,715,192 | A | 2/1973 | Wenz et al. |
| 3,720,093 | A | 3/1973 | Gill |
| 3,763,422 | A | 10/1973 | MacPhee et al. |
| 3,770,607 | A | 11/1973 | Williams |
| 3,776,832 | A | 12/1973 | Oswin et al. |
| 3,791,933 | A | 2/1974 | Wenz et al. |
| 3,838,033 | A | 9/1974 | Mindt et al. |
| 3,902,970 | A | 9/1975 | Levin |
| 3,917,453 | A | 11/1975 | Milligan et al. |
| 3,919,627 | A | 11/1975 | Allen |
| 3,925,183 | A | 12/1975 | Oswin et al. |
| 3,937,615 | A | 2/1976 | Clack et al. |
| 3,948,745 | A | 4/1976 | Guillbault et al. |
| 3,980,437 | A | 9/1976 | Kishimoto et al. |
| 4,005,002 | A | 1/1977 | Racine et al. |
| 4,008,448 | A | 2/1977 | Muggli |
| 4,040,908 | A | 8/1977 | Clark, Jr. |
| 4,053,381 | A | 10/1977 | Hamblen et al. |
| 4,065,263 | A | 12/1977 | Woodbridge et al. |
| 4,077,861 | A | 3/1978 | Lauer |
| 4,123,701 | A | 10/1978 | Josefsen et al. |
| 4,127,448 | A | 11/1978 | Schick et al. |
| 4,137,495 | A | 1/1979 | Brown |
| 4,184,936 | A | 1/1980 | Paul et al. |
| 4,214,968 | A | 7/1980 | Battaglia et al. |
| 4,217,196 | A | 8/1980 | Huch |
| 4,224,125 | A | 9/1980 | Nakamura et al. |
| 4,225,410 | A | 9/1980 | Pace et al. |
| 4,229,426 | A | 10/1980 | Haagensen, Jr. |
| 4,230,537 | A | 10/1980 | Delente et al. |
| 4,233,029 | A | 11/1980 | Columbus |
| 4,260,680 | A | 4/1981 | Muramatsu et al. |
| 4,263,343 | A | 4/1981 | Kim |
| 4,265,250 | A | 5/1981 | Parker |
| 4,273,639 | A | 6/1981 | Gottermeier |
| 4,297,184 | A | 10/1981 | Dyer |
| 4,297,569 | A | 10/1981 | Flies |
| 4,301,412 | A | 11/1981 | Hill et al. |
| 4,303,887 | A | 12/1981 | Hill et al. |
| 4,304,853 | A | 12/1981 | Jozefonvicz et al. |
| 4,323,536 | A | 4/1982 | Columbus |
| 4,329,642 | A | 5/1982 | Luthi et al. |
| 4,366,033 | A | 12/1982 | Richter et al. |
| 4,376,689 | A | 3/1983 | Nakamura et al. |
| 4,381,775 | A | 5/1983 | Nose et al. |
| 4,396,464 | A | 8/1983 | Giner et al. |
| 4,402,940 | A | 9/1983 | Nose et al. |
| 4,403,984 | A | 9/1983 | Ash et al. |
| 4,407,290 | A | 10/1983 | Wiber |
| 4,407,959 | A | 10/1983 | Tsuji et al. |
| 4,413,407 | A | 11/1983 | Columbus |
| 4,420,564 | A | 12/1983 | Tsuji et al. |
| 4,431,004 | A | 2/1984 | Bessman et al. |
| 4,436,094 | A | 3/1984 | Cerami |
| 4,440,175 | A | 4/1984 | Wilkins |
| 4,473,457 | A | 9/1984 | Columbus |
| 4,476,149 | A | 10/1984 | Poppe et al. |
| 4,477,314 | A | 10/1984 | Richter et al. |
| 4,477,575 | A | 10/1984 | Vogel et al. |
| 4,490,216 | A | 12/1984 | McConnell |
| 4,499,423 | A | 2/1985 | Matthiessen |
| 4,502,938 | A | 3/1985 | Covington et al. |
| 4,517,291 | A | 5/1985 | Seago |
| 4,545,382 | A | 10/1985 | Higgins et al. |
| 4,547,735 | A | 10/1985 | Kiesewetter et al. |
| 4,552,458 | A | 11/1985 | Lowne |
| 4,561,944 | A | 12/1985 | Sasaki et al. |
| 4,571,292 | A | 2/1986 | Liu et al. |
| 4,578,716 | A | 3/1986 | Van Rijckevorsel et al. |
| 4,579,893 | A | 4/1986 | Wang et al. |
| 4,582,684 | A | 4/1986 | Vogel et al. |
| 4,591,550 | A | 5/1986 | Hafeman et al. |
| 4,628,193 | A | 12/1986 | Blum |
| 4,642,295 | A | 2/1987 | Baker |
| 4,648,665 | A | 3/1987 | Davis et al. |
| 4,652,830 | A | 3/1987 | Brown |
| 4,654,197 | A | 3/1987 | Lilja et al. |
| 4,671,288 | A | 6/1987 | Gough |
| 4,676,653 | A | 6/1987 | Strohmeier et al. |
| 4,679,532 | A | 7/1987 | Luksha |
| 4,680,268 | A | 7/1987 | Clark, Jr. |
| 4,682,602 | A | 7/1987 | Prohaska |
| 4,686,479 | A | 8/1987 | Young et al. |
| 4,703,017 | A | 10/1987 | Campbell et al. |
| 4,703,756 | A | 11/1987 | Gough et al. |
| 4,713,347 | A | 12/1987 | Mitchell et al. |
| 4,714,874 | A | 12/1987 | Morris et al. |
| 4,721,677 | A | 1/1988 | Clark, Jr. |
| 4,731,726 | A | 3/1988 | Allen et al. |
| 4,734,184 | A | 3/1988 | Burleigh et al. |
| 4,745,076 | A | 5/1988 | Muller et al. |
| 4,746,607 | A | 5/1988 | Mura et al. |
| 4,750,496 | A | 6/1988 | Reinhart et al. |
| 4,759,828 | A | 7/1988 | Young et al. |
| 4,795,542 | A | 1/1989 | Ross et al. |
| 4,797,256 | A | 1/1989 | Watlington, IV |
| 4,805,624 | A | 2/1989 | Yao et al. |
| 4,806,311 | A | 2/1989 | Greenquist |
| 4,806,312 | A | 2/1989 | Greenquist |
| 4,810,203 | A | 3/1989 | Komatsu |
| 4,816,224 | A | 3/1989 | Vogel et al. |
| 4,820,399 | A | 4/1989 | Senda et al. |
| 4,820,636 | A | 4/1989 | Hill et al. |
| 4,830,595 | A | 5/1989 | McNeil et al. |
| 4,832,814 | A | 5/1989 | Root |
| 4,834,234 | A | 5/1989 | Sacherer et al. |
| 4,849,330 | A | 7/1989 | Humphries et al. |
| 4,854,153 | A | 8/1989 | Miyagawa et al. |
| 4,865,873 | A | 9/1989 | Cole, Jr. et al. |
| 4,877,580 | A | 10/1989 | Aronowitz et al. |
| 4,894,137 | A | 1/1990 | Takizawa et al. |
| 4,897,162 | A * | 1/1990 | Lewandowski et al. ...... 205/786 |
| 4,919,770 | A | 4/1990 | Preidel et al. |
| 4,927,516 | A | 5/1990 | Yamaqucji et al. |
| 4,929,330 | A | 5/1990 | Osaka et al. |
| 4,929,545 | A | 5/1990 | Freitage |
| 4,935,105 | A | 6/1990 | Churchouse |
| 4,935,106 | A | 6/1990 | Beach, Jr. et al. |
| 4,935,346 | A | 6/1990 | Kugler |
| 4,938,860 | A | 7/1990 | Wogoman |
| 4,940,945 | A | 7/1990 | Littlejohn et al. |
| 4,954,087 | A | 9/1990 | Lauks et al. |
| 4,956,275 | A | 9/1990 | Zuk et al. |
| 4,963,814 | A | 10/1990 | Parks et al. |
| 4,970,145 | A | 11/1990 | Bennetto et al. |
| 4,975,647 | A | 12/1990 | Downer et al. |
| 4,976,724 | A | 12/1990 | Nieto |
| 4,999,582 | A | 3/1991 | Parks et al. |
| 4,999,632 | A | 3/1991 | Parks |
| 5,018,164 | A | 5/1991 | Brewer et al. |
| 5,019,974 | A | 5/1991 | Beckers |
| 5,035,862 | A | 7/1991 | Dietze et al. |
| 5,039,618 | A | 8/1991 | Stone |
| 5,046,618 | A | 9/1991 | Wood |
| 5,049,487 | A | 9/1991 | Phillips et al. |
| 5,057,477 | A | 10/1991 | Paterson et al. |
| 5,059,199 | A | 10/1991 | Okada et al. |
| 5,059,394 | A | 10/1991 | Phillips et al. |
| 5,066,372 | A | 11/1991 | Weetall |
| 5,075,077 | A | 12/1991 | Durley, III et al. |
| 5,096,669 | A | 3/1992 | Lauks et al. |
| 5,108,564 | A | 4/1992 | Szuminsky et al. |
| 5,108,819 | A | 4/1992 | Heller et al. |
| 5,112,455 | A | 5/1992 | Cozzette et al. |
| 5,112,758 | A | 5/1992 | Fellman et al. |
| 5,118,183 | A | 6/1992 | Cargill et al. |
| 5,120,420 | A | 6/1992 | Nankai et al. |
| 5,120,421 | A | 6/1992 | Glass et al. |
| 5,122,244 | A | 6/1992 | Hoenes et al. |

(56) References Cited

U.S. PATENT DOCUMENTS

| | | |
|---|---|---|
| 5,128,015 A | 7/1992 | Szuminsky et al. |
| 5,140,176 A | 8/1992 | Okino |
| 5,141,850 A | 8/1992 | Cole et al. |
| 5,141,868 A | 8/1992 | Shanks et al. |
| 5,143,694 A | 9/1992 | Schafer et al. |
| 5,179,005 A | 1/1993 | Phillips et al. |
| 5,179,288 A | 1/1993 | Miffitt et al. |
| 5,182,707 A | 1/1993 | Cooper et al. |
| 5,187,100 A | 2/1993 | Matzinger et al. |
| 5,192,415 A | 3/1993 | Yosioka et al. |
| 5,202,261 A | 4/1993 | Musho et al. |
| 5,217,594 A | 6/1993 | Henkens et al. |
| 5,220,920 A | 6/1993 | Gharib |
| 5,223,117 A | 6/1993 | Wrighton et al. |
| 5,229,282 A | 7/1993 | Yoshioka et al. |
| 5,232,516 A | 8/1993 | Hed |
| 5,232,667 A | 8/1993 | Hieb et al. |
| 5,232,668 A | 8/1993 | Grante et al. |
| 5,234,813 A | 8/1993 | MeGreehan et al. |
| 5,243,516 A | 9/1993 | White |
| 5,246,858 A | 9/1993 | Arbuckle et al. |
| 5,250,439 A | 10/1993 | Mucho et al. |
| 5,261,411 A | 11/1993 | Hughes et al. |
| 5,262,035 A | 11/1993 | Gregg et al. |
| 5,264,103 A | 11/1993 | Yoshioka et al. |
| 5,266,179 A | 11/1993 | Nanki et al. |
| 5,269,891 A | 12/1993 | Colin |
| 5,279,294 A | 1/1994 | Anderson et al. |
| 5,281,395 A | 1/1994 | Markart et al. |
| 5,282,950 A | 2/1994 | Dietze et al. |
| 5,284,770 A | 2/1994 | Adrain et al. |
| 5,286,362 A | 2/1994 | Hoenes et al. |
| 5,288,387 A | 2/1994 | Ito et al. |
| 5,288,636 A | 2/1994 | Pollmann et al. |
| 5,304,468 A | 4/1994 | Phillips et al. |
| 5,306,623 A | 4/1994 | Kiser et al. |
| 5,311,426 A | 5/1994 | Donohue et al. |
| 5,312,590 A | 5/1994 | Gunasingham |
| 5,320,732 A | 6/1994 | Nankai et al. |
| 5,332,479 A | 7/1994 | Uenoyama et al. |
| 5,334,296 A | 8/1994 | Henkens et al. |
| 5,344,754 A | 9/1994 | Zewing |
| 5,352,351 A | 10/1994 | White et al. |
| 5,353,351 A | 10/1994 | Bartoli et al. |
| 5,354,447 A | 10/1994 | Uenoyama et al. |
| 5,366,609 A | 11/1994 | White et al. |
| 5,368,707 A | 11/1994 | Henkens et al. |
| 5,371,687 A | 12/1994 | Holmes, II et al. |
| 5,376,254 A | 12/1994 | Fisher |
| 5,379,214 A | 1/1995 | Arbuckle et al. |
| 5,384,028 A | 1/1995 | Ito |
| 5,385,846 A | 1/1995 | Kuhn et al. |
| 5,389,215 A | 2/1995 | Horiuchi et al. |
| 5,391,272 A | 2/1995 | O'Daly et al. |
| 5,393,903 A | 2/1995 | Gratzel et al. |
| 5,395,504 A | 3/1995 | Saurer et al. |
| 5,403,462 A | 4/1995 | Lev et al. |
| 5,405,511 A | 4/1995 | White et al. |
| 5,410,059 A | 4/1995 | Fraser et al. |
| 5,410,474 A | 4/1995 | Fox |
| 5,411,647 A | 5/1995 | Johnson et al. |
| 5,413,690 A | 5/1995 | Kost et al. |
| 5,413,764 A | 5/1995 | Haar |
| 5,418,142 A | 5/1995 | Kiser et al. |
| 5,421,189 A | 6/1995 | Dussault |
| 5,424,035 A | 6/1995 | Hones et al. |
| 5,426,032 A | 6/1995 | Phillips et al. |
| 5,427,912 A | 6/1995 | Brown et al. |
| 5,429,735 A | 7/1995 | Johnson et al. |
| 5,437,772 A | 8/1995 | DeCastro et al. |
| 5,437,999 A | 8/1995 | Diebold et al. |
| 5,438,271 A | 8/1995 | White et al. |
| 5,439,826 A | 8/1995 | Kontorovich |
| 5,445,967 A | 8/1995 | Deuter |
| 5,447,837 A | 9/1995 | Urnovitz |
| 5,453,360 A | 9/1995 | Yu |
| 5,468,366 A | 11/1995 | Wegner et al. |
| 5,469,846 A | 11/1995 | Khan |
| 5,470,533 A | 11/1995 | Shindo et al. |
| 5,477,326 A | 12/1995 | Dosmann |
| 5,489,414 A | 2/1996 | Schreiber et al. |
| 5,494,638 A | 2/1996 | Gullick |
| 5,500,350 A | 3/1996 | Baker et al. |
| 5,502,396 A | 3/1996 | Desarzens et al. |
| 5,504,011 A | 4/1996 | Gavin et al. |
| 5,508,171 A | 4/1996 | Walling et al. |
| 5,508,200 A | 4/1996 | Tiffany et al. |
| 5,508,203 A | 4/1996 | Fuller et al. |
| 5,509,410 A | 4/1996 | Hill et al. |
| 5,512,159 A | 4/1996 | Yoshioka et al. |
| 5,515,847 A | 5/1996 | Braig et al. |
| 5,520,786 A | 5/1996 | Bloczynski et al. |
| 5,526,111 A | 6/1996 | Collins et al. |
| 5,526,120 A | 6/1996 | Jina et al. |
| 5,526,808 A | 6/1996 | Kaminsky et al. |
| 5,532,128 A | 7/1996 | Eggers et al. |
| 5,552,116 A | 9/1996 | Yokota et al. |
| 5,554,269 A | 9/1996 | Joseph et al. |
| 5,554,531 A | 9/1996 | Zweig |
| 5,556,789 A | 9/1996 | Goerlach et al. |
| 5,563,031 A | 10/1996 | Yu |
| 5,563,042 A | 10/1996 | Phillips et al. |
| 5,569,591 A | 10/1996 | Kell et al. |
| 5,569,608 A | 10/1996 | Sommer |
| 5,572,159 A | 11/1996 | McFarland |
| 5,575,403 A | 11/1996 | Charlton et al. |
| 5,575,895 A | 11/1996 | Ikeda et al. |
| 5,576,073 A | 11/1996 | Kickelhain |
| 5,580,794 A | 12/1996 | Allen |
| 5,589,045 A | 12/1996 | Hyodo |
| 5,589,326 A | 12/1996 | Deng et al. |
| 5,593,390 A | 1/1997 | Castellano et al. |
| 5,593,739 A | 1/1997 | Kickelhain |
| 5,594,906 A | 1/1997 | Holmes, II et al. |
| 5,597,532 A | 1/1997 | Connolly |
| 5,603,820 A | 2/1997 | Malinski et al. |
| 5,604,110 A | 2/1997 | Baker et al. |
| 5,605,662 A | 2/1997 | Heller et al. |
| 5,605,837 A | 2/1997 | Karimi et al. |
| 5,611,909 A | 3/1997 | Studer |
| 5,620,579 A | 4/1997 | Genshaw et al. |
| 5,620,863 A | 4/1997 | Tomasco et al. |
| 5,620,890 A | 4/1997 | Kamps-Holtzapple et al. |
| 5,628,890 A | 5/1997 | Carter et al. |
| 5,630,986 A | 5/1997 | Charlton et al. |
| 5,635,362 A | 6/1997 | Levine et al. |
| 5,635,364 A | 6/1997 | Clark et al. |
| 5,639,671 A | 6/1997 | Bogart et al. |
| 5,642,734 A | 7/1997 | Ruben et al. |
| 5,644,501 A | 7/1997 | Lin et al. |
| 5,645,798 A | 7/1997 | Schreiber et al. |
| 5,650,061 A | 7/1997 | Kuhr et al. |
| 5,650,062 A | 7/1997 | Ikeda et al. |
| 5,653,863 A | 8/1997 | Genshaw et al. |
| 5,654,178 A | 8/1997 | Fitzpatrick et al. |
| 5,656,502 A | 8/1997 | Mackay et al. |
| 5,658,443 A | 8/1997 | Yamamoto et al. |
| 5,658,802 A | 8/1997 | Hayes et al. |
| 5,660,791 A | 8/1997 | Brenneman et al. |
| 5,665,215 A | 9/1997 | Bussmann et al. |
| 5,670,031 A | 9/1997 | Hintsche et al. |
| 5,682,884 A | 11/1997 | Hill et al. |
| 5,686,659 A | 11/1997 | Neel et al. |
| 5,691,486 A | 11/1997 | Behringer et al. |
| 5,691,633 A | 11/1997 | Liu et al. |
| 5,695,623 A | 12/1997 | Michel et al. |
| 5,698,083 A | 12/1997 | Glass |
| 5,700,695 A | 12/1997 | Yassinzadeh et al. |
| 5,704,354 A | 1/1998 | Preidel et al. |
| 5,708,247 A | 1/1998 | McAleer et al. |
| 5,710,011 A | 1/1998 | Forrow et al. |
| 5,710,622 A | 1/1998 | Neel et al. |
| 5,719,667 A | 2/1998 | Miers |
| 5,720,862 A | 2/1998 | Hamamoto et al. |

(56) References Cited

U.S. PATENT DOCUMENTS

| | | |
|---|---|---|
| 5,723,284 A | 3/1998 | Ye |
| 5,723,345 A | 3/1998 | Yamauchi et al. |
| 5,727,548 A | 3/1998 | Hill et al. |
| 5,728,074 A | 3/1998 | Castellano et al. |
| 5,745,308 A | 4/1998 | Spangenberg et al. |
| 5,748,002 A | 5/1998 | Scott et al. |
| 5,755,954 A | 5/1998 | Ludwig et al. |
| 5,757,666 A | 5/1998 | Schreiber et al. |
| 5,759,364 A | 6/1998 | Charlton et al. |
| 5,759,794 A | 6/1998 | Levine et al. |
| 5,762,770 A | 6/1998 | Pritchard et al. |
| 5,776,710 A | 7/1998 | Levine et al. |
| 5,780,304 A | 7/1998 | Matzinger et al. |
| 5,786,584 A | 7/1998 | Button et al. |
| 5,788,833 A | 8/1998 | Lewis et al. |
| 5,789,255 A | 8/1998 | Yu |
| 5,792,668 A | 8/1998 | Fuller et al. |
| 5,798,031 A | 8/1998 | Charlton et al. |
| 5,801,057 A | 9/1998 | Smart et al. |
| 5,807,375 A | 9/1998 | Gross et al. |
| 5,820,551 A | 10/1998 | Hill et al. |
| 5,820,662 A | 10/1998 | Kubo et al. |
| 5,832,921 A | 11/1998 | Lennert et al. |
| 5,834,217 A | 11/1998 | Levine et al. |
| 5,837,546 A | 11/1998 | Allen et al. |
| 5,843,691 A | 12/1998 | Douglas et al. |
| 5,843,692 A | 12/1998 | Phillips et al. |
| 5,846,794 A | 12/1998 | Delobeau et al. |
| 5,849,174 A | 12/1998 | Sanghera et al. |
| 5,856,195 A | 1/1999 | Charlton et al. |
| 5,863,400 A | 1/1999 | Drummond et al. |
| 5,865,972 A | 2/1999 | Buffle et al. |
| 5,873,990 A | 2/1999 | Wojciechowski et al. |
| 5,874,046 A | 2/1999 | Megerle et al. |
| 5,883,378 A | 3/1999 | Irish et al. |
| 5,885,839 A | 3/1999 | Lingane et al. |
| 5,890,489 A | 4/1999 | Elden |
| 5,904,898 A | 5/1999 | Market |
| 5,911,872 A | 6/1999 | Lewis et al. |
| 5,916,156 A | 6/1999 | Hildenbrand et al. |
| 5,921,925 A | 7/1999 | Cartmell et al. |
| 5,922,530 A | 7/1999 | Yu |
| 5,922,591 A | 7/1999 | Anderson et al. |
| 5,925,021 A | 7/1999 | Castellano et al. |
| RE36,268 E | 8/1999 | Szuminsky et al. |
| 5,942,102 A | 8/1999 | Hodges et al. |
| 5,945,341 A | 8/1999 | Howard, III |
| 5,948,289 A | 9/1999 | Noda et al. |
| 5,958,199 A | 9/1999 | Miyamto et al. |
| 5,965,380 A | 10/1999 | Heller et al. |
| 5,968,760 A | 10/1999 | Phillips et al. |
| 5,971,923 A | 10/1999 | Finger |
| 5,989,917 A | 11/1999 | McAleer et al. |
| 6,001,239 A | 12/1999 | Douglas et al. |
| 6,004,441 A | 12/1999 | Fujiwara et al. |
| 6,004,442 A | 12/1999 | Choulga et al. |
| 6,013,170 A | 1/2000 | Meade |
| 6,042,714 A | 3/2000 | Lin et al. |
| 6,044,285 A | 3/2000 | Chaiken et al. |
| 6,045,567 A | 4/2000 | Taylor et al. |
| 6,054,039 A | 4/2000 | Shieh |
| 6,061,128 A | 5/2000 | Zweig et al. |
| 6,069,011 A | 5/2000 | Riedel |
| 6,071,391 A | 6/2000 | Gotoh et al. |
| 6,087,182 A | 7/2000 | Jeng et al. |
| 6,090,268 A | 7/2000 | Akita et al. |
| 6,091,975 A | 7/2000 | Daddona et al. |
| 6,102,872 A | 8/2000 | Doneen et al. |
| 6,103,033 A | 8/2000 | Say et al. |
| 6,103,509 A | 8/2000 | Sode |
| 6,110,354 A | 8/2000 | Darling et al. |
| 6,120,676 A | 9/2000 | Heller et al. |
| 6,121,009 A | 9/2000 | Heller et al. |
| 6,121,050 A | 9/2000 | Han |
| 6,126,609 A | 10/2000 | Keith et al. |
| 6,128,519 A | 10/2000 | Say |
| 6,129,823 A | 10/2000 | Hughes et al. |
| 6,134,461 A | 10/2000 | Say et al. |
| 6,136,549 A | 10/2000 | Feistel |
| 6,136,610 A | 10/2000 | Polito et al. |
| 6,143,164 A | 11/2000 | Heller et al. |
| 6,143,247 A | 11/2000 | Sheppard, Jr. et al. |
| 6,144,869 A | 11/2000 | Berner et al. |
| 6,150,124 A | 11/2000 | Riedel |
| 6,153,069 A | 11/2000 | Pottgen et al. |
| RE36,991 E | 12/2000 | Yamamoto et al. |
| 6,156,051 A | 12/2000 | Schraga |
| 6,156,173 A | 12/2000 | Gotoh et al. |
| 6,156,673 A | 12/2000 | Hintermaier et al. |
| 6,159,745 A | 12/2000 | Roberts et al. |
| 6,162,611 A | 12/2000 | Heller et al. |
| 6,162,639 A | 12/2000 | Douglas |
| 6,168,563 B1 | 1/2001 | Brown |
| 6,168,957 B1 | 1/2001 | Matzinger et al. |
| 6,170,318 B1 | 1/2001 | Lewis |
| 6,174,420 B1 | 1/2001 | Hodges et al. |
| 6,175,752 B1 | 1/2001 | Say et al. |
| 6,176,988 B1 | 1/2001 | Kessler |
| 6,179,979 B1 | 1/2001 | Hodges et al. |
| 6,180,062 B1 | 1/2001 | Naka et al. |
| 6,193,873 B1 | 2/2001 | Oharra et al. |
| 6,197,040 B1 | 3/2001 | LeVaughn et al. |
| 6,200,773 B1 | 3/2001 | Ouyang et al. |
| 6,201,607 B1 | 3/2001 | Roth et al. |
| 6,203,952 B1 | 3/2001 | O'Brian et al. |
| 6,206,282 B1 | 3/2001 | Hayes, Sr. et al. |
| 6,206,292 B1 | 3/2001 | Roberts et al. |
| 6,207,000 B1 | 3/2001 | Schwobel et al. |
| 6,212,417 B1 | 4/2001 | Ikeda et al. |
| 6,218,571 B1 | 4/2001 | Zhena et al. |
| 6,225,078 B1 | 5/2001 | Ikeda et al. |
| 6,226,081 B1 | 5/2001 | Fantone et al. |
| 6,233,471 B1 | 5/2001 | Berner et al. |
| 6,241,862 B1 | 6/2001 | McAleer et al. |
| 6,246,862 B1 | 6/2001 | Perry et al. |
| 6,246,966 B1 | 6/2001 | Perry |
| 6,251,260 B1 | 6/2001 | Heller et al. |
| 6,259,937 B1 | 7/2001 | Schulman et al. |
| 6,261,519 B1 | 7/2001 | Harding et al. |
| 6,262,749 B1 | 7/2001 | Finger et al. |
| 6,268,162 B1 | 7/2001 | Phillips et al. |
| 6,270,637 B1 | 8/2001 | Crismore et al. |
| 6,271,044 B1 | 8/2001 | Ballerstadt et al. |
| 6,272,364 B1 | 8/2001 | Kurnok |
| 6,275,717 B1 | 8/2001 | Gross et al. |
| 6,277,641 B1 | 8/2001 | Yager |
| 6,281,006 B1 | 8/2001 | Heller et al. |
| 6,284,125 B1 | 9/2001 | Hodges et al. |
| 6,284,550 B1 | 9/2001 | Carroll et al. |
| 6,287,595 B1 | 9/2001 | Loewy et al. |
| 6,294,281 B1 | 9/2001 | Heller |
| 6,294,787 B1 | 9/2001 | Schieferdecker et al. |
| 6,295,506 B1 | 9/2001 | Heinonen et al. |
| 6,299,757 B1 | 10/2001 | Feldman et al. |
| 6,300,142 B1 | 10/2001 | Vadgama et al. |
| 6,300,961 B1 | 10/2001 | Finger et al. |
| 6,309,526 B1 | 10/2001 | Fujiwara et al. |
| 6,315,951 B1 | 11/2001 | Markart |
| 6,316,264 B1 | 11/2001 | Corey et al. |
| 6,326,160 B1 | 12/2001 | Dunn et al. |
| 6,329,161 B1 | 12/2001 | Heller et al. |
| 6,330,464 B1 | 12/2001 | Colvin, Jr. et al. |
| 6,335,203 B1 | 1/2002 | Patel et al. |
| 6,338,790 B1 | 1/2002 | Feldman et al. |
| 6,340,428 B1 | 1/2002 | Ikeada et al. |
| 6,342,364 B1 | 1/2002 | Watanabe et al. |
| 6,344,133 B1 | 2/2002 | Formica et al. |
| 6,349,230 B1 | 2/2002 | Kawanaka et al. |
| 6,358,752 B1 | 3/2002 | Durst et al. |
| 6,377,896 B1 | 4/2002 | Sato et al. |
| 6,379,513 B1 | 4/2002 | Chambers et al. |
| 6,389,891 B1 | 5/2002 | D'Angelico et al. |
| 6,391,558 B1 | 5/2002 | Henkens et al. |
| 6,391,645 B1 | 5/2002 | Huang et al. |

(56) References Cited

U.S. PATENT DOCUMENTS

| | | |
|---|---|---|
| 6,394,952 B1 | 5/2002 | Anderson et al. |
| 6,395,227 B1 | 5/2002 | Kiser et al. |
| 6,399,258 B2 | 6/2002 | O'Brien et al. |
| 6,401,532 B2 | 6/2002 | Lubbers |
| 6,413,398 B1 | 7/2002 | Geoff et al. |
| 6,413,411 B1 | 7/2002 | Pottgen et al. |
| 6,414,213 B2 | 7/2002 | Ohmori et al. |
| 6,414,395 B1 | 7/2002 | Ookuma et al. |
| 6,414,410 B1 | 7/2002 | Nakamura et al. |
| 6,420,128 B1 | 7/2002 | Ouyang et al. |
| 6,444,115 B1 | 9/2002 | Hodges et al. |
| 6,447,657 B1 | 9/2002 | Bhullar et al. |
| 6,454,921 B1 | 9/2002 | Hodges et al. |
| 6,461,496 B1 | 10/2002 | Feldman et al. |
| 6,475,372 B1 | 11/2002 | Ohara et al. |
| 6,484,046 B1 | 11/2002 | Say et al. |
| 6,485,923 B1 | 11/2002 | Yani et al. |
| 6,488,827 B1 | 12/2002 | Shartle |
| 6,489,133 B2 | 12/2002 | Phillips et al. |
| 6,491,803 B1 | 12/2002 | Shen et al. |
| 6,491,870 B2 | 12/2002 | Patel et al. |
| 6,501,976 B1 | 12/2002 | Sohrab |
| 6,503,381 B1 | 1/2003 | Gotoh et al. |
| 6,512,986 B1 | 1/2003 | Harmon |
| 6,514,718 B2 | 2/2003 | Heller et al. |
| 6,521,110 B1 | 2/2003 | Hodges et al. |
| 6,521,182 B1 | 2/2003 | Shartle et al. |
| 6,525,330 B2 | 2/2003 | Paolini et al. |
| 6,525,549 B1 | 2/2003 | Poellmann |
| 6,526,298 B1 | 2/2003 | Khalil et al. |
| 6,531,040 B2 | 3/2003 | Musho et al. |
| 6,531,239 B2 | 3/2003 | Heller |
| 6,531,322 B1 | 3/2003 | Jurik et al. |
| 6,537,498 B1 | 3/2003 | Briglin et al. |
| 6,538,735 B1 | 3/2003 | Duebendorfer et al. |
| 6,540,890 B1 | 4/2003 | Bhullar et al. |
| 6,540,891 B1 | 4/2003 | Stewart et al. |
| 6,541,266 B2 | 4/2003 | Modzelewski et al. |
| 6,544,474 B2 | 4/2003 | Douglas et al. |
| 6,549,796 B2 | 4/2003 | Sohrab |
| 6,551,494 B1 | 4/2003 | Heller et al. |
| 6,555,061 B1 | 4/2003 | Leong et al. |
| 6,558,528 B1 | 5/2003 | Matzinger |
| 6,558,529 B1 | 5/2003 | McVey et al. |
| 6,560,471 B1 | 5/2003 | Heller et al. |
| 6,562,625 B2 | 5/2003 | Modzelewski et al. |
| 6,565,509 B1 | 5/2003 | Say et al. |
| 6,570,390 B2 | 5/2003 | Hirayama et al. |
| 6,571,651 B1 | 6/2003 | Hodges |
| 6,572,822 B2 | 6/2003 | Jurki et al. |
| 6,574,425 B1 | 6/2003 | Weiss et al. |
| 6,576,101 B1 | 6/2003 | Heller et al. |
| 6,576,416 B2 | 6/2003 | Haviland et al. |
| 6,576,461 B2 | 6/2003 | Heller et al. |
| 6,579,690 B1 | 6/2003 | Bonnecaze |
| 6,591,125 B1 | 7/2003 | Buse et al. |
| 6,592,744 B1 | 7/2003 | Hodges et al. |
| 6,592,745 B1 | 7/2003 | Feldmen et al. |
| 6,594,514 B2 | 7/2003 | Berner et al. |
| 6,600,997 B2 | 7/2003 | Deweese et al. |
| 6,605,200 B1 | 8/2003 | Mao et al. |
| 6,605,201 B1 | 8/2003 | Mao et al. |
| 6,607,658 B1 | 8/2003 | Heller et al. |
| 6,616,819 B1 | 9/2003 | Liamos et al. |
| 6,618,934 B1 | 9/2003 | Feldmen et al. |
| 6,623,501 B2 | 9/2003 | Heller et al. |
| 6,627,057 B1 | 9/2003 | Bullar et al. |
| 6,632,349 B1 | 10/2003 | Hodges et al. |
| 6,638,415 B1 | 10/2003 | Hodges et al. |
| 6,638,716 B2 | 10/2003 | Heller et al. |
| 6,645,359 B1 | 11/2003 | Bhullar et al. |
| 6,645,368 B1 | 11/2003 | Beaty et al. |
| 6,654,625 B1 | 11/2003 | Say et al. |
| 6,656,702 B1 | 12/2003 | Yugawa et al. |
| 6,676,816 B2 | 1/2004 | Mao et al. |
| 6,676,995 B2 | 1/2004 | Dick et al. |
| 6,689,265 B2 | 2/2004 | Heller et al. |
| 6,689,411 B2 | 2/2004 | Dick et al. |
| 6,690,836 B2 | 2/2004 | Natarajan et al. |
| 6,699,384 B1 | 3/2004 | Lin et al. |
| 6,749,740 B2 | 6/2004 | Liamos et al. |
| 6,790,341 B1 | 9/2004 | Saba et al. |
| 6,824,669 B1 | 11/2004 | Choong et al. |
| 6,824,670 B2 | 11/2004 | Tokunaga et al. |
| 6,841,052 B2 | 1/2005 | Musho et al. |
| 6,890,421 B2 | 5/2005 | Oharra et al. |
| 6,893,545 B2 | 5/2005 | Gotoh et al. |
| 6,942,518 B2 | 9/2005 | Liamos et al. |
| 7,018,843 B2 | 3/2006 | Heller |
| 7,122,111 B2 | 10/2006 | Tokunaga et al. |
| 7,132,041 B2 | 11/2006 | Deng et al. |
| 7,276,146 B2 | 10/2007 | Wilsey |
| 7,351,323 B2 | 4/2008 | Iketaki et al. |
| 8,088,272 B2 | 1/2012 | Deng |
| 8,101,062 B2 | 1/2012 | Deng |
| 2001/0017269 A1 | 8/2001 | Heller et al. |
| 2002/0004106 A1 | 1/2002 | Leddy et al. |
| 2002/0012821 A1 | 1/2002 | Leddy et al. |
| 2002/0053523 A1 | 5/2002 | Liamos et al. |
| 2002/0079219 A1 | 6/2002 | Zhao et al. |
| 2002/0081588 A1 | 6/2002 | De Lumley-Woodyear et al. |
| 2002/0084196 A1 | 7/2002 | Liamos et al. |
| 2002/0125146 A1 | 9/2002 | Chan et al. |
| 2002/0157967 A1 | 10/2002 | Ling et al. |
| 2002/0180446 A1 | 12/2002 | Kuhr et al. |
| 2003/0064525 A1 | 4/2003 | Liess |
| 2003/0113933 A1 | 6/2003 | Rasmus et al. |
| 2003/0119208 A1 | 6/2003 | Yoon et al. |
| 2003/0136673 A1 | 7/2003 | Pilloud et al. |
| 2003/0146110 A1 | 8/2003 | Karinka et al. |
| 2003/0148169 A1 | 8/2003 | Willmer et al. |
| 2003/0159927 A1 | 8/2003 | Lewis et al. |
| 2003/0175737 A1 | 9/2003 | Schulien et al. |
| 2003/0176183 A1 | 9/2003 | Drucker et al. |
| 2003/0178322 A1 | 9/2003 | Bolon et al. |
| 2003/0199744 A1 | 10/2003 | Buse et al. |
| 2003/0201194 A1 | 10/2003 | Heller et al. |
| 2003/0205465 A1 | 11/2003 | Feng et al. |
| 2003/0209450 A1 | 11/2003 | McVey et al. |
| 2004/0005716 A9 | 1/2004 | Beaty et al. |
| 2004/0026253 A1 | 2/2004 | Leddy et al. |
| 2004/0033165 A1 | 2/2004 | Lewis et al. |
| 2004/0040840 A1 | 3/2004 | Mao et al. |
| 2004/0045821 A1 | 3/2004 | Cui et al. |
| 2004/0054267 A1 | 3/2004 | Feldmen et al. |
| 2004/0055898 A1 | 3/2004 | Heller et al. |
| 2004/0060818 A1 | 4/2004 | Feldmen et al. |
| 2004/0074472 A1 | 4/2004 | Kumar et al. |
| 2004/0079653 A1 | 4/2004 | Karinka et al. |
| 2004/0099531 A1 | 5/2004 | Srinivasan et al. |
| 2004/0118682 A1 | 6/2004 | Murray et al. |
| 2004/0149577 A1 | 8/2004 | Kumar et al. |
| 2004/0157337 A1 | 8/2004 | Burke et al. |
| 2004/0157338 A1 | 8/2004 | Burke et al. |
| 2004/0157339 A1 | 8/2004 | Burke et al. |
| 2004/0224137 A1 | 11/2004 | Rogalska et al. |
| 2004/0225230 A1 | 11/2004 | Liamos et al. |
| 2004/0256248 A1 | 12/2004 | Burke et al. |
| 2004/0259180 A1 | 12/2004 | Burke et al. |
| 2004/0260511 A1 | 12/2004 | Burke et al. |
| 2005/0009126 A1 | 1/2005 | Andrews et al. |
| 2005/0049473 A1 | 3/2005 | Desai et al. |
| 2005/0069892 A1 | 3/2005 | Lyengar et al. |
| 2005/0164322 A1 | 7/2005 | Heller et al. |
| 2005/0176153 A1 | 8/2005 | O'hara et al. |
| 2006/0063218 A1 | 3/2006 | Bartkowiak et al. |
| 2006/0074564 A1 | 4/2006 | Bartkowiak et al. |
| 2006/0085137 A1 | 4/2006 | Bartkowiak et al. |
| 2006/0191787 A1 | 8/2006 | Wang et al. |
| 2007/0074977 A1 | 4/2007 | Guo et al. |
| 2008/0099347 A1 | 5/2008 | Barlag et al. ............ 205/793.5 |
| 2008/0102441 A1 | 5/2008 | Chen et al. |
| 2008/0149480 A1 | 6/2008 | Bell |
| 2009/0026094 A1 | 1/2009 | Deng et al. |

(56) References Cited

U.S. PATENT DOCUMENTS

FOREIGN PATENT DOCUMENTS

| | | |
|---|---|---|
| CN | 1322299 | 10/2000 |
| CN | 1328156 | 12/2001 |
| CN | 1598564 | 10/2004 |
| DE | 229500 | 6/1985 |
| DE | 271179 | 8/1989 |
| DE | 4003194 | 8/1991 |
| DE | 4100727 | 7/1992 |
| DE | 19944318891 | 12/1994 |
| DE | 19824629 | 12/1999 |
| DE | 69915850 | 1/2005 |
| EP | 034049 | 8/1981 |
| EP | 0057110 | 8/1982 |
| EP | 0120715 | 10/1984 |
| EP | 0121385 | 10/1984 |
| EP | 0127958 | 12/1984 |
| EP | 010375 | 12/1985 |
| EP | 0164180 | 12/1985 |
| EP | 0255291 | 2/1986 |
| EP | 0206218 | 12/1986 |
| EP | 0213343 | 3/1987 |
| EP | 0215678 | 3/1987 |
| EP | 0230472 | 8/1987 |
| EP | 0241309 | 10/1987 |
| EP | 0287883 | 10/1988 |
| EP | 0330517 | 2/1989 |
| EP | 0354441 | 2/1990 |
| EP | 0359531 | 3/1990 |
| EP | 0359831 | 3/1990 |
| EP | 0383322 | 8/1990 |
| EP | 0417796 | 3/1991 |
| EP | 0470649 | 2/1992 |
| EP | 0471986 | 2/1992 |
| EP | 0537761 | 4/1993 |
| EP | 0546536 | 6/1993 |
| EP | 0546796 | 6/1993 |
| EP | 0628810 | 12/1994 |
| EP | 0636880 | 2/1995 |
| EP | 0640832 | 3/1995 |
| EP | 0651250 | 5/1995 |
| EP | 0186286 | 7/1996 |
| EP | 0732406 | 9/1996 |
| EP | 0732590 | 9/1996 |
| EP | 0741186 | 11/1996 |
| EP | 0800086 | 10/1997 |
| EP | 0837320 | 4/1998 |
| EP | 0840122 | 5/1998 |
| EP | 0851224 | 7/1998 |
| EP | 0859230 | 8/1998 |
| EP | 0958495 | 8/1998 |
| EP | 0878708 | 11/1998 |
| EP | 0878713 | 11/1998 |
| EP | 0887421 | 12/1998 |
| EP | 0894509 | 2/1999 |
| EP | 1042667 | 7/1999 |
| EP | 0942278 | 9/1999 |
| EP | 0964059 | 12/1999 |
| EP | 1119637 | 8/2001 |
| EP | 1279742 | 1/2003 |
| EP | 1411348 | 4/2004 |
| ES | 2184236 | 1/2003 |
| ES | 2223185 | 2/2005 |
| FR | 2325920 | 9/1976 |
| GB | 2295676 | 6/1996 |
| JP | 62209350 | 9/1987 |
| JP | 3260739 | 11/1991 |
| JP | 09089832 | 4/1997 |
| JP | 11087213 | 3/1999 |
| JP | 02120657 | 5/1999 |
| JP | 028826 | 1/2003 |
| JP | 200361650 | 3/2003 |
| JP | 200403478 | 1/2004 |
| JP | 2004093478 | 3/2004 |
| JP | 2004300328 | 10/2004 |
| JP | 2005147990 | 6/2005 |
| WO | 8101794 | 7/1981 |
| WO | 8203729 | 10/1982 |
| WO | 8300926 | 3/1983 |
| WO | 8600138 | 1/1986 |
| WO | 8602732 | 5/1986 |
| WO | 9005293 | 5/1990 |
| WO | 9005910 | 5/1990 |
| WO | 9201928 | 2/1992 |
| WO | 9207655 | 5/1992 |
| WO | 9215704 | 9/1992 |
| WO | 9215859 | 9/1992 |
| WO | 9215861 | 9/1992 |
| WO | 9215950 | 9/1992 |
| WO | 9219961 | 11/1992 |
| WO | 9222669 | 12/1992 |
| WO | 9309433 | 5/1993 |
| WO | 9321518 | 10/1993 |
| WO | 9325898 | 12/1993 |
| WO | 9403542 | 2/1994 |
| WO | 9412950 | 6/1994 |
| WO | 9416095 | 7/1994 |
| WO | 9423295 | 10/1994 |
| WO | 9428414 | 12/1994 |
| WO | 9429705 | 12/1994 |
| WO | 9503542 | 2/1995 |
| WO | 9507050 | 3/1995 |
| WO | 9522597 | 8/1995 |
| WO | 9604398 | 2/1996 |
| WO | 9607908 | 3/1996 |
| WO | 9613707 | 5/1996 |
| WO | 9614026 | 5/1996 |
| WO | 9615454 | 5/1996 |
| WO | 9633403 | 10/1996 |
| WO | 9700441 | 1/1997 |
| WO | 9702487 | 1/1997 |
| WO | 9708544 | 3/1997 |
| WO | 9716726 | 5/1997 |
| WO | 9718465 | 5/1997 |
| WO | 9729366 | 8/1997 |
| WO | 9729847 | 8/1997 |
| WO | 9730344 | 8/1997 |
| WO | 9739343 | 10/1997 |
| WO | 9742882 | 11/1997 |
| WO | 9742888 | 11/1997 |
| WO | 9745719 | 12/1997 |
| WO | 9805424 | 2/1998 |
| WO | 9819153 | 5/1998 |
| WO | 9819159 | 5/1998 |
| WO | 9829740 | 7/1998 |
| WO | 9844342 | 10/1998 |
| WO | 9858250 | 12/1998 |
| WO | 9922227 | 5/1999 |
| WO | 9922230 | 5/1999 |
| WO | 9945375 | 9/1999 |
| WO | 9967628 | 12/1999 |
| WO | 0016089 | 3/2000 |
| WO | 0020626 | 4/2000 |
| WO | 0020855 | 4/2000 |
| WO | 0029540 | 5/2000 |
| WO | 0057011 | 9/2000 |
| WO | 0077523 | 12/2000 |
| WO | 0103207 | 1/2001 |
| WO | 0133206 | 5/2001 |
| WO | 0133216 | 5/2001 |
| WO | 0156771 | 8/2001 |
| WO | 0157510 | 8/2001 |
| WO | 0157513 | 8/2001 |
| WO | 0165246 | 9/2001 |
| WO | 0167099 | 9/2001 |
| WO | 0201214 | 1/2002 |
| WO | 0231481 | 4/2002 |
| WO | 0231482 | 4/2002 |
| WO | 02077633 | 10/2002 |
| WO | 03001195 | 1/2003 |
| WO | 03069304 | 2/2003 |
| WO | 03066554 | 6/2003 |
| WO | 03087802 | 10/2003 |
| WO | 2004023128 | 3/2004 |

(56) References Cited

FOREIGN PATENT DOCUMENTS

| | | |
|---|---|---|
| WO | 2004046707 | 6/2004 |
| WO | 2004053476 | 6/2004 |
| WO | 2004062801 | 7/2004 |
| WO | 2004113896 | 12/2004 |
| WO | 2004113912 | 12/2004 |
| WO | 2004113913 | 12/2004 |
| WO | 2005001462 | 1/2005 |
| WO | 2005001463 | 1/2005 |
| WO | 2005003748 | 1/2005 |
| WO | 2005008231 | 1/2005 |
| WO | 2005022143 | 3/2005 |
| WO | 2006079797 | 8/2006 |

OTHER PUBLICATIONS

Dalrymple-Alford, P., et al., "Peak Shapes in Semi-differential Electroanalysis", "Anal. Chem.", 1977, pp. 1390-1394, vol. 49, No. 9, Publisher: American Chemical Society, Published in: USA.

Parkes, et al., "Balancing Test Time with accurancy and Percision in blood glucose monitoring How fast is too fast?", Jun. 2003.

Yao, et al., "The Low-Potenetail Approach of Glucose Sensing", 1986, pp. 139-146, vol. BME-33, No. 2.

Yao, et al., "A Thin-Film Glucose Electrode System with Compensation for Drifit", 1989, pp. 742-744, vol. XXXV.

* cited by examiner

GATED VOLTAMMETRY METHODS

REFERENCE TO RELATED APPLICATIONS

This application is a divisional of Ser. No. 13/780,589 entitled "Gated Voltammetry Devices" filed Feb. 28, 2013, which is a divisional of Ser. No. 12/037,715 entitled "Gated Voltammetry" filed Feb. 26, 2008, which is a continuation of PCT/US2006/035129 entitled "Gated Voltammetry" filed Sep. 11, 2006, which was published in English and claimed the benefit of U.S. Provisional Application No. 60/722,584 entitled "Gated Voltammetry" as filed on Sep. 30, 2005, each of which are incorporated herein by reference.

BACKGROUND

The quantitative determination of analytes in biological fluids is useful in the diagnosis and treatment of physiological abnormalities. For example, determining the glucose level in biological fluids, such as blood, is important to diabetic individuals who must frequently check their blood glucose level to regulate their diets and/or medication.

Electrochemical systems have been used for this type of analysis. During the analysis, the analyte undergoes a redox reaction with an enzyme or similar species to generate an electric current that may be measured and correlated with the concentration of the analyte. A substantial benefit may be provided to the user by decreasing the time required for the analysis while supplying the desired accuracy and precision.

One example of an electrochemical sensor system for analyzing analytes in biological fluids includes a measuring device and a sensor strip. The sensor strip includes reagents to react with and transfer electrons from the analyte during the analysis and electrodes to pass the electrons through conductors to the device. The measuring device includes contacts to receive the electrons from the strip and the ability to apply a voltage differential between the contacts. The device may record the current passing through the sensor and translate the current values into a measure of the analyte content of the sample. These sensor systems may analyze a single drop of whole blood (WB), such as from 1-15 microliters (μL) in volume.

Examples of bench-top measuring devices include the BAS 100B Analyzer available from BAS Instruments in West Lafayette, Ind.; the CH Instrument Analyzer available from CH Instruments in Austin, Tex.; the Cypress Electrochemical Workstation available from Cypress Systems in Lawrence, Kans.; and the EG&G Electrochemical Instrument available from Princeton Research Instruments in Princeton, N.J. Examples of portable measuring devices include the Ascensia Breeze® and Elite® meters of Bayer Corporation.

The sensor strip may include a working electrode where the analyte undergoes electrochemical reaction and a counter electrode where the opposite electrochemical reaction occurs, thus allowing current to flow between the electrodes. Thus, if oxidation occurs at the working electrode, reduction occurs at the counter electrode. See, for example, *Fundamentals Of Analytical Chemistry*, 4$^{th}$ *Edition*, D. A. Skoog and D. M. West; Philadelphia: Saunders College Publishing (1982), pp 304-341.

The sensor strip also may include a true reference electrode to provide a non-variant reference potential to the measuring device. While multiple reference electrode materials are known, a mixture of silver (Ag) and silver chloride (AgCl) is typical due to the insolubility of the mixture in the aqueous environment of the analysis solution. A reference electrode also may be used as the counter electrode. A sensor strip using such a combination reference-counter electrode is described in U.S. Pat. No. 5,820,551.

The sensor strip may be formed by printing electrodes on an insulating substrate using multiple techniques, such as those described in U.S. Pat. Nos. 6,531,040; 5,798,031; and 5,120,420. One or more reagent layer may be formed by coating one or more of the electrodes, such as the working and/or counter electrodes. In one aspect, more than one of the electrodes may be coated by the same reagent layer, such as when the working and counter electrodes are coated by the same composition. In another aspect, reagent layers having different compositions may be printed or micro-deposited onto the working and counter electrodes using the method described in a U.S. provisional patent application filed Oct. 24, 2003, Ser. No. 60/513,817. Thus, the reagent layer on the working electrode may contain the enzyme, the mediator, and a binder while the reagent layer on the counter electrode contains a soluble redox species, which could be the same as the mediator or different, and a binder.

The reagent layer may include an ionizing agent for facilitating the oxidation or reduction of the analyte, as well as any mediators or other substances that assist in transferring electrons between the analyte and the conductor. The ionizing agent may be an analyte specific enzyme, such as glucose oxidase or glucose dehydrogenase, to catalyze the oxidation of glucose in a WB sample. The reagent layer also may include a binder that holds the enzyme and mediator together. Table I, below, provides conventional combinations of enzymes and mediators for use with specific analytes.

TABLE I

| Analyte | Enzyme | Mediator |
| --- | --- | --- |
| Glucose | Glucose Oxidase | Ferricyanide |
| Glucose | Glucose Dehydrogenase | Ferricyanide |
| Cholesterol | Cholesterol Oxidase | Ferricyanide |
| Lactate | Lactate Oxidase | Ferricyanide |
| Uric Acid | Uricase | Ferricyanide |
| Alcohol | Alcohol Oxidase | Phenylenediamine |

The binder may include various types and molecular weights of polymers, such as CMC (carboxylmethyl cellulose) and/or PEO (polyethylene oxide). In addition to binding the reagents together, the binder may assist in filtering red blood cells, preventing them from coating the electrode surface.

Examples of conventional electrochemical sensor systems for analyzing analytes in biological fluids include the Precision® biosensors available from Abbott in Abbott Park, Ill.; Accucheck® biosensors available from Roche in Indianapolis, Ind.; and OneTouch Ultra® biosensors available from Lifescan in Milpitas, Calif.

One electrochemical method, which has been used to quantify analytes in biological fluids, is coulometry. For example, Heller et al. described the coulometric method for WB glucose measurements in U.S. Pat. No. 6,120,676. In coulometry, the analyte concentration is quantified by exhaustively oxidizing the analyte within a small volume and integrating the current over the time of oxidation to produce the electrical charge representing the analyte concentration. Thus, coulometry captures the total amount of analyte present within the sensor strip.

An important aspect of coulometry is that towards the end of the integration curve of charge vs. time, the rate at which the current changes with time becomes substantially constant to yield a steady-state condition. This steady-state portion of the coulometric curve forms a relatively flat plateau region, thus allowing determination of the corresponding current. However, the coulometric method requires the complete conversion of the entire volume of analyte to reach the steady-state condition. As a result, this method is time consuming and does not provide the fast results which users of electrochemical devices, such as glucose-monitoring products, demand. Another problem with coulometry is that the small volume of the sensor cell must be controlled in order to provide accurate results, which can be difficult with a mass produced device.

Another electrochemical method which has been used to quantify analytes in biological fluids is amperometry. In amperometry, current is measured during a read pulse as a constant potential (voltage) is applied across the working and counter electrodes of the sensor strip. The measured current is used to quantify the analyte in the sample. Amperometry measures the rate at which the electrochemically active species, such as the analyte, is being oxidized or reduced near the working electrode. Many variations of the amperometric method for biosensors have been described, for example in U.S. Pat. Nos. 5,620,579; 5,653,863; 6,153,069; and 6,413,411.

A disadvantage of conventional amperometric methods is the non-steady-state nature of the current after a potential is applied. The rate of current change with respect to time is very fast initially and becomes slower as the analysis proceeds due to the changing nature of the underlying diffusion process. Until the consumption rate of the reduced mediator at the electrode surface equals the diffusion rate, a steady-state current cannot be obtained. Thus, for conventional amperometry methods, measuring the current during the transient period before a steady-state condition is reached may be associated with more inaccuracy than a measurement taken during a steady-state time period.

The "hematocrit effect" provides an impediment to accurately analyzing the concentration of glucose in WB samples. WB samples contain red blood (RB) cells and plasma. The plasma is mostly water, but contains some proteins and glucose. Hematocrit is the volume of the RB cell constituent in relation to the total volume of the WB sample and is often expressed as a percentage. Whole blood samples generally have hematocrit percentages ranging from 20% to 60%, with ~40% being the average.

In conventional sensor strips, glucose may be oxidized by an enzyme, which then transfers the electron to a mediator. This reduced mediator then travels to the working electrode where it is electrochemically oxidized. The amount of mediator being oxidized may be correlated to the current flowing between the working and counter electrodes of the sensor strip. Quantitatively, the current measured at the working electrode is directly proportional to the diffusion coefficient of the mediator. The hematocrit effect interferes with this process because the RB cells block the diffusion of the mediator to the working electrode. Subsequently, the hematocrit effect influences the amount of current measured at the working electrode without any connection to the amount of glucose in the sample.

WB samples having varying concentrations of RB cells may cause inaccuracies in the measurement because the sensor may not distinguish between a lower mediator concentration and a higher mediator concentration where the RB cells block diffusion to the working electrode. For example, when WB samples containing identical glucose levels, but having hematocrits of 20, 40, and 60%, are analyzed, three different glucose readings will be reported by a conventional sensor system based on one set of calibration constants (slope and intercept, for instance). Even though the glucose concentrations are the same, the system will report that the 20% hematocrit sample contains more glucose than the 60% hematocrit sample due to the RB cells interfering with diffusion of the mediator to the working electrode.

The normal hematocrit range (RBC concentration) for humans is from 20% to 60% and is centered around 40%. Hematocrit bias refers to the difference between the reference glucose concentration obtained with a reference instrument, such as the YSI 2300 STAT PLUS™ available from YSI Inc., Yellow Springs, Ohio, and an experimental glucose reading obtained from a portable sensor system for samples containing differing hematocrit levels. The difference between the reference and experimental readings results from the varying hematocrit levels between specific WB samples.

In addition to the hematocrit effect, measurement inaccuracies also may arise when the measurable species concentration does not correlate with the analyte concentration. For example, when a sensor system determines the concentration of a reduced mediator generated in response to the oxidation of an analyte, any reduced mediator not generated by oxidation of the analyte will lead to the sensor system indicating that more analyte is present in the sample than is correct due to mediator background.

In addition to the hematocrit and mediator background effects, other factors also may lead to inaccuracies in the ability of a conventional electrochemical sensor system to determine the concentration of an analyte in a sample. In one aspect, these inaccuracies may be introduced because the portion of the sensor strip that contains the sample may vary in volume from strip to strip. Inaccuracies also may be introduced when sufficient sample is not provided to completely fill the volume of the cap-gap, a condition referred to as under-fill. In other aspects, inaccuracies may be introduced into the measurement by random "noise" and when the sensor system lacks the ability to accurately determine temperature changes in the sample.

In an attempt to overcome one or more of these disadvantages, conventional sensor systems have attempted multiple techniques, not only with regard to the mechanical design of the sensor strip and reagent selection, but also regarding the manner in which the measuring device applies the electric potential to the strip. For example, conventional methods of reducing the hematocrit effect for amperometric sensors include the use of filters, as disclosed in U.S. Pat. Nos. 5,708,247 and 5,951,836; reversing the polarity of the applied current, as disclosed in WO 01/57510; and by methods that maximize the inherent resistance of the sample, as disclosed in U.S. Pat. No. 5,628,890.

Multiple methods of applying the electric potential to the strip, commonly referred to as pulse methods, sequences, or cycles, have been used to address inaccuracies in the determined analyte concentration. For example, in U.S. Pat. No. 4,897,162 the pulse method includes a continuous application of rising and falling voltage potentials that are commingled to give a triangular-shaped wave. Furthermore, WO 2004/053476 and U.S. Pat. Documents 2003/0178322 and 2003/0113933 describe pulse methods that include the continuous application of rising and falling voltage potentials that also change polarity.

Other conventional methods combine a specific electrode configuration with a pulse sequence adapted to that configuration. For example, U.S. Pat. No. 5,942,102 combines the specific electrode configuration provided by a thin layer cell with a continuous pulse so that the reaction products from the counter electrode arrive at the working electrode. This combination is used to drive the reaction until the current change verses time becomes constant, thus reaching a true steady state condition for the mediator moving between the working and counter electrodes during the potential step. While each of these methods balances various advantages and disadvantages, none are ideal.

As may be seen from the above description, there is an ongoing need for improved electrochemical sensor systems, especially those that may provide increasingly accurate determination of the analyte concentration in less time. The systems, devices, and methods of the present invention overcome at least one of the disadvantages associated with conventional systems.

SUMMARY

A voltammetric method of determining the concentration of an analyte in a sample is provided that includes applying a pulse sequence to the sample and measuring the resulting currents, the pulse sequence includes at least two duty cycles. In addition to the at least two duty cycles, the pulse sequence may include a terminal read pulse and/or an initial time delay and may be applied to a sensor strip including a diffusion barrier layer on a working electrode. The method may include less bias attributable to mediator background than a concentration of the analyte determined from another method or from a voltammetric method lacking the pulse sequence comprising at least two duty cycles. The sample may be a liquid including a biological fluid and the analyte may be glucose.

The duty cycles may include an excitation including a potential varied with time or a potential varied linearly with time, such as a linear, cyclic, acyclic, or a combination of these excitation types. A current value may be recorded during each of the excitations and the pulse sequence may include a terminal read pulse. The duty cycles may include acyclic excitations substantially excluding a reverse oxidation peak or a reverse reduction peak and may reduce the concentration of a mediator in the sample not responsive to the analyte in relation to the method where the duty cycles comprise cyclic excitations. The duty cycles may include acyclic excitations terminating before initiation of a reverse current peak, acyclic excitations substantially excluding forward and reverse oxidation and reduction peaks, or acyclic excitations substantially within a diffusion limited current region of a redox pair.

The method may include the determination of at least one contour profile and may include applying at least one data treatment, such as semi-integral, semi-derivative, or derivative, to the resulting currents. The method also may include determining a plurality of calibration sets from the currents and determining the number of duty cycles from the plurality of calibration sets. Determination of the analyte concentration may include averaging multiple concentration values obtained from the plurality of calibration sets.

The method also may include determining if a sensor strip containing the sample is under-filled with the sample. This determination may include comparing at least one current value to a pre-selected value. The method also may include determining the active ionizing agent content of a sensor strip, a determination that may be made by determining a ratio from forward and reverse scan current values. In one aspect, this ratio was previously correlated to known amounts of the active ionizing agent. In another aspect, a calibration slope may be altered in response to the active ionizing agent content of the sensor strip. In another aspect, the excitation/relaxation time ratio of the duty cycles may be from 0.3 to 0.2.

A handheld analyte measuring device is provided for determining the concentration of an analyte in a sample. The device includes a gated voltammetric measuring device adapted to receive a sensor strip. The gated amperometric measuring device includes at least two device contacts in electrical communication with a display through electrical circuitry. The sensor strip includes at least first and second sensor strip contacts. The first sensor strip contact is in electrical communication with a working electrode and the second sensor strip contact is in electrical communication with a counter electrode through conductors. A first reagent layer is on at least one of the electrodes and includes an oxidoreductase and at least one species of a redox pair. The electrodes may be on the same or on different substrates.

A handheld measuring device adapted to receive a sensor strip is provided for determining the concentration of an analyte in a sample. The device includes contacts, at least one display, and electronic circuitry establishing electrical communication between the contacts and the display. The circuitry includes an electric charger and a processor, where the processor is in electrical communication with a computer readable storage medium. The medium includes computer readable software code, which when executed by the processor, causes the charger to implement a gated voltammetric pulse sequence including at least two duty cycles.

A method of reducing the bias attributable to mediator background in a determined concentration of an analyte in a sample is provided that includes applying a gated voltammetric pulse sequence including at least two duty cycles.

A method of determining the duration of a pulse sequence including at least 2 duty cycles, for determining the concentration of an analyte in a sample is provided that includes determining a plurality of sets of calibration constants determined from currents recorded during the at least 2 duty cycles and determining the duration of the pulse sequence in response to the determined concentration of the analyte in the sample. The pulse sequence may be a gated voltammetric pulse sequence.

A method of signaling a user to add additional sample to a sensor strip is provided that includes determining if the sensor strip is under-filled by comparing at least one current value recorded from a pulse sequence including at least 2 duty cycles to a pre-selected value and signaling the user to add additional sample to the sensor strip if the strip is under-filled. The pulse sequence may be a gated voltammetric pulse sequence. The sensor strip may include two electrodes and the determining may be performed in less than five seconds.

A voltammetric method of determining the concentration of an analyte in a sample is provided that includes applying a pulse sequence to the sample and measuring the resulting currents, the pulse sequence includes at least 2 duty cycles having excitation/relaxation time ratios from 0.3 to 0.2. The method may be more accurate than a concentration of the analyte determined from another method where the excitation/relaxation time ratio of a pulse is greater than 0.3.

An electrochemical method for determining the concentration of an analyte in a sample is provided that includes an improvement including applying a gated voltammetric pulse sequence to the sample including at least two duty cycles.

The following definitions are included to provide a clear and consistent understanding of the specification and claims.

The term "analyte" is defined as one or more substances present in a sample. The analysis determines the presence and/or concentration of the analyte present in the sample.

The term "sample" is defined as a composition that may contain an unknown amount of the analyte. Typically, a sample for electrochemical analysis is in liquid form, and preferably the sample is an aqueous mixture. A sample may be a biological sample, such as blood, urine, or saliva. A sample also may be a derivative of a biological sample, such as an extract, a dilution, a filtrate, or a reconstituted precipitate.

The term "voltammetry" is defined as an analysis method where the concentration of an analyte in a sample is determined by electrochemically measuring the oxidation or reduction rate of the analyte at a varying potential.

The term "system" or "sensor system" is defined as a sensor strip in electrical communication through its conductors with a measuring device, which allows for the quantification of an analyte in a sample.

The term "sensor strip" is defined as a device that contains the sample during the analysis and provides electrical communication between the sample and the measuring device. The portion of the sensor strip that contains the sample is often referred to as the "cap-gap."

The term "conductor" is defined as an electrically conductive substance that remains stationary during an electrochemical analysis.

The term "measuring device" is defined as one or more electronic devices that may apply an electric potential to the conductors of a sensor strip and measure the resulting current. The measuring device also may include the processing capability to determine the presence and/or concentration of one or more analytes in response to the recorded current values.

The term "accuracy" is defined as how close the amount of analyte measured by a sensor strip corresponds to the true amount of analyte in the sample. In one aspect, accuracy may be expressed in terms of bias.

The term "precision" is defined as how close multiple analyte measurements are for the same sample. In one aspect, precision may be expressed in terms of the spread or variance among multiple measurements.

The term "redox reaction" is defined as a chemical reaction between two species involving the transfer of at least one electron from a first species to a second species. Thus, a redox reaction includes an oxidation and a reduction. The oxidation half-cell of the reaction involves the loss of at least one electron by the first species, while the reduction half-cell involves the addition of at least one electron to the second species. The ionic charge of a species that is oxidized is made more positive by an amount equal to the number of electrons removed. Likewise, the ionic charge of a species that is reduced is made less positive by an amount equal to the number of electrons gained.

The term "mediator" is defined as a substance that may be oxidized or reduced and that may transfer one or more electrons. A mediator is a reagent in an electrochemical analysis and is not the analyte of interest, but provides for the indirect measurement of the analyte. In a simplistic system, the mediator undergoes a redox reaction in response to the oxidation or reduction of the analyte. The oxidized or reduced mediator then undergoes the opposite reaction at the working electrode of the sensor strip and is regenerated to its original oxidation number.

The term "binder" is defined as a material that provides physical support and containment to the reagents while having chemical compatibility with the reagents.

The term "mediator background" is defined as the bias introduced into the measured analyte concentration attributable to measurable species not responsive to the underlying analyte concentration.

The term "measurable species" is defined as any electrochemically active species that may be oxidized or reduced under an appropriate potential at the working electrode of an electrochemical sensor strip. Examples of measurable species include analytes, oxidoreductases, and mediators.

The term "under-fill" is defined as when insufficient sample was introduced into the sensor strip to obtain an accurate analysis.

The term "redox pair" is defined as two conjugate species of a chemical substance having different oxidation numbers. Reduction of the species having the higher oxidation number produces the species having the lower oxidation number. Alternatively, oxidation of the species having the lower oxidation number produces the species having the higher oxidation number.

The term "oxidation number" is defined as the formal ionic charge of a chemical species, such as an atom. A higher oxidation number, such as (III), is more positive, and a lower oxidation number, such as (II), is less positive.

The term "reversible redox pair" is defined as a pair of redox species where the separation between the forward and reverse scans of the semi-integral is at most 30 mV at the half-height of the $si_{ss}$ transition. For example, in FIG. 10A the forward and reverse semi-integral scans for the ferricyanide/ferrocyanide redox pair in addition to the $si_{ss}$ transition height are shown. At the line where the half-height $si_{ss}$ transition line intersects the forward and reverse scan lines the separation between the lines is 29 mV, establishing the reversibility of the ferricyanide/ferrocyanide redox pair at the depicted scan rate.

The term "quasi-reversible redox pair" is defined as a redox pair where the separation between the forward and reverse scans of the semi-integral is larger than 30 mV at the half-height of the $si_{ss}$ transition for the redox pair.

The term "soluble redox species" is defined as a substance that is capable of undergoing oxidation or reduction and that is soluble in water (pH 7, 25° C.) at a level of at least 1.0 grams per Liter. Soluble redox species include electro-active organic molecules, organotransition metal complexes, and transition metal coordination complexes. The term "soluble redox species" excludes elemental metals and lone metal ions, especially those that are insoluble or sparingly soluble in water.

The term "oxidoreductase" is defined as any enzyme that facilitates the oxidation or reduction of an analyte. An oxidoreductase is a reagent. The term oxidoreductase includes "oxidases," which facilitate oxidation reactions where molecular oxygen is the electron acceptor; "reductases," which facilitate reduction reactions where the analyte is reduced and molecular oxygen is not the analyte; and "dehydrogenases," which facilitate oxidation reactions where molecular oxygen is not the electron acceptor. See, for example, *Oxford Dictionary of Biochemistry and Molecular Biology, Revised Edition*, A. D. Smith, Ed., New York: Oxford University Press (1997) pp. 161, 476, 477, and 560.

The term "electro-active organic molecule" is defined as an organic molecule lacking a metal that is capable of undergoing an oxidation or reduction reaction. Electro-active organic molecules may serve as mediators.

The term "organotransition metal complex," also referred to as "OTM complex," is defined as a complex where a transition metal is bonded to at least one carbon atom through a sigma bond (formal charge of −1 on the carbon atom sigma bonded to the transition metal) or a pi bond (formal charge of 0 on the carbon atoms pi bonded to the transition metal). For example, ferrocene is an OTM complex with two cyclopentadienyl (Cp) rings, each bonded through its five carbon atoms to an iron center by two pi bonds and one sigma bond. Another example of an OTM complex is ferricyanide (III) and its reduced ferrocyanide (II) counterpart, where six cyano ligands (formal charge of −1 on each of the 6 ligands) are sigma bonded to an iron center through the carbon atoms.

The term "coordination complex" is defined as a complex having well-defined coordination geometry, such as octahedral or square planar. Unlike OTM complexes, which are defined by their bonding, coordination complexes are defined by their geometry. Thus, coordination complexes may be OTM complexes (such as the previously mentioned ferricyanide), or complexes where non-metal atoms other than carbon, such as heteroatoms including nitrogen, sulfur, oxygen, and phosphorous, are datively bonded to the transition metal center. For example, ruthenium hexaamine is a coordination complex having a well-defined octahedral geometry where six $NH_3$ ligands (formal charge of 0 on each of the 6 ligands) are datively bonded to the ruthenium center. A more complete discussion of organotransition metal complexes, coordination complexes, and transition metal bonding may be found in Collman et al., *Principles and Applications of Organotransition Metal Chemistry* (1987) and Miessler & Tarr, *Inorganic Chemistry* (1991).

The term "steady-state" is defined as when the change in electrochemical signal (current) with respect to its independent input variable (voltage or time) is substantially constant, such as within ±10 or +5%.

The term "relatively constant" is defined as when the change in a current value or a diffusion rate is within ±20, ±10, or ±5%.

The term "reversing-point" is defined as the point in a cyclic or acyclic scan when the forward scan is stopped and the reverse scan is initiated.

The term "linear excitation" is defined as an excitation where the voltage is varied in a single "forward" direction at a fixed rate, such as from −0.5 V to +0.5 V to provide a 1.0 V excitation range. The excitation range may cover the reduced and oxidized states of a redox pair so that a transition from one state to the other occurs. A linear excitation may be approximated by a series of incremental changes in potential. If the increments occur very close together in time, they correspond to a continuous linear excitation. Thus, applying a change of potential approximating a linear change may be considered a linear excitation.

The term "cyclic excitation" is defined as a combination of a linear forward excitation and a linear reverse excitation where the excitation range includes the oxidation and reduction peaks of a redox pair. For example, varying the potential in a cyclic manner from −0.5 V to +0.5 V and back to −0.5 V is an example of a cyclic excitation for the ferricyanide/ferrocyanide redox pair as used in a glucose sensor, where both the oxidation and reduction peaks are included in the excitation range.

The term "acyclic excitation" is defined in one aspect as an excitation including more of one forward or reverse current peak than the other current peak. For example, an excitation including forward and reverse linear excitations where the forward excitation is started at a different voltage than where the reverse excitation stops, such as from −0.5 V to +0.5 V and back to +0.25 V, is an example of an acyclic excitation. In another example, an acyclic excitation may start and end at substantially the same voltage when the excitation is started at most ±20, ±10, or ±5 mV away from the formal potential $E^{o\prime}$ of the redox pair. In another aspect, an acyclic excitation is defined as an excitation including forward and reverse linear excitations that substantially exclude the oxidation and reduction peaks of a redox pair. For example, the excitation may begin, reverse, and end within the diffusion-limited region of a redox pair, thus excluding the oxidation and reduction peaks of the pair.

The terms "fast excitation," "fast excitation rate," "fast scan," and "fast scan rate" are defined as an excitation where the voltage is changed at a rate of at least 176 mV/sec. Preferable fast excitation rates are rates greater than 200, 500, 1,000, or 2,000 mV/sec.

The terms "slow excitation," "slow excitation rate," "slow scan," and "slow scan rate" are defined as an excitation where the voltage is changed at a rate of at most 175 mV/sec. Preferable slow excitation rates are rates slower than 150, 100, 50, or 10 mV/sec.

The term "average initial thickness" refers to the average height of a layer prior to the introduction of a liquid sample. The term average is used because the top surface of the layer is uneven, having peaks and valleys.

The term "redox intensity" (RI) is defined as the total excitation time divided by the sum of the total excitation time and the total relaxation time delays for a pulse sequence.

The term "handheld device" is defined as a device that may be held in a human hand and is portable. An example of a handheld device is the measuring device accompanying Ascensia® Elite Blood Glucose Monitoring System, available from Bayer HealthCare, LLC, Elkhart, Ind.

The term "on" is defined as "above" and is relative to the orientation being described. For example, if a first element is deposited over at least a portion of a second element, the first element is said to be "deposited on" the second. In another example, if a first element is present above at least a portion of a second element, the first element is said to be "on" the second. The use of the term "on" does not exclude the presence of substances between the upper and lower elements being described. For example, a first element may have a coating over its top surface, yet a second element over at least a portion of the first element and its top coating may be described as "on" the first element. Thus, the use of the term "on" may or may not mean that the two elements being related are in physical contact.

BRIEF DESCRIPTION OF THE DRAWINGS

The invention may be better understood with reference to the following drawings and description. The components in the figures are not necessarily to scale, emphasis instead being placed upon illustrating the principles of the invention. Moreover, in the figures, like referenced numerals designate corresponding parts throughout the different views.

DETAILED DESCRIPTION

An electrochemical analytic system determines the concentration of analytes in a sample, such as the glucose concentration of whole blood. The system includes at least one device that applies gated voltammetric pulse sequences including multiple duty cycles to the sample. Each duty cycle includes a linear, cyclic, or acyclic excitation during which currents (amperage) are measured from a sensor strip while a potential (voltage) applied to the strip is varied linearly with time. Each duty cycle also includes a relaxation that may be provided by an open circuit. The system may compare the resulting current data to determine the concentration of the analyte in the sample, while correcting the results for variations in non-analyte responsive factors. The system also may apply one or more data treatments, including those based on semi-integration, derivatives, and semi-derivatives to analyze the voltammetric data.

The gated voltammetric pulse sequences may provide improved accuracy and precision to the analysis, while reducing the completion time of the analysis. Accuracy errors introduced by the hematocrit effect and precision errors introduced by varying cap-gap volume may be reduced through the combination of a diffusion barrier layer with the gated pulse sequences. Errors otherwise resulting from a non-steady-state sensor condition and/or mediator background also may be reduced. The time required for analysis may be reduced by eliminating the need for additional delays and pulses, such as "incubation" delays to provide reagent rehydration, "burn-off" pulses to renew the electrodes, and mediator regeneration pulses to renew the oxidation state of the mediator. The gated pulse sequences also may allow the determination of dynamic current and contour profiles that provide multiple calibration points, under-fill detection, and the ability to apply temperature compensation to the analysis. Because the gated pulse sequences may generate useful data rapidly, the long wait times of conventional coulometry and the inaccuracy of non-steady-state measurements in conventional amperometry may be avoided.

Figure 1A:
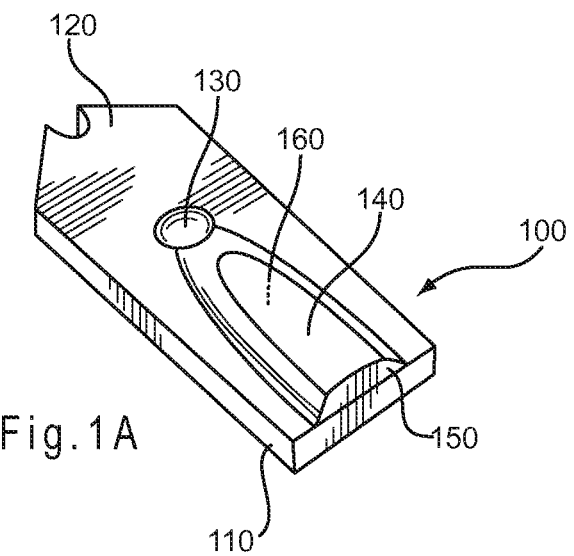
FIG. 1A is a perspective representation of an assembled sensor strip.
Figure 1B:
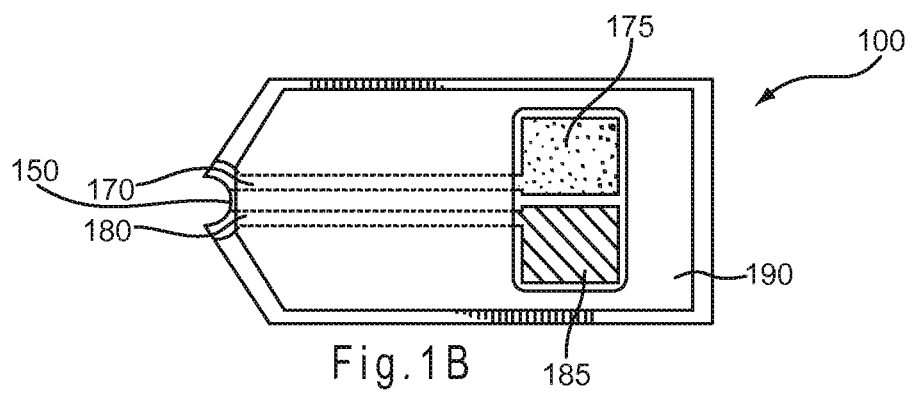
FIG. 1B is a top-view diagram of a sensor strip, with the lid removed.

FIGS. 1A-1B depict a sensor strip 100, which may be used in the present sensor system. FIG. 1A is a perspective representation of an assembled sensor strip 100 including a sensor base 110, at least partially covered by a lid 120 that includes a vent 130, a concave area 140, and an input end opening 150. A partially-enclosed volume 160 (the cap-gap) is formed between the base 110 and the lid 120. Other sensor strip designs compatible with the present invention also may be used, such as those described in U.S. Pat. Nos. 5,120,420 and 5,798,031.

A liquid sample for analysis may be transferred into the cap-gap 160 by introducing the liquid to the opening 150. The liquid fills the cap-gap 160 while expelling the previously contained air through the vent 130. The cap-gap 160 may contain a composition (not shown) that assists in retaining the liquid sample in the cap-gap. Examples of such compositions include water-swellable polymers, such as carboxymethyl cellulose and polyethylene glycol; and porous polymer matrices, such as dextran and polyacrylamide.

FIG. 1B depicts a top-view of the sensor strip 100, with the lid 120 removed. Conductors 170 and 180 may run under a dielectric layer 190 from the opening 150 to a working electrode 175 and a counter electrode 185, respectively. In one aspect, the working and counter electrodes 175, 185 may be in substantially the same plane, as depicted in the figure. In another aspect, the electrodes 175, 185 may be facing, such as described in U.S. Pat. App. 2004/0054267.

While the working and counter electrodes 175, 185 may be closer, in one aspect the electrodes 175, 185 may be separated by greater than 200 or 250 µm. Similarly, while at least one of the electrodes 175, 185 may be closer, in one aspect at least one electrode may be separated from an upper portion of the lid 120 by at least 100 µm. In one aspect, the working and counter electrodes 175, 185 may have surface areas of approximately 1 $mm^2$ and 1.2 $mm^2$, respectively. The dielectric layer 190 may partially cover the electrodes 175, 185 and may be made from any suitable dielectric material, such as an insulating polymer.

The counter electrode 185 balances the potential at the working electrode 175 of the sensor strip 100. In one aspect, this potential may be a reference potential achieved by forming the counter electrode 185 from a redox pair, such as Ag/AgCl, to provide a combined reference-counter electrode. In another aspect, the potential may be provided to the sensor system by forming the counter electrode 185 from an inert material, such as carbon, and including a soluble redox species, such as ferricyanide, within the cap-gap 160.

Alternatively, the sensor strip 100 may be provided with a third conductor and electrode (not shown) to provide a reference potential to the sensor system. This third electrode may be configured as a true reference electrode or as an inert material that relies on a soluble redox species to provide the reference potential. The third electrode also may allow the measuring device to determine the insertion of a sensor strip and/or if the cap-gap 160 has filled with sample. Additional conductors and/or electrodes also may be provided on the strip 100 to provide these and other functions.

Figure 2:
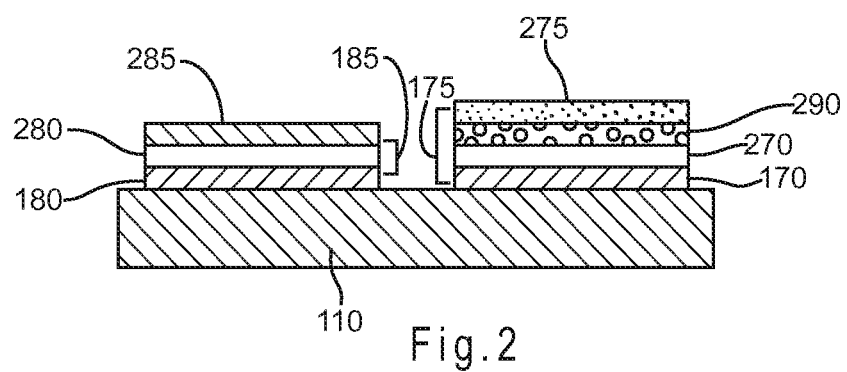
FIG. 2 depicts an end-view diagram of the sensor strip of FIG. 1B.

FIG. 2 depicts an end-view diagram of the sensor strip depicted in FIG. 1B showing the layer structure of the working electrode 175 and the counter electrode 185. The conductors 170 and 180 may lie directly on the base 110. Surface conductor layers 270 and 280 optionally may be deposited on the conductors 170 and 180, respectively. The surface conductor layers 270, 280 may be made from the same or from different materials.

The material or materials used to form the conductors 170, 180 and the surface conductor layers 270, 280 may include any electrical conductor. Preferable electrical conductors are non-ionizing, such that the material does not undergo a net oxidation or a net reduction during analysis of the sample. The conductors 170, 180 preferably include a thin layer of a metal paste or metal, such as gold, silver, platinum, palladium, copper, or tungsten. The surface conductor layers 270, 280 preferably include carbon, gold, platinum, palladium, or combinations thereof. If a surface conductor layer is not present on a conductor, the conductor is preferably made from a non-ionizing material.

The surface conductor material may be deposited on the conductors 170, 180 by any conventional means compatible with the operation of the sensor strip, including foil deposition, chemical vapor deposition, slurry deposition, metallization, and the like. In the case of slurry deposition, the mixture may be applied as an ink to the conductors 170, 180, as described in U.S. Pat. No. 5,798,031.

The reagent layers 275 and 285 may be deposited on the conductors 170 and 180, respectively, and include reagents and optionally a binder. The binder material is preferably a polymeric material that is at least partially water-soluble. Suitable partially water-soluble polymeric materials for use as the binder may include poly(ethylene oxide) (PEO), carboxy methyl cellulose (CMC), polyvinyl alcohol (PVA), hydroxyethylene cellulose (HEC), hydroxypropyl cellulose (HPC), methyl cellulose, ethyl cellulose, ethyl hydroxyethyl cellulose, carboxymethyl ethyl cellulose, polyvinyl pyrrolidone (PVP), polyamino acids such as polylysine, polystyrene sulfonate, gelatin, acrylic acid, methacrylic acid, starch, maleic anhydride, salts thereof, derivatives thereof, and combinations thereof. Among the above binder materials, PEO, PVA, CMC, and PVA are preferred, with CMC and PEO being more preferred at present.

In addition to the binder, the reagent layers 275 and 285 may include the same or different reagents. In one aspect, the reagents present in the first layer 275 may be selected for use with the working electrode 175, while the reagents present in the second layer 285 may be selected for use with the counter electrode 185. For example, the reagents in the layer 285 may facilitate the free flow of electrons between the sample and the conductor 180. Similarly, the reagents in the layer 275 may facilitate the reaction of the analyte.

The reagent layer 275 may include an oxidoreductase specific to the analyte that may facilitate the reaction of the analyte while enhancing the specificity of the sensor system to the analyte, especially in complex biological samples. Examples of some specific oxidoreductases and corresponding analytes are given below in Table II.

TABLE II

| Oxidoreductase (reagent layer) | Analyte |
|---|---|
| Glucose dehydrogenase | β-glucose |
| Glucose oxidase | β-glucose |
| Cholesterol esterase; cholesterol oxidase | Cholesterol |
| Lipoprotein lipase; glycerol kinase; glycerol-3-phosphate oxidase | Triglycerides |
| Lactate oxidase; lactate dehydrogenase; diaphorase | Lactate |
| Pyruvate oxidase | Pyruvate |
| Alcohol oxidase | Alcohol |
| Bilirubin oxidase | Bilirubin |
| Uricase | Uric acid |
| Glutathione reductase | NAD(P)H |
| Carbon monoxide oxidoreductase | Carbon monoxide |

At present, especially preferred oxidoreductases for glucose analysis include glucose oxidase, glucose dehydrogenase, derivatives thereof, or combinations thereof.

The reagent layer 275 also may include a mediator to more effectively communicate the results of the analyte reaction to the surface conductor 270 and/or the conductor 170. Examples of mediators include OTM complexes, coordination complexes, and electro-active organic molecules. Specific examples include ferrocene compounds, ferrocyanide, ferricyanide, coenzymes of substituted or unsubstituted pyrroloquinoline quinones (PQQ), substituted or unsubstituted 3-phenylimino-3H-phenothiazines (PIPT), 3-phenylimino-3H-phenoxazine (PIPO), substituted or unsubstituted benzoquinones, substituted or unsubstituted naphthoquinones, N oxides, nitroso compounds, hydroxylamines, oxines, flavins, phenazines, phenazine derivatives, phenothiazines, indophenols, and indamines. These, and other mediators that may be included in the reagent layer may be found in U.S. Pat. Nos. 5,653,863; 5,520,786; 4,746,607; 3,791,988; and in EP Pat. Nos. 0 354 441 and 0 330 517.

At present, especially preferred mediators for glucose analysis include ferricyanide, ruthenium hexaamine, PIPT, PIPO, or combinations thereof. A review of useful electrochemical mediators for biological redox systems may be found in *Analytica Clinica Acta*. 140 (1982), pages 1-18.

The reagent layers 275, 285 may be deposited by any convenient means, such as printing, liquid deposition, or inkjet deposition. In one aspect, the layers are deposited by printing. With other factors being equal, the angle of the printing blade may inversely affect the thickness of the reagent layers. For example, when the blade is moved at an approximately 82° angle to the base 110, the layer may have a thickness of approximately 10 μm. Similarly, when a blade angle of approximately 62° to the base 110 is used, a thicker 30 μm layer may be produced. Thus, lower blade angles may provide thicker reagent layers. In addition to blade angle, other factors, such as the viscosity of the material being applied as well as the screen-size and emulsion combination, may affect the resulting thickness of the reagent layers 275, 285.

The working electrode 175 also may include a diffusion barrier layer (DBL) that is integral to a reagent layer 275 or that is a distinct layer 290, such as depicted in FIG. 2. Thus, the DBL may be formed as a combination reagent/DBL on the conductor, as a distinct layer on the conductor, or as a distinct layer on the reagent layer. When the working electrode 175 includes the distinct DBL 290, the reagent layer 275 may or may not reside on the DBL 290. Instead of residing on the DBL 290, the reagent layer 275 may reside on any portion of the sensor strip 100 that allows the reagent to solubilize in the sample. For example, the reagent layer 175 may reside on the base 110 or on the lid 120.

The DBL provides a porous space having an internal volume where a measurable species may reside. The pores of the DBL may be selected so that the measurable species may diffuse into the DBL, while physically larger sample constituents, such as RB cells, are substantially excluded. Although conventional sensor strips have used various materials to filter RB cells from the surface of the working electrode, a DBL provides an internal volume to contain and isolate a portion of the measurable species from the sample.

When the reagent layer 275 includes a water-soluble binder, any portion of the binder that does not solubilize into the sample prior to the application of an excitation may function as an integral DBL. The average initial thickness of a combination DBL/reagent layer is preferably less than 30 or 23 micrometers (μm) and more preferably less than 16 μm. At present, an especially preferred average initial thickness of a combination DBL/reagent layer is from 1 to 30 μm or from 3 to 12 μm. The desired average initial thickness of a combination DBL/reagent layer may be selected for a specific excitation length on the basis of when the diffusion rate of the measurable species from the DBL to a conductor surface, such as the surface of the conductor 170 or the surface of the surface conductor 270 from FIG. 2, becomes relatively constant.

Furthermore, using too thick of a DBL with a short excitation length may delay when the diffusion rate of the measurable species from the DBL to the conductor surface becomes relatively constant. For example, when duty cycles including sequential 1 second excitations separated by 0.5 second relaxations are applied to a working electrode using a combination DBL/reagent layer having an average initial thickness of 30 μm, a preferred measurable species diffusion rate from the DBL to the conductor surface may not be reached until at least 6 duty cycles have been applied (>~10 seconds). Conversely, when the same duty cycles are applied to a working electrode using a combination DBL/reagent layer having an average initial thickness of 11 μm, a relatively constant diffusion rate may be reached after the second excitation (~2.5 seconds). Thus, there is an upper limit for the preferred average initial thickness of the DBL for a given duty cycle. A more in-depth treatment of the correlation between DBL thickness, excitation length, and time to reach a relatively constant diffusion rate may be found in WO 2006/042304, filed Oct. 12, 2005, entitled "Concentration Determination in a Diffusion Barrier Layer".

The distinct DBL 290 may include any material that provides the desired pore space, while being partially or slowly soluble in the sample. In one aspect, the distinct DBL 290 may include a reagent binder material lacking reagents. The distinct DBL 290 may have an average initial thickness of at least 1 μm, preferably, from 5 to 25 μm, and more preferably from 8 to 15 μm.

Figure 3A:
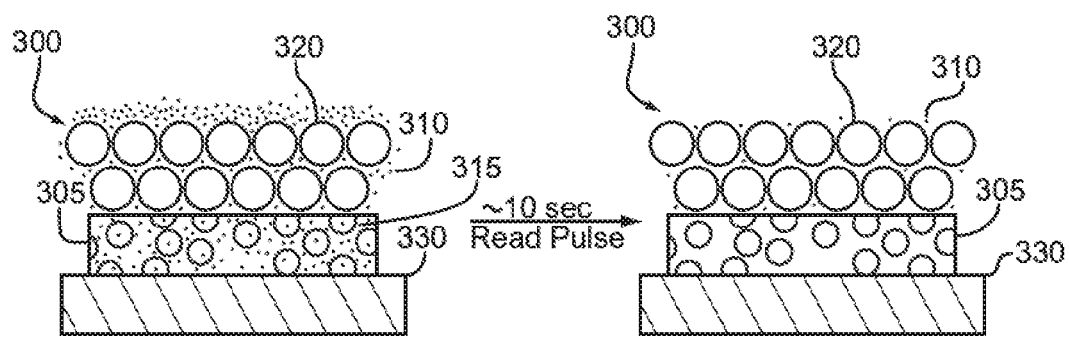
FIGS. 3A and 3B depict a working electrode having a surface conductor and a DBL during the application of long and short read pulses.
Figure 3B:
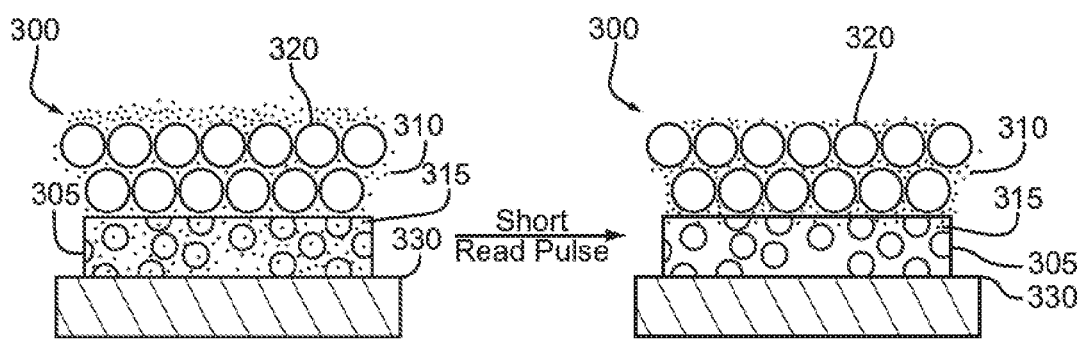

FIGS. 3A and 3B depict a working electrode 300 having a surface conductor 330 and a distinct DBL 305 during the application of long and short read pulses. When a WB sample is applied to the working electrode 300, RB cells 320 cover the DBL 305. Analyte present in the sample forms external measurable species 310 external to the DBL 305. A portion of the external measurable species 310 diffuses into the distinct DBL 305 to give internal measurable species 315.

As shown in FIG. 3A, when a continuous 10 second read pulse is applied to the working electrode 300, both the external and internal measurable species 310 and 315 are excited at the surface conductor 330 by a change in oxidation state. During the long read pulse, the external measurable species 310 diffuses through the sample region where the RB cells 320 reside and through the DBL 305 to the surface conductor 330. Diffusion of the external measurable species 310 through the RB cells 320 during the read pulse introduces the hematocrit effect to the analysis. Because a substantial portion of the measurable species excited at the surface conductor 330 originates from outside the DBL 320, a long read pulse applied to a sensor strip having a DBL may perform similarly with regards to the hematocrit effect to a short read pulse applied to a strip lacking a DBL.

Conversely, FIG. 3B represents the situation where a short excitation is applied to the DBL equipped sensor strip 300 to excite the internal measurable species 315, while substantially excluding from excitation the measurable species 310 external to the DBL 305. During the short excitation, the measurable species 310 either remains external to the DBL 305 or does not substantially diffuse through the DBL to reach the surface conductor 330. In this manner, the short excitation may provide a substantial reduction in the influence of the hematocrit effect on the analysis. By reducing the hematocrit effect, analysis errors (bias) introduced by the sample constituents, including RB cells, may be reduced.

Another advantage of selectively analyzing the measurable species internal to the DBL with a short excitation is a reduction of measurement imprecision from sensor strips having varying cap-gap volumes. Variances in the cap-gap volume between sensor strips may lead to imprecision because the electronics in conventional measuring devices apply the same electric potential and perform the same calculations for each analysis. If a read pulse continues past the time when substantially all of the measurable species present in the cap-gap has been analyzed, the analysis no longer represents the concentration of measurable species in the sample, but instead represents the amount of measurable species in the cap-gap; a very different measurement. Thus, a sensor strip having a larger cap-gap volume will show a higher analyte concentration than a sensor strip having a smaller cap-gap volume, independent of the analyte concentration of the sample. By substantially limiting analysis to the measurable species present in the DBL, the imprecision otherwise introduced by manufacturing variability between sensor strips may be reduced.

Figure 4A:
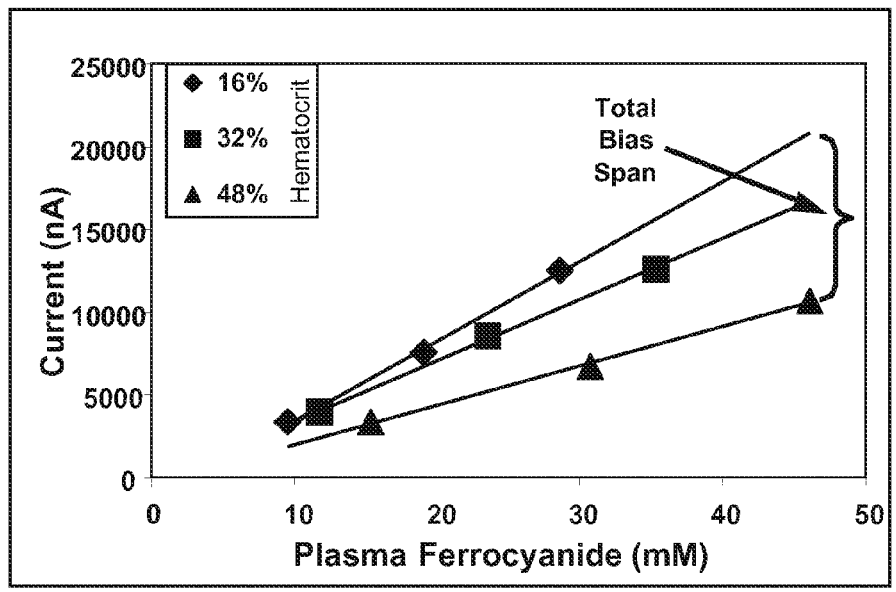
FIGS. 4A and 4B are graphs illustrating the improvement in measurement accuracy when a DBL is combined with a short excitation.
Figure 4B:
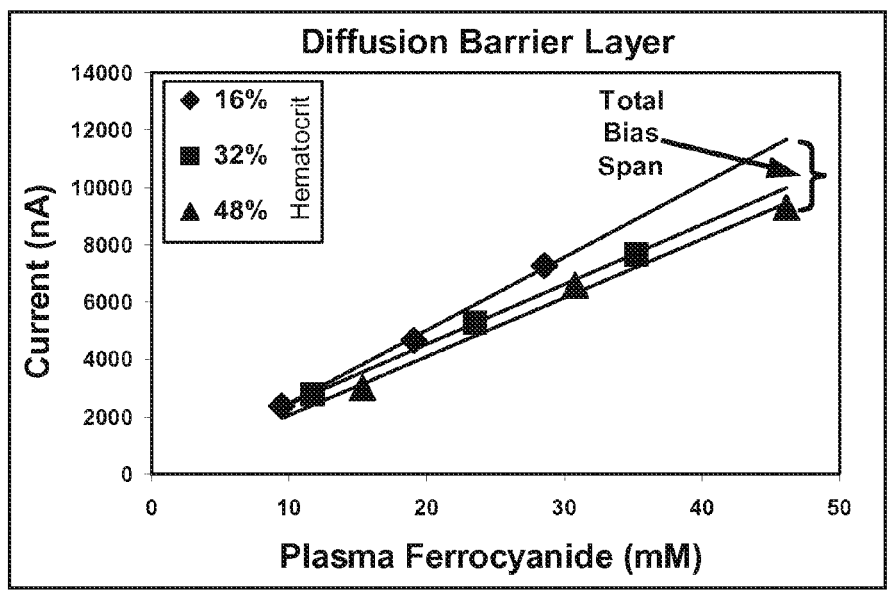

FIGS. 4A and 4B are graphs illustrating the improvement in measurement accuracy when a DBL was combined with a short excitation. FIG. 4A shows a large inaccuracy represented as the difference between the 16% and 48% calibration lines (the total hematocrit bias span) resulting from a sensor strip lacking a DBL after a 1 second excitation. Conversely, FIG. 4B shows a smaller difference between the calibration lines representing a more accurate result when a DBL was combined with a 1 second excitation. The total bias hematocrit span for the DBL combined with a short excitation was nearly two-thirds less than the total bias span without the DBL.

As described above and in further detail in WO 2006/042304, a short read pulse or excitation may provide an improvement in the accuracy and/or precision of an analysis. However, if a single short excitation is used for the analysis, a relatively constant diffusion rate of the measurable species from the DBL to the conductor surface may not be reached during the analysis. This condition also may result in measurement inaccuracy because the concentration of the measurable species within the DBL does not accurately represent that in the sample. Furthermore, the single excitation may not effectively reduce the background signal from the mediator.

Figure 5:
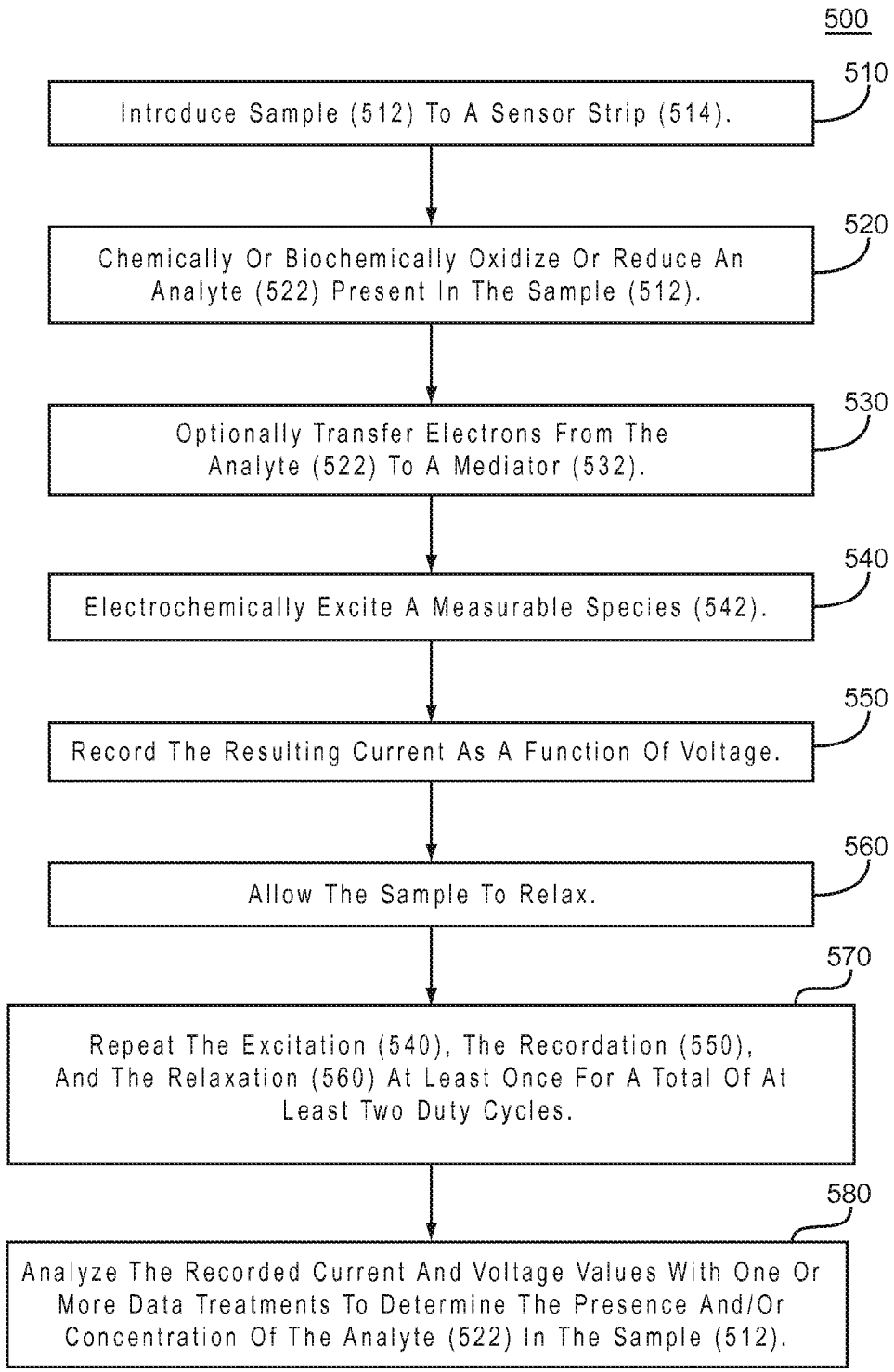
FIG. 5 represents an electrochemical analytic method of determining the presence and concentration of an analyte in a sample.

FIG. 5 represents an electrochemical analysis 500 for determining the presence and optionally the concentration of an analyte 522 in a sample 512 that may overcome the disadvantages associated with short excitations. In one aspect, the analysis 500 may reduce bias from mediator background while providing a shorter analysis time with or without a DBL. In a preferred aspect, the analysis 500 may be completed in less than 3 or less than 1 minute. In a more preferred aspect, the analysis 500 may be completed in from 2 to 50 or from 4 to 32 seconds.

In 510, the sample 512 is introduced to a sensor strip 514, such as the sensor strip depicted in FIGS. 1A-1B and 2. The reagent layers, such as 275 and/or 285 from FIG. 2, begin to solubilize into the sample 512, thus allowing reaction. At this point in the analysis, an initial time delay, or "incubation period," optionally may be provided for the reagents to react with the sample 512. Preferably, the optional time delay may be from 1 to 10 seconds. A more in-depth treatment of initial time delays may be found in U.S. Pat. Nos. 5,620,579 and 5,653,863. In one aspect, the analysis 500 may reduce the need for an incubation period.

During the reaction, a portion of the analyte 522 present in the sample 512 is chemically or biochemically oxidized or reduced in 520, such as by an oxidoreductase. Upon oxidation or reduction, electrons optionally may be transferred between the analyte 522 and a mediator 532 in 530.

In 540, a measurable species 542, which may be the charged analyte 522 from 520 or the charged mediator 532 from 530, is electrochemically excited (oxidized or reduced). For example, when the sample 512 is whole blood containing glucose oxidized by glucose oxidase in 520 and transferring an electron to reduce a ferricyanide (III) mediator to ferrocyanide (II) in 530, the excitation of 540 oxidizes ferrocyanide (II) to ferricyanide (III) at the working electrode. In this manner, an electron is selectively transferred from the glucose analyte to the working electrode of the sensor strip where it may be detected by a measuring device (not shown).

The excitation 540 includes voltammetric scanning where a varying potential or "scan" is applied across the electrodes of the sensor strip 514 at a substantially fixed rate (V/sec). The scan rate may be slow or fast; however, fast scans are preferred due to the nature of the gated pulse sequences. In one aspect, the rate at which the potential is scanned is at least 2 mV/sec, preferably from 20 to 5000 mV/sec, more preferably from 200 to 2000 mV/sec. At present, an especially preferred scan rate is from 500 to 1500 mV/sec.

The duration of the excitation 540 is at most 4 or 5 seconds, and preferably less than 3, 2, 1.5, or 1 second. In another aspect, the duration of the excitation 540 is from 0.1 to 3 seconds, from 0.1 to 2 seconds, or from 0.1 to 1.5 seconds. More preferably, the duration of the excitation 540 is from 0.4 to 1.2 seconds.

In 550, the currents resulting from the scanning excitation 540 may be monitored and recorded as a function of the applied potential (voltage). This contrasts with conventional amperometry and coulometry where a constant voltage is applied while the current is measured as a function of time. In one aspect, the current is monitored and recorded during the excitation 540. In another aspect, the current is not monitored during the relaxation 560 or at least during a portion of the relaxation 560. In another aspect, the current and the potential at the working electrode may be monitored during at least a portion of the relaxation 560, but the values are not used in determining the concentration of the analyte 522.

In 560, the sample undergoes relaxation, where the measuring device may open the circuit through the sensor strip 514, thus allowing the system to relax. During the relaxation 560, the current applied during the excitation 540 is substantially reduced by at least one-half, preferably by an order of magnitude, and more preferably to zero. Preferably, a zero current state is provided by an open circuit. In one aspect, the relaxation 560 is at least 10, 5, 3, 2, 1.5, 1, or 0.5 seconds in duration. In another aspect, the relaxation 560 is from 0.1 to 3 seconds, from 0.1 to 2 seconds, or from 0.1 to 1.5 seconds in duration. More preferably, the relaxation 360 is from 0.2 to 1.5 seconds in duration and provided by an open circuit.

During the relaxation 560, the ionizing agent may react with the analyte to generate additional measurable species without the effects of an electric potential. Thus, for a glucose sensor system including glucose oxidase and a ferricyanide mediator as reagents, additional ferrocyanide (reduced mediator) responsive to the analyte concentration of the sample may be produced without interference from an electric potential during the relaxation 560.

The excitation 540, the recordation 550, and the relaxation 560 constitute a single duty cycle. In 570, the duty cycle is repeated at least once for a total of at least two duty cycles. In one aspect, the duty cycle is repeated at least twice for a total of at least three duty cycles within 180 seconds, 90 seconds, or less. In another aspect, the pulse sequence of the analysis 500 includes at least 4, 6, 8, 10, 14, 18, or 22 duty cycles applied during an independently selected 120, 90, 60, 30, 15, 10, or 5 second time period. In another aspect, the duty cycles are applied during a 5 to 60 second time period. In another aspect, from 3 to 18 or from 3 to 10 duty cycles may be applied within 30 seconds or less. In another aspect, from 4 to 8 duty cycles may be applied within 3 to 16 seconds.

The repetitive "on" and "off" nature of the duty cycles of the analysis 500 directly contrast with conventional methods where voltage is continuously applied to and current is continuously drawn from a sensor strip for from 5 to 10 seconds during the duration of the read pulse. For these conventional methods, the applied voltage may have a fixed potential or may have a potential that is swept from a positive to a negative potential or from a positive or a negative potential to a zero potential relative to a reference potential. Even at a zero relative potential, these methods continuously draw current from the sensor strip during the read pulse, which permits the electrochemical reaction to continue throughout the read pulse. Thus, in these conventional methods the reaction that produces measurable species responsive to the analyte concentration and the diffusion of the measurable species to the working electrode are both affected by current during the zero potential portion of a conventional read pulse. The analysis 500 pulse sequences also are markedly different from conventional methods that use a single long duration pulse with multiple measurements, such as those disclosed in U.S. Pat. No. 5,243,516, due to the multiple relaxations 560.

In 580, the recorded current and voltage values may be transformed with one or more data treatments. The transformed values may be used to determine the presence and/or concentration of the analyte 522 in the sample 512. The transformed values also may be used to determine other characteristics of the analysis 500, including the hematocrit concentration of the sample, multiple calibration sets, under-fill, and the active ionizing agent content of the sensor strip, as outlined below.

FIGS. 6A-6F depict six examples of gated voltammetric pulse sequences that may be used with the method 500. In each pulse sequence, multiple duty cycles were applied to the sensor strip after introduction of the sample. The voltammetric excitation portion of each duty cycle may be applied in a linear (FIG. 6A), cyclic (FIG. 6B), or acyclic manner (FIGS. 6C-6F). In these examples, tilted (linear) or triangular-wave (cyclic or acyclic) excitation pulses were used; however, other wave types compatible with the sensor system and the sample also may be used.

Figure 6A:
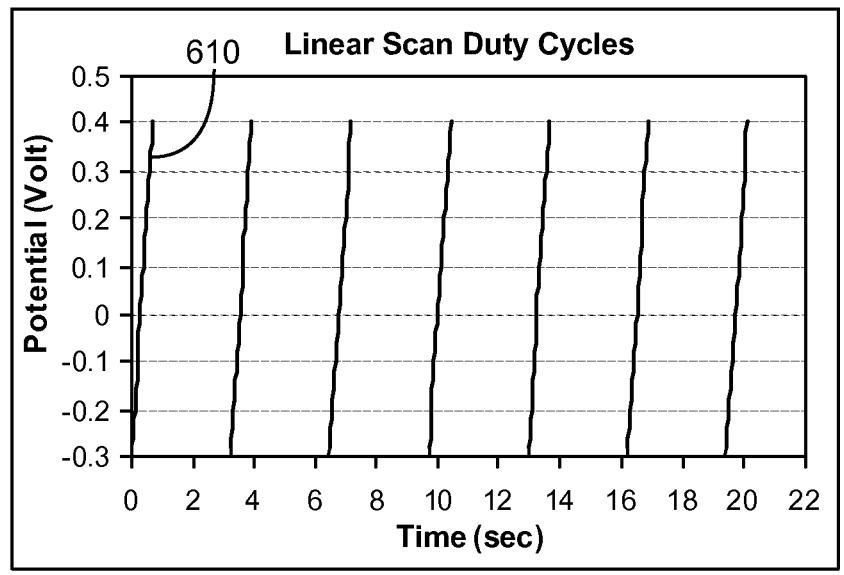
FIGS. 6A-6F represent six examples of pulse sequences where multiple duty cycles were applied to the sensor strip after introduction of the sample.
Figure 6B:
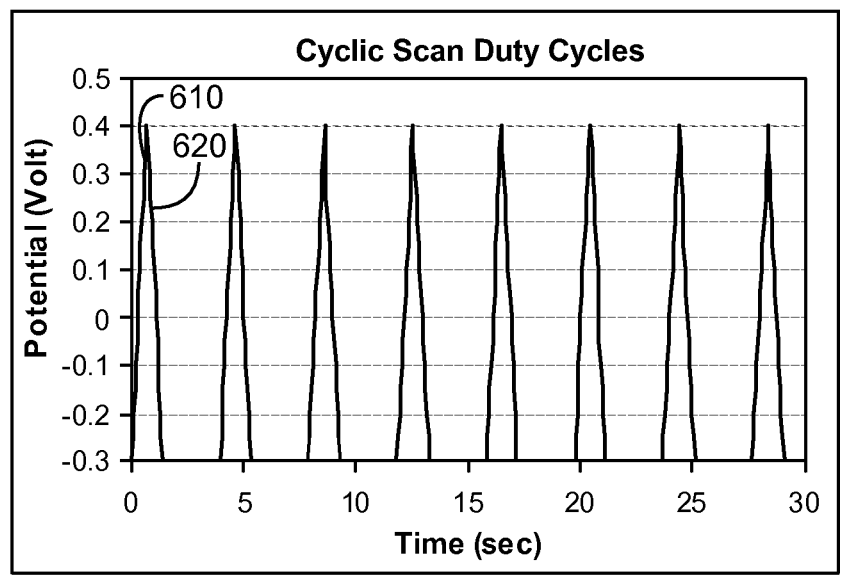
Figure 6C:
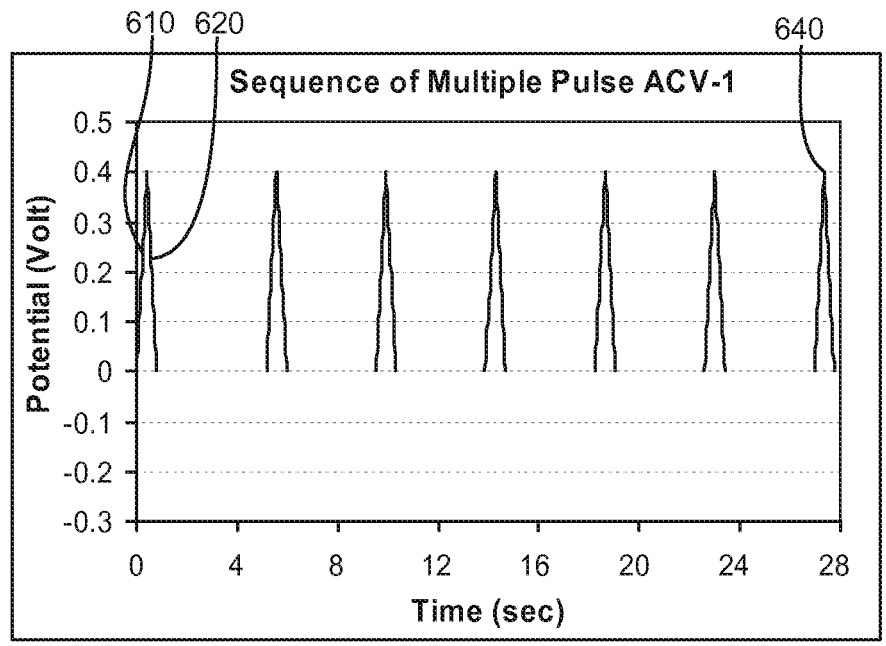
Figure 6D:
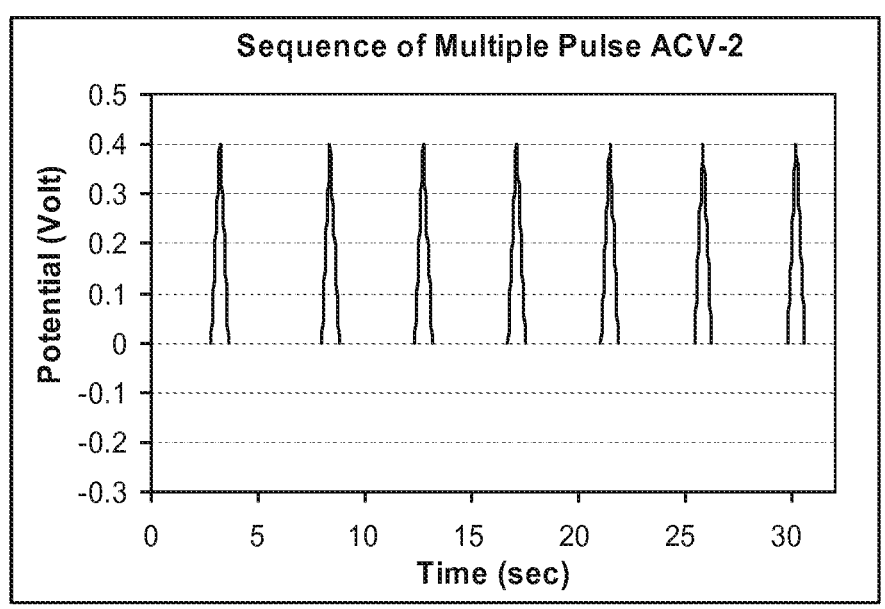
Figure 6E:
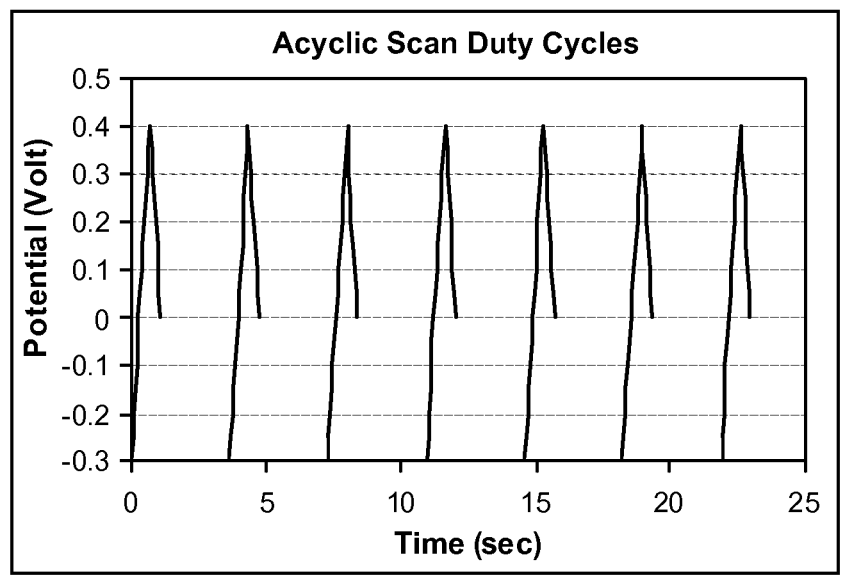
Figure 6F:
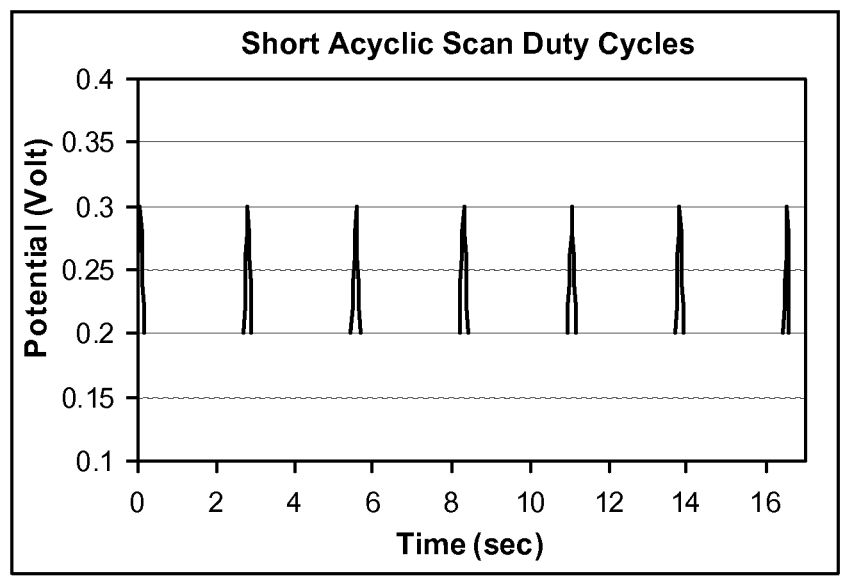

FIG. 6A depicts multiple tilted excitations where the voltage increased linearly with time to an endpoint. FIG. 6B depicts multiple triangular-wave excitations providing cyclic data that includes the complete potential range of the ferricyanide mediator. FIG. 6C depicts six duty cycles including six triangular-wave excitations providing acyclic data that starts and ends at substantially the same voltage. Because the last excitation of FIG. 6C, a terminal read pulse 640, lacks a relaxation, only six duty cycles are shown. FIG. 6D depicts seven duty cycles including seven triangular-wave excitations providing acyclic data. The first duty cycle is preceded by an initial incubation period. FIG. 6E depicts multiple triangular-wave excitations providing acyclic data that starts and ends at different voltages. FIG. 6F depicts multiple triangular-wave excitations resulting in acyclic data that substantially exclude the oxidation and reduction peaks of the ferricyanide/ferrocyanide redox pair.

The terminal read pulse 640 may have the same duration and scan rate as the excitations of the prior duty cycles, as depicted in FIG. 6C, or the terminal read pulse 640 may have a different duration or rate. In one aspect, the terminal read pulse 640 may be of longer duration and increased voltage in relation to the excitations of the prior duty cycles. The increased voltage may provide the ability to detect a species having a higher oxidation potential, such as a control solution. A more complete discussion regarding terminal read pulses may be found in U.S. Provisional App. No. 60/669,729, filed Apr. 8, 2005, entitled "Oxidizable Species as an Internal Reference in Control Solutions for Biosensors."

Control solutions containing known amounts of glucose may be used to verify that the analysis system is operating properly. Specific formulations for control solutions may be found in U.S. Pat. Nos. 3,920,580; 4,572,899; 4,729,959; 5,028,542; 5,605,837; and PCT publications WO 93/21928; WO 95/13535; and WO 95/13536. If the measurement device cannot distinguish between a signal from a control solution versus a sample, control solution readings may be stored as analyte values. Thus, the history of a patient's glucose readings, for example, may be inaccurate regarding diabetic condition.

If the control solutions cannot be identified and their responses separated from those of the blood samples by the test meter, glucose readings of the control solutions will be included in the history of the glucose measurements, which could lead to wrong interpretation of a patient's diabetic condition.

Each of the duty cycles for the pulse sequences depicted in FIGS. 6A-6F provide excitation times of shorter duration than the following open circuit relaxation times; however, this is not required. In FIG. 6C the duration of the excitations is 0.8 seconds at a rate of 1 V/sec while the duration of each relaxation is about 3.2 seconds. Thus, each duty cycle has a duration of about 4 seconds and the pulse sequence lasts for about 24.8 seconds, including a terminal read pulse to provide a redox intensity (RI) of 0.226 (5.6/24.8). The pulse sequence of FIG. 6D provides a lower RI of 0.2 (5.6/28), attributable to the incubation period before the first duty cycle.

The higher the RI for a pulse sequence, the less background inaccuracy introduced into the analysis by the mediator. The pulse sequences represented in FIGS. 6A-6F are oxidative pulses, designed to excite (e.g. oxidize) a reduced mediator, which is the measurable species. Thus, the greater the oxidative current applied to the sensor strip in a given time period, the less chance that mediator reduced by pathways other than oxidation of the analyte contributes to the recorded current values. In combination, the multiple excitations of the gated voltammetric pulse sequence may eliminate the need for an initial pulse to renew the oxidation state of the mediator. For ferricyanide, pulse sequences having RI values of at least 0.01, 0.3, 0.6, or 1 are preferred, with RI values of from 0.1 to 0.8, from 0.2 to 0.7, or from 0.4 to 0.6 being more preferred at present.

During a linear excitation, such as forward excitation 610 depicted in FIG. 6A, the current at the working electrode is measured while the potential at the working electrode changes linearly with time at a constant rate. The excitation range, such as from −0.5 V to +0.5 V, may cover the reduced and oxidized states of a redox pair so that a transition from a first state to a second state occurs. The current measured at the working electrode may be thought of as having three components: the equilibrium current, the diffusion current, and the surface current. The surface current, which may derive from any species adsorbed on the electrode, is generally small. The equilibrium and diffusion currents are the primary components represented in the resulting voltammogram.

A linear voltammogram (a plot of current verses voltage) may be characterized by a plot that starts at an initial current, reaches a peak current, and decays to a lower diffusion-limited current (DLC) level during the excitation. The initial current is substantially dependent on the applied potential, while the DLC is not. If the scan is slow enough, the DLC may be seen as a plateau region in a voltammogram.

The DLC region represents a state where the oxidation or reduction of the measurable species at the conductor surface reaches a maximum rate substantially limited by diffusion. The diffusion may be limited by the rate at which the measurable species travels from the sample to the conductor surface. Alternatively, when the working electrode of the sensor strip includes a DBL, the diffusion may be limited by the rate at which the measurable species travels from the DBL to the conductor surface.

DLC values recorded at a relatively constant diffusion rate after rehydration of the reagent layer may minimize inaccuracies that would otherwise be introduced by variations in the rehydration and diffusion rates of the reagents. Thus, once a relatively constant diffusion rate is reached, the recorded DLC values may more accurately correspond to the concentration of the measurable species, and thus the analyte.

After completion of the forward excitation 610, for a cyclic or acyclic excitation, such as those depicted in FIGS. 6B and 6C, respectively, a reversed potential linear excitation 620 is applied. The reversed potential linear scan of the excitation 620 may be applied at substantially the same rate as the forward scan 610. Thus, the excitation range is scanned from a first lower value to a higher value and back to a second lower value, where the first and second lower values may or may not be the same for cyclic or acyclic scans, respectively. Cyclic, and in some instances acyclic, excitations may examine the transition of a redox species from a reduced state to an oxidized state (and vice versa) in relation to the applied potential or in relation to the diffusion rate of the redox species to the conductor surface.

In relation to a linear excitation, cyclic and acyclic excitations may provide a better representation of the DLC region of the excitation. The advantage of cyclic and acyclic excitations may be especially advantageous for quantifying the DLC from quasi-reversible redox pairs at fast scan rates. Additional information about linear and cyclic scan voltammetry may be found in "Electrochemical Methods: Fundamentals and Applications" by A. J. Bard and L. R. Faulkner, 1980.

Figure 7A:
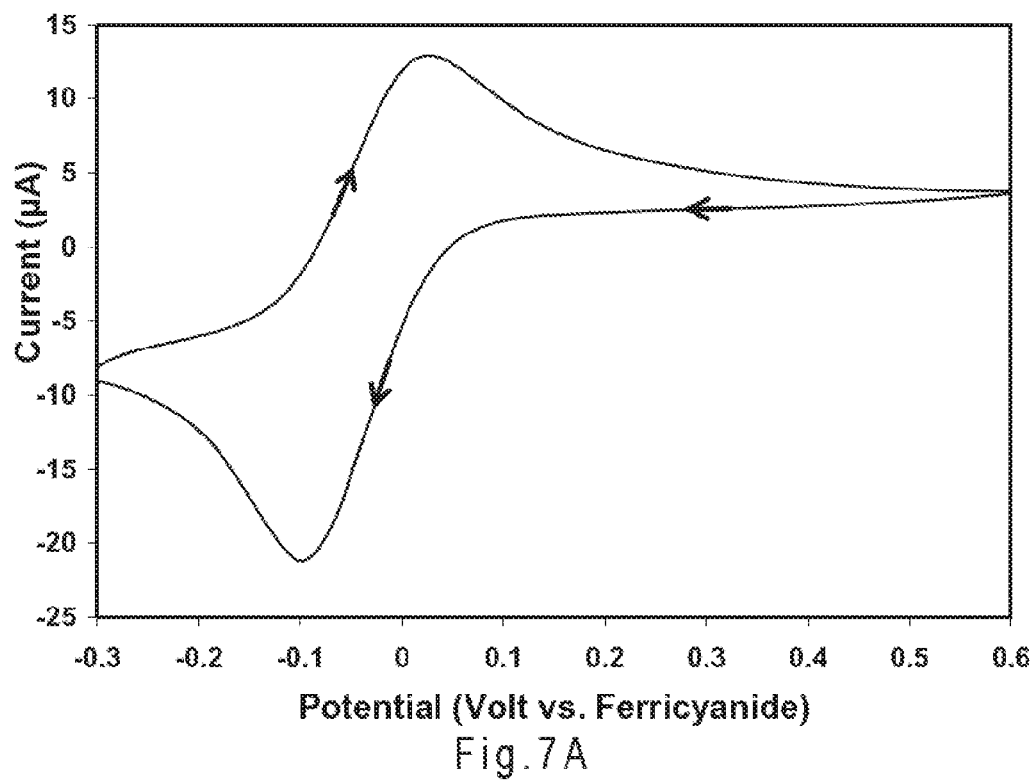
FIG. 7A is a graph showing a cyclic voltammogram from a sensor system.

FIG. 7A presents the data from a 25 mV/sec cyclic excitation of a ferricyanide/ferrocyanide redox pair as a cyclic voltammogram. The voltammogram is characterized by a forward current peak during the forward portion of the scan from −0.3 V to +0.6 V indicating ferrocyanide oxidation and a reverse current peak during the reverse voltage scan from +0.6 V back to −0.3 V indicating ferricyanide reduction. The forward and reverse current peaks center around the formal potential $E^{0\prime}$ of the ferrocyanide/ferricyanide redox pair, when referenced to the counter electrode. In this aspect, the potential of the counter electrode is substantially determined by the reduction potential of ferricyanide, the major redox species present on the counter electrode.

While the potentials where the forward and reverse scans begin (the excitation range) may be selected to include the reduced and oxidized states of the redox pair, the excitation range may be reduced to shorten the analysis time. However, the excitation range preferably includes the DLC region for the redox pair. For example, at a scan rate of 25 mV/sec, the concentration of the reduced [Red] and oxidized [Ox] species of the ferrocyanide/ferricyanide reversible redox pair and the resulting electrode potential are described by the Nernst equation as follows.

$$E = E^{0\prime} + \frac{RT}{nF} \ln \frac{[Ox]}{[Red]} \underline{T = 25^\circ\text{ C.}} \; E^0 + \qquad (1)$$

$$\frac{0.059}{n} \log \frac{[Ox]}{[Red]} \underline{n = 1} E^{0\prime} + 0.059 \log \frac{[Ox]}{[Red]}$$

In the Nernst equation, R is the gas constant of 8.314 Joul/(mole*K), F is the Faraday constant of 96,5000 Coul./equiv., n is the number of equivalents per mole, and T is the temperature in degrees Kelvin. When the potential at the working electrode is referenced to its own redox potential, the formal potential $E^{0\prime}$ will become substantially zero and the equation collapses to:

$$E = 0.059 \log \frac{[Ox]}{[Red]} = 0.059 \log \frac{[Fe(CN)_6^{-3}]}{[Fe(CN)_6^{-4}]}. \qquad (2)$$

From equation (2), when the ratio of the oxidized mediator to the reduced mediator changes by 10, the potential at the working electrode changes by about 60 mV. The reverse is also true. Thus, for ferricyanide [Ox] to ferrocyanide [Red] concentration ratios of 10:1, 100:1, 1000:1 and 10,000:1, the potential at the working electrode will be approximately 60, 120, 180, and 240 mV away from the zero potential, respectively.

Thus, when the ratio of ferricyanide to ferrocyanide is ~1000:1, a scan range of −180 mV to +180 mV would provide substantially complete oxidation of the reduced species at the working electrode. At 180 mV, the oxidation rate is limited by how fast the reduced form of the mediator can diffuse to the conductor surface, and from this potential forward, there exists a DLC region. Thus, if the reversing point is set ~400 mV from the zero potential, ~200 mV of DLC region may be provided.

For reversible systems, it may be preferable to provide an excitation range of from 400 to 600 mV, thus exciting from 200 to 300 mV on each side of the formal potential $E^{0\prime}$ of the redox pair. For quasi-reversible systems, it may be preferable to provide an excitation range of from 600 to 1000 mV, thus exciting from 300 to 500 mV on each side of the formal potential $E^{0\prime}$ of the redox pair.

The larger excitation range may be preferred for quasi-reversible systems because the DLC region may be smaller. In addition to redox pairs that are inherently quasi-reversible, fast scan excitation may cause a redox pair that is reversible at slow excitation rates to demonstrate quasi-reversible behavior. Thus, it may be preferable to provide a larger quasi-reversible excitation range for a reversible redox pair at fast excitation rates.

Preferably, at least 25, 50, 100, 150, or 300 mV of DLC region is provided by the selected excitation range. In another aspect, the reversing point for a cyclic or acyclic excitation is selected so that from 25 to 400 mV, from 50 to 350 mV, from 100 to 300 mV, or from 175 to 225 mV of DLC region is provided. For reversible systems, the reversing point for a cyclic or acyclic excitation may be selected so that from 180 to 260 mV or from 200 to 240 mV of DLC region is provided. For quasi-reversible systems, the reversing point for a cyclic or acyclic excitation may be selected so that from 180 to 400 mV or from 200 to 260 mV of DLC region is provided.

Figure 7B:
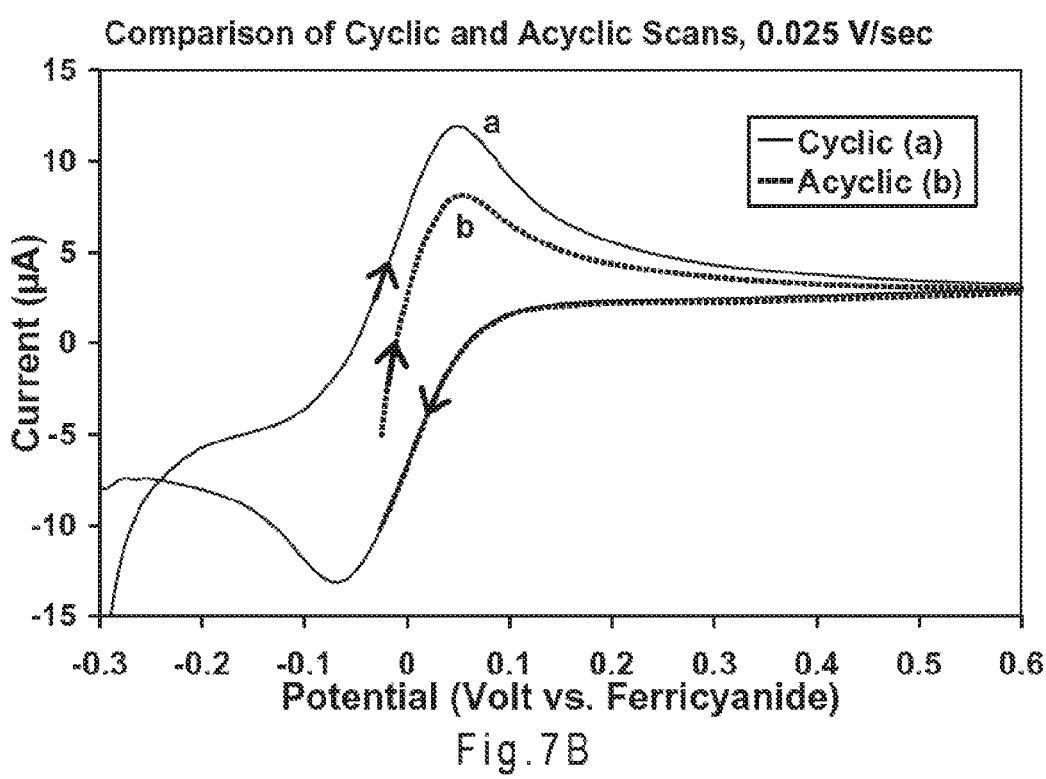
FIG. 7B compares a cyclic scan to an acyclic scan, where the forward excitation of the acyclic scan was started near the formal potential $E^{o\prime}$ for the redox pair.

Once the reversing point is selected to provide the desired DLC region, the duration of the reverse scan may be selected for an acyclic scan. As can be seen in FIG. 7B, starting the forward scan and terminating the reverse scan at approximately −0.025 mV resulted in an acyclic scan that included more of the forward current peak than the reverse current peak. From the FIG. 7B comparison, while the peak currents obtained for the cyclic (a) and acyclic (b) scans differ, the DLC region of the scans were nearly the same, especially with regard to the reverse scan.

Figure 7C:
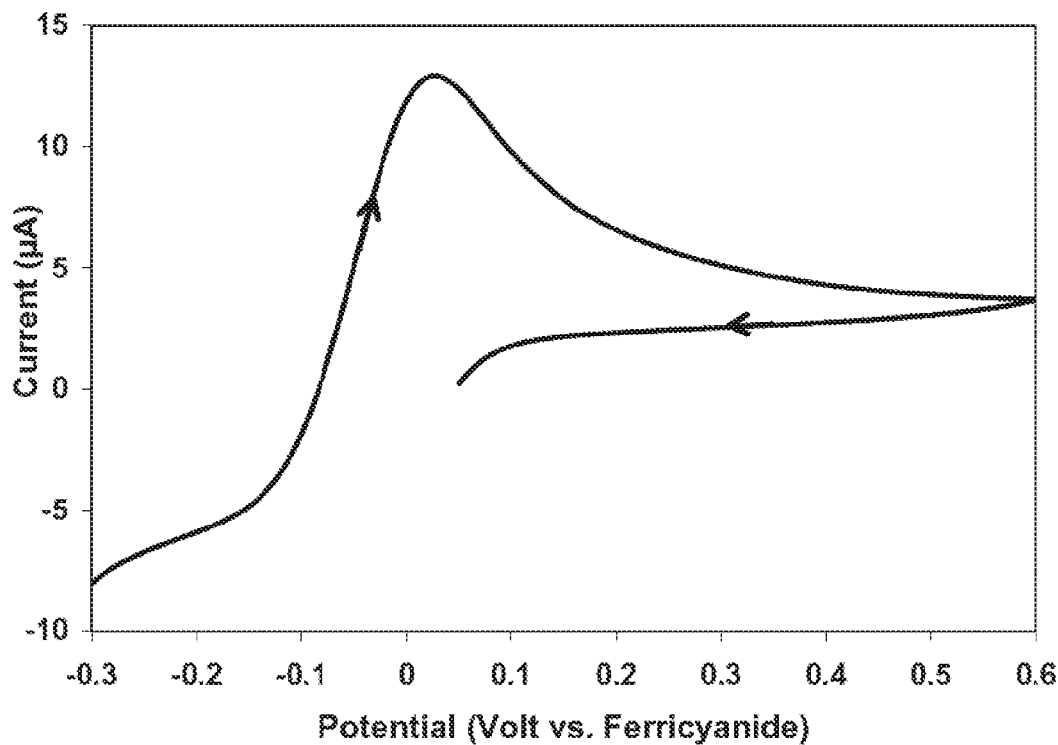
FIG. 7C shows an acyclic scan, where the reverse scan is terminated the reverse current peak.

In another aspect, the reverse excitation may be terminated before the reverse current peak is reached, as depicted in FIG. 7C. When the forward excitation was started at a potential sufficiently negative, such as at −0.3 mV in FIG. 7C, to the middle of the potential range of the redox pair, such as −0.05 mV in FIG. 7C, the forward excitation included the full range of the redox potential of the redox pair. Thus, by terminating the reverse excitation at a potential from 50 to 500 mV, from 150 to 450, or from 300 to 400 mV negative from the reversing point, for example, the reverse current peak may be excluded for the ferricyanide/ferrocyanide redox pair.

Similarly, the reverse excitation also may be terminated before the reverse current peak is reached by terminating the excitation when the reverse excitation current deviates in value from the DLC. A change in the reverse excitation current of at least 2%, 5%, 10%, or 25% may be used to indicate the beginning of the reverse excitation current peak.

Figure 7D:
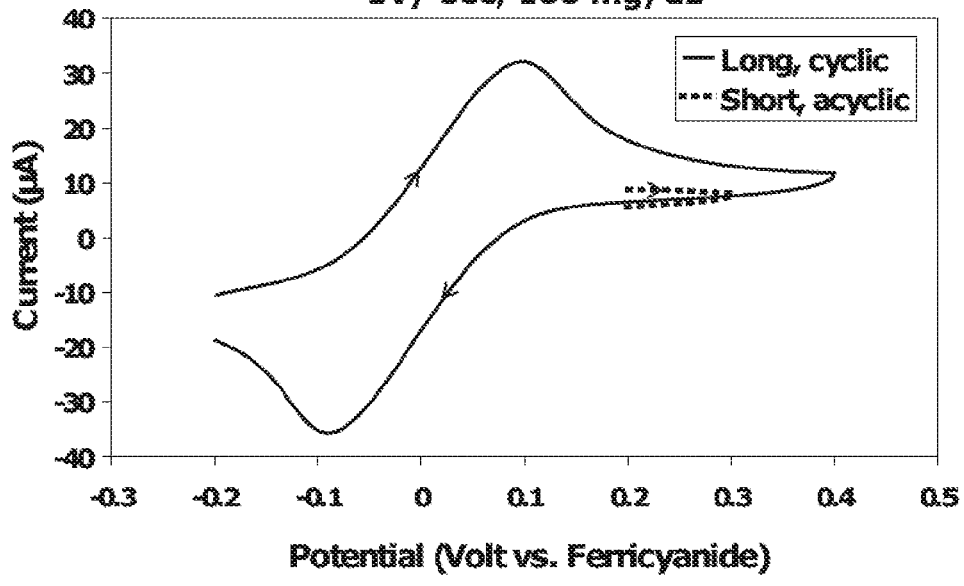
FIG. 7D shows a cyclic scan with an acyclic scan superimposed in the DLC region.

FIG. 7D compares a 1 V/sec cyclic voltammogram including the forward and reverse oxidation peaks of the redox pair with a 1 V/sec acyclic voltammogram that excludes the forward and reverse oxidation peaks of a redox pair. The acyclic excitation had starting and ending points of 200 mV and a reversing point of 300 mV. Preferable excitation ranges for acyclic excitations within the DLC region of the ferricyanide/ferrocyanide redox pair, which exclude the forward and reverse oxidation and reduction peaks, are from 10 to 200 mV, more preferably from 50 to 100 mV. While the cyclic voltammogram including the complete scan range significantly decayed after reaching the current peak, the acyclic voltammogram provided a substantially flat current region over the scan range. This current region may be directly correlated with the analyte concentration of the sample.

As seen in FIG. 7D, the current values recorded for the acyclic excitation are numerically smaller than those of the cyclic excitation, while the background current is lower for the acyclic excitation. This beneficial reduction in background current was unexpectedly obtained without having to initiate the acyclic excitation in the reduction peak portion of the cyclic excitation. Thus, a fast and short acyclic excitation within the DLC region of a redox pair may increase the accuracy of analyte determination due to a reduction in the background current, which may provide an increase in the signal-to-background ratio.

Cyclic and acyclic excitations may provide multiple benefits in relation to linear excitations. In one aspect, the portion of the reverse scan from the reversing point to the point where the reverse current peak begins may be a better representation of the true DLC values than the DLC region of the forward scan. The DLC region of the reverse excitation may be a more accurate representation of analyte concentration for quasi-reversible redox systems or at fast excitation rates because the forward excitation may not show a distinct DLC region.

Acyclic excitations may have multiple advantages over cyclic excitations including a shorter excitation time and a substantial decrease in the amount of mediator electrochemically converted to the measurable state. Thus, if the mediator is reduced in response to the analyte and electrochemically oxidized during measurement, terminating the reverse excitation before the oxidized mediator is electrochemically reduced decreases the amount of reduced mediator in the sample not responsive to the analyte. Similarly, starting the forward excitation at a potential above that at which the measurable species is reduced also may decrease the amount of reduced mediator in the sample not responsive to the analyte. Both acyclic excitations may allow for a shorter analysis time, a significant benefit for the user.

FIGS. 8A-8D show the output dynamic currents plotted as a function of potential from the pulse sequence of FIG. 6C using 7 triangular waveform excitations for WB samples containing 40% hematocrit and 0, 50, 100, and 400 mg/dL of glucose. The scan rate was 1 V/sec. Instead of a conventional long duration read pulse resulting in extensive oxidation of the measurable species, each triangular excitation was followed by a relaxation to provide a break in the current profile. The currents from each successive excitation were plotted as a different "rep" line, thus providing rep1 through rep7 for each Figure.

Figure 8A:
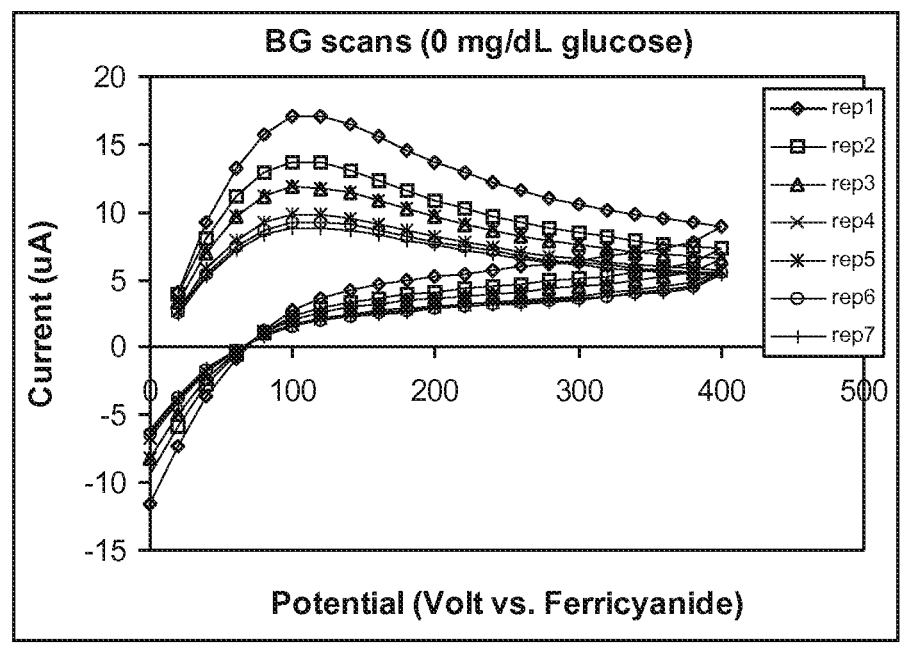
FIGS. 8A-8D shows the output currents plotted as voltammograms from the pulse sequence represented in FIG. 6C for 40% hematocrit WB samples containing 50, 100, and 400 mg/dL glucose
Figure 8B:
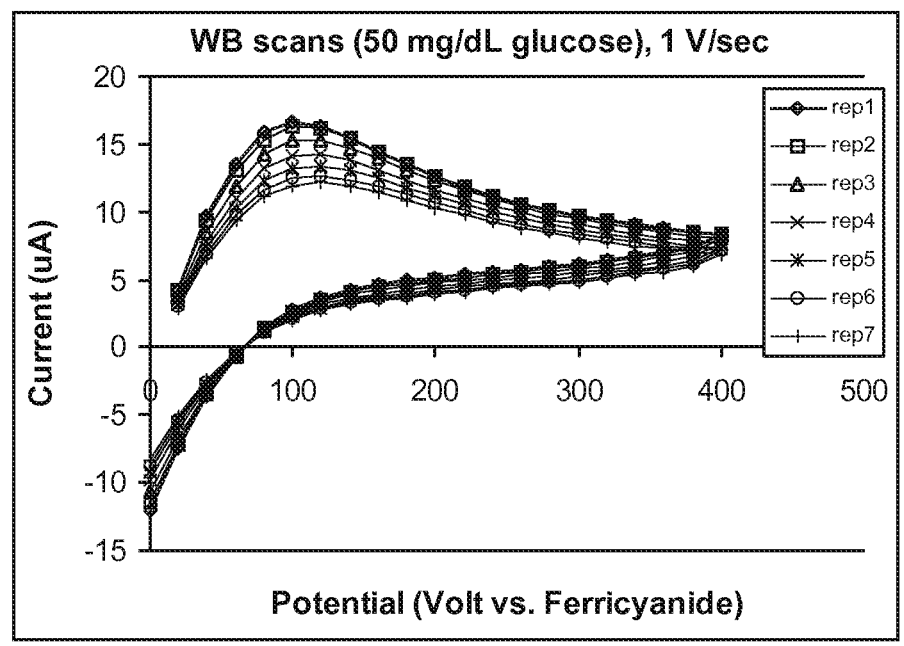
Figure 8C:
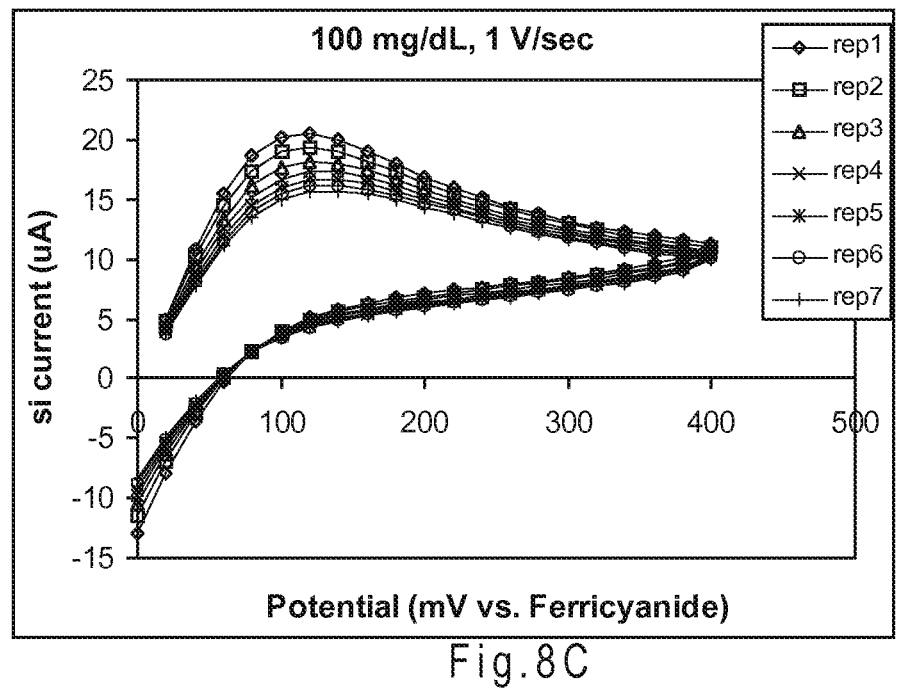
Figure 8D:
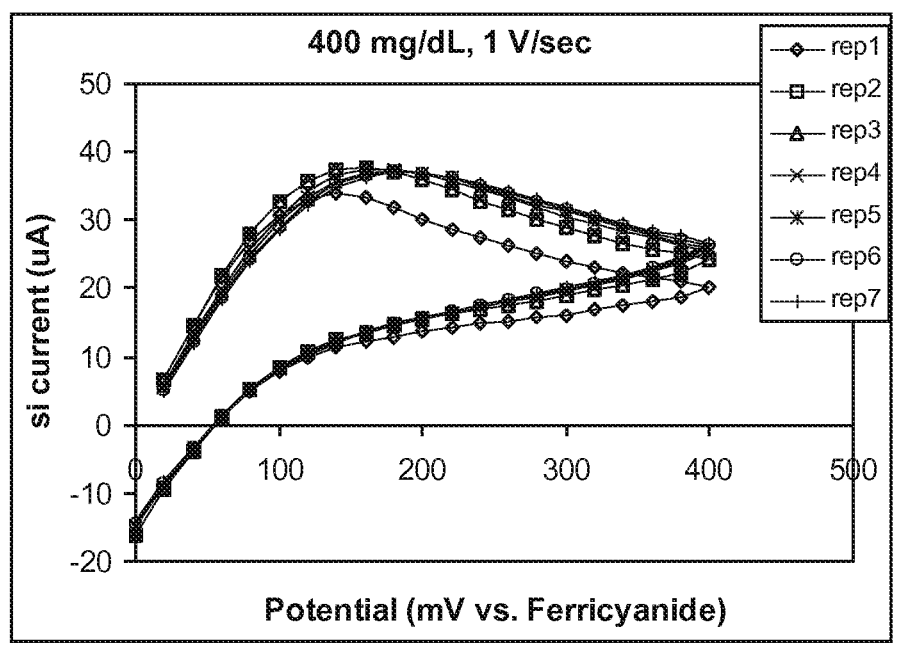
Figure 9A:
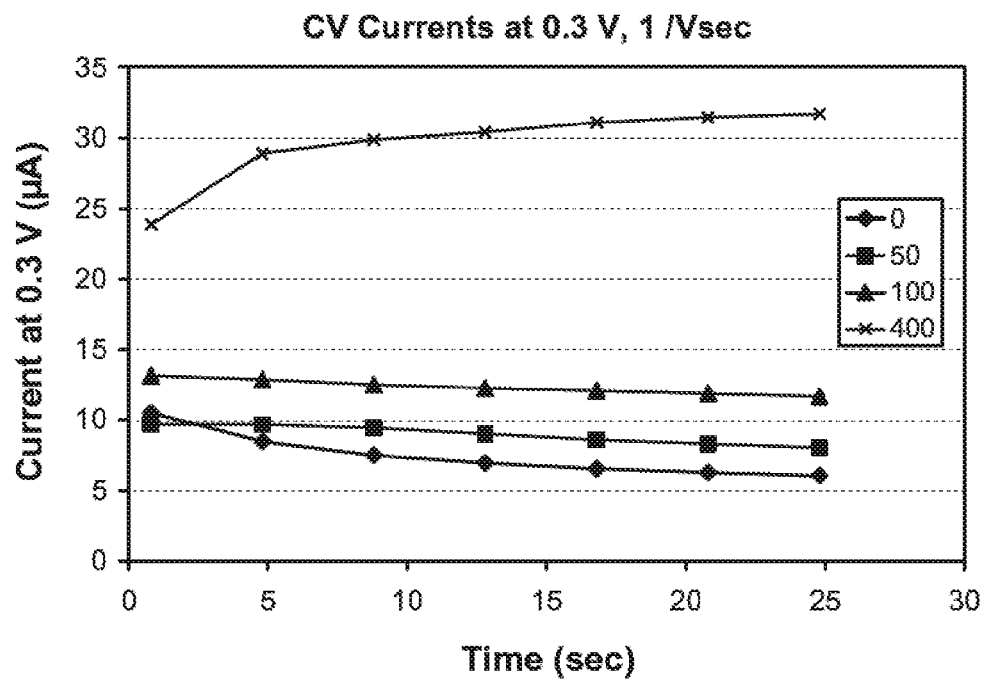
FIGS. 9A-9C show contour profiles of the voltammograms of FIGS. 8A-8C.
Figure 9B:
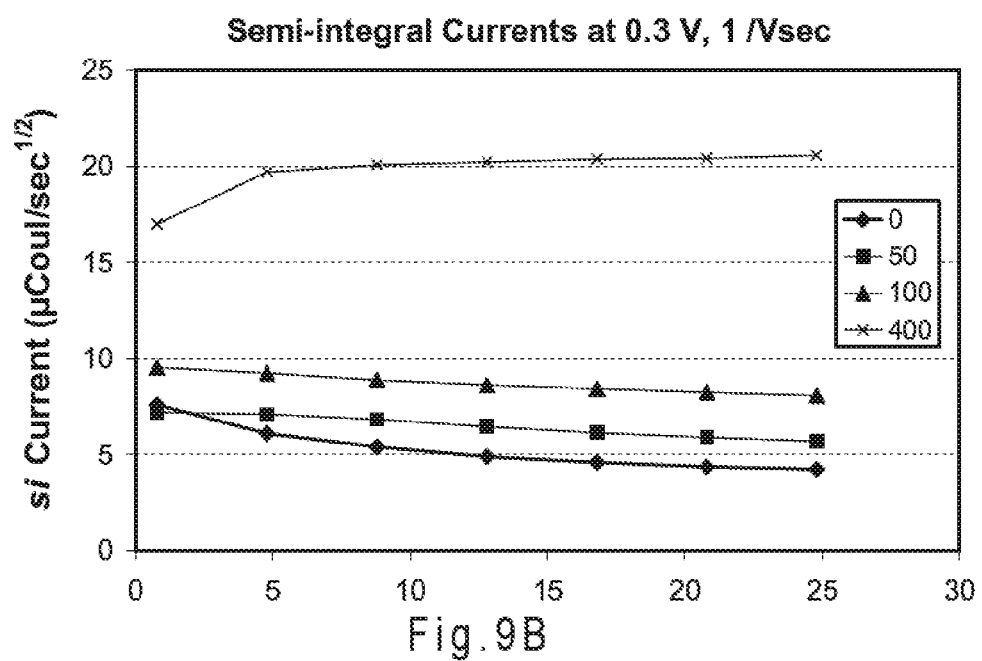
Figure 9C:
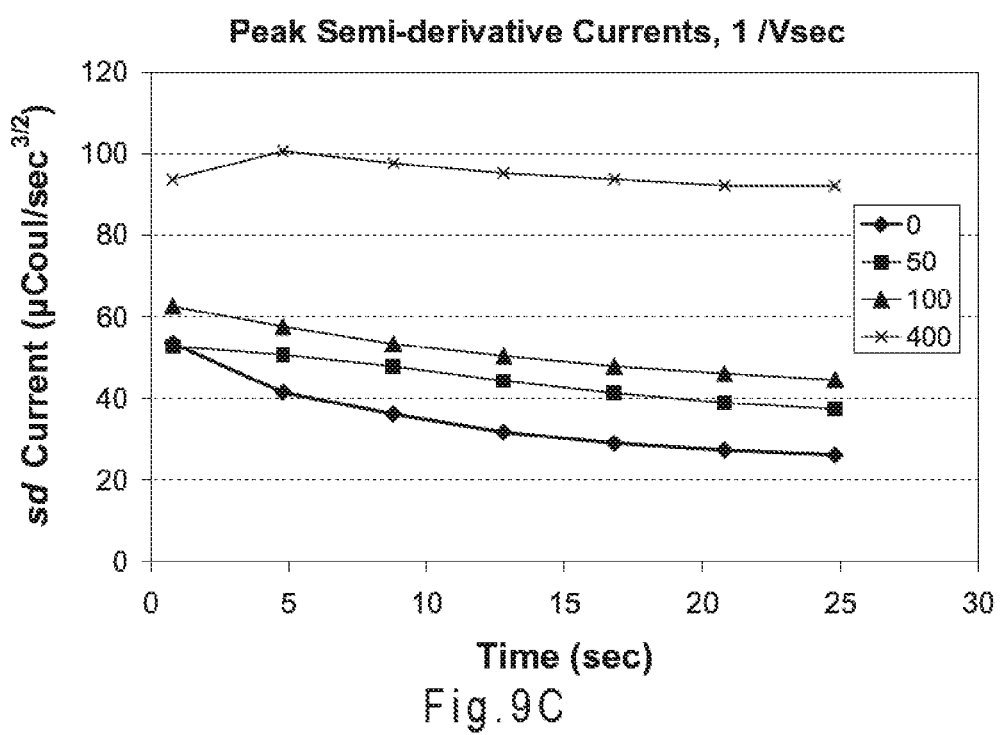

The current values from each of the multiple excitations (each rep) in the voltammograms of FIGS. 8A-8D were converted to a single data point and connected to give the contour profiles of FIGS. 9A-9C. For FIGS. 9A and 9B, the conversion was accomplished by selecting a current value at the same potential in the DLC region of each successive excitation, such as 300 mV. In FIG. 9A, the current values from FIGS. 8A-8D were directly plotted as a function of time from the ending of the pulse sequence. In FIG. 9B, a semi-integral data treatment was applied to the current values before plotting. For FIG. 9C, the multiple excitations were converted to single data points by selecting the peak current value of each rep and using a semi-derivative data treatment. In this manner, the X-axis of the contour profiles are expressed in terms of time, thus mimicking the data obtained from a conventional system at steady-state, where the current change with time is substantially constant. While the recorded voltammogram currents may be treated in multiple ways to extract useful information, semi-integral, semi-derivative, and derivative data treatments are presently preferred.

The dynamic current profiles obtained from gated voltammetric pulse sequences are fundamentally different from the current profiles obtained from a conventional analysis using a single read pulse. While currents recorded from a single read pulse derive from a single relaxation/diffusion, each time point in the contour profile of the dynamic currents originates from an excitation after an independent relaxation/diffusion process. Furthermore, as the length of an excitation increases, the correlation between the current and the analyte concentration may decrease, often due to the hematocrit effect. Thus, the accuracy of an analysis using multiple, short excitations may be increased in comparison to an analysis using a longer read pulse having the duration of the multiple excitations combined.

The application of these data treatments to glucose analysis is described below. However, a more in-depth discussion of data treatments for transforming electrochemical currents and the related digital implementations may be found in Bard, A. J., Faulkner, L. R., "Electrochemical Methods: Fundamentals and Applications," 1980; Oldham, K. B.; "A Signal-Independent Electroanalytical Method," Anal. Chem. 1972, 44, 196; Goto, M., Oldham, K. B., "Semi-integral Electroanalysis: Shapes of Neopolarograms," Anal. Chem. 1973, 45, 2043; Dalrymple-Alford, P., Goto, M., Oldham, K. B., "Peak Shapes in Semi-differential Electroanalysis," Anal. Chem. 1977, 49, 1390; Oldham, K. B., "Convolution: A General Electrochemical Procedure Implemented by a Universal Algorithm," Anal. Chem. 1986, 58, 2296; Pedrosa, J. M., Martin, M. T., Ruiz, J. J., Camacho, L., "Application of the Cyclic Semi-Integral Voltammetry and Cyclic Semi-Differential Voltammetry to the Determination of the Reduction Mechanism of a Ni-Porphyrin," J. Electroanal. Chem. 2002, 523, 160; Klicka, R, "Adsorption in Semi-Differential Voltammetry," J. Electroanal. Chem. 1998, 455, 253.

Semi-integration of a voltammogram may separate the DLC from the hematocrit affected equilibrium current (initial peak) because separate signals may be observed for the hematocrit-affected equilibrium si current and the hematocrit. This is especially true at slow scan rates. The semi-integral of the experimentally obtained voltammetric current i(t) has the following mathematical form:

$$\frac{d^{-1/2}}{dt^{-1/2}} i(t) = I(t) = \frac{1}{\pi^{1/2}} \int_0^t \frac{i(u)}{(t-u)^{1/2}} du \quad (3)$$

where i(t) is the time function of the voltammetric current obtained during the scan;

l(t) is a transformation and the semi-integral of i(t);

u is a transformation parameter; and $d^{-1/2}/dt^{-1/2}$ is the semi-integration operator.

At a sufficiently high oxidation potential, the steady-state semi-integral current is given by:

$$l_{lim} = nFAD^{1/2}C (\text{coul/sec}^{1/2}) \quad (4)$$

where $l_{lim}$ is the DLC under the condition of the surface concentration of the oxidizable species being zero. Note that the unit of semi-integral current is coul/sec$^{1/2}$, which is not the traditional unit for expressing electrical current, which is coul/sec.

For simplicity, $l_{lim}$ is referred to as the semi-integration DLC(SI) with a unit of coul/sec$^{1/2}$. This SI current (coul/sec$^{1/2}$) is only a half-step integration from current (coul/sec). The half-step integration is fundamentally different from coulometry where a full integral is applied to the i-t curve to provide the total charge passing through the electrodes.

Although equation (3) gives a theoretical definition of the semi-integral, for digital processing the i-t data may be divided into N equally spaced time intervals between t=0 and t=NΔt. One such digital processing algorithm is given by equation (5) where t=kΔt and u=jΔt, and i is determined at the midpoint of each interval.

$$I(k\Delta t) = \frac{1}{\pi^{1/2}} \sum_{j=1}^{j=k} \frac{i(j\Delta t - 1/2\Delta t)\Delta t^{1/2}}{\sqrt{k - j + 1/2}} \quad (5)$$

A preferred algorithm for digital processing is given by:

$$I(k\Delta t) = \frac{1}{\pi^{1/2}} \sum_{j=1}^{j=k} \frac{\Gamma(k - j + 1/2)}{(k - j)!} \Delta t^{1/2} i(j\Delta t) \quad (6)$$

where $\Gamma(x)$ is the gamma function of x, where $\Gamma(1/2)=\pi^{1/2}$, $\Gamma(3/2)=1/2\pi^{1/2}$, and $\Gamma(5/2)=3/2*1/2\pi^{1/2}$, etc.

From equation (4) it may be seen that the SI current lacks the time-dependence factor of conventional amperometric methods. Thus, the SI current response may be considered a series of plateau currents, instead of the continuously changing amperometric currents obtained from conventional amperometry. Because the semi-integration allows for quantification of the DLC, a faster scan rate may be used than when peak currents are quantified. Thus, linear, cyclic, or acyclic voltammetry in combination with semi-integration may rapidly generate a DLC in response to glucose concentrations. In this manner, the disadvantages of the long wait times of coulometry and the non-steady-state nature of the current in conventional amperometry may be reduced.

Equation (4) also shows that reversible or quasi-reversible redox pairs are preferred for use with semi-integration. This is because the semi-integral from a reversible or quasi-reversible redox pair can exhibit a sharp transition from the reduced state to the oxidized state (and vice versa) and a wide DLC region, thus making the transition easier to determine. Ferricyanide/ferrocyanide and the +3 and +2 states of ruthenium hexaamine are examples of redox pairs demonstrating preferred reversible (slow scan) or quasi-reversible (fast scan) behaviors.

Poorly activated electrodes may not provide an acceptable DLC condition even with reversible or quasi-reversible redox pairs. Thus, electrode activation procedures, such as those described in U.S. Pat. No. 5,429,735, may be used to achieve the preferred electrode activity.

In addition to semi-integrals, semi-derivatives of a voltammogram also may be used to quantify the analyte by measuring the peak of the semi-derivative. The semi-derivative of the experimentally obtained voltammetric current i(t) has the following mathematical forms:

$$\frac{d^{1/2}}{dt^{1/2}} i(t) \quad (7)$$

$$\frac{d^{1/2}}{dt^{1/2}} i(t) = \frac{dI(t)}{dt} = \frac{d}{dt}\left[\frac{1}{\pi^{1/2}} \int_0^t \frac{i(u)}{(t-u)^{1/2}} du\right], (coul/\sec^{3/2}) \quad (8)$$

where I(t) is the semi-integral of the time function i(t). The equations used for the semi-integral, semi-derivative, and the derivative data treatment described below, were implemented with the Electrochemical Workstation software package, version 4.07, revised Apr. 26, 2004, which accompanies the CH Instruments Electrochemical Workstation, model CHI 660A.

Figure 10A:
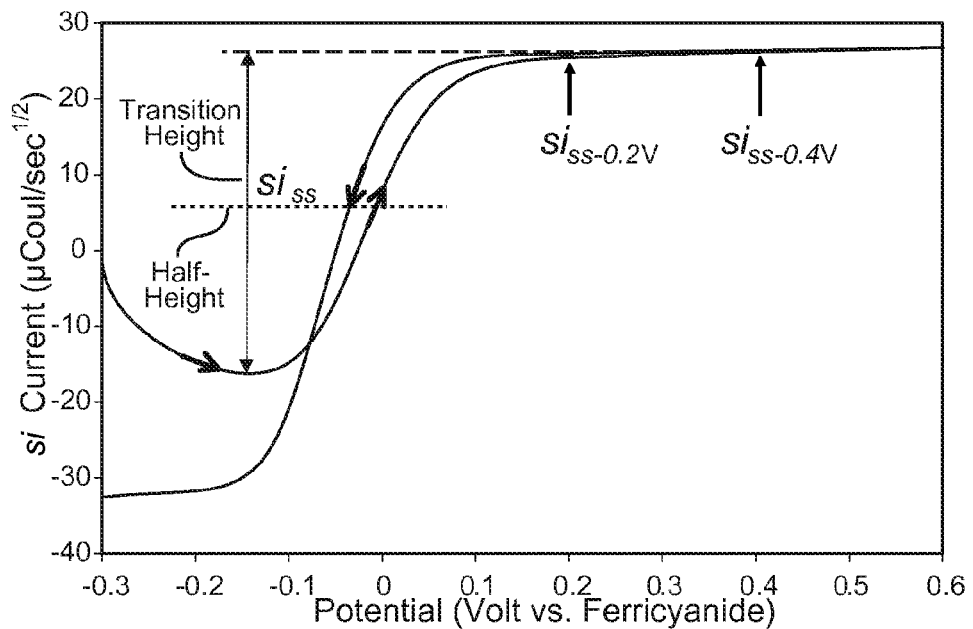
FIG. 10A is a graph of the semi-integral corresponding to the cyclic voltammogram of FIG. 7A.
Figure 10B:
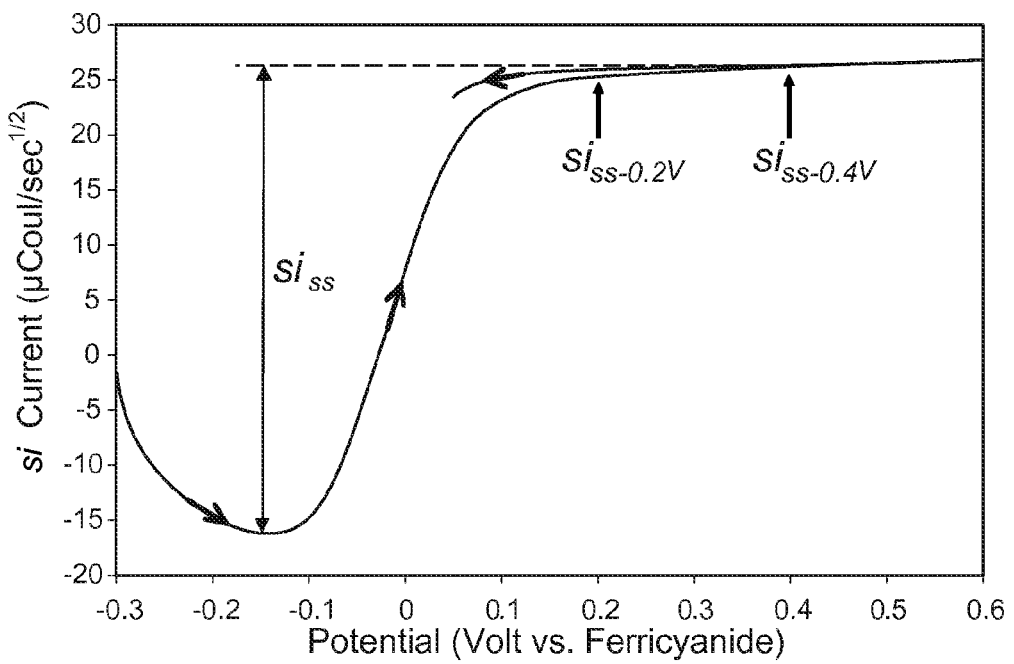
FIG. 10B presents the semi-integral of the acyclic data corresponding to the acyclic voltammogram of FIG. 7C.
Figure 10C:
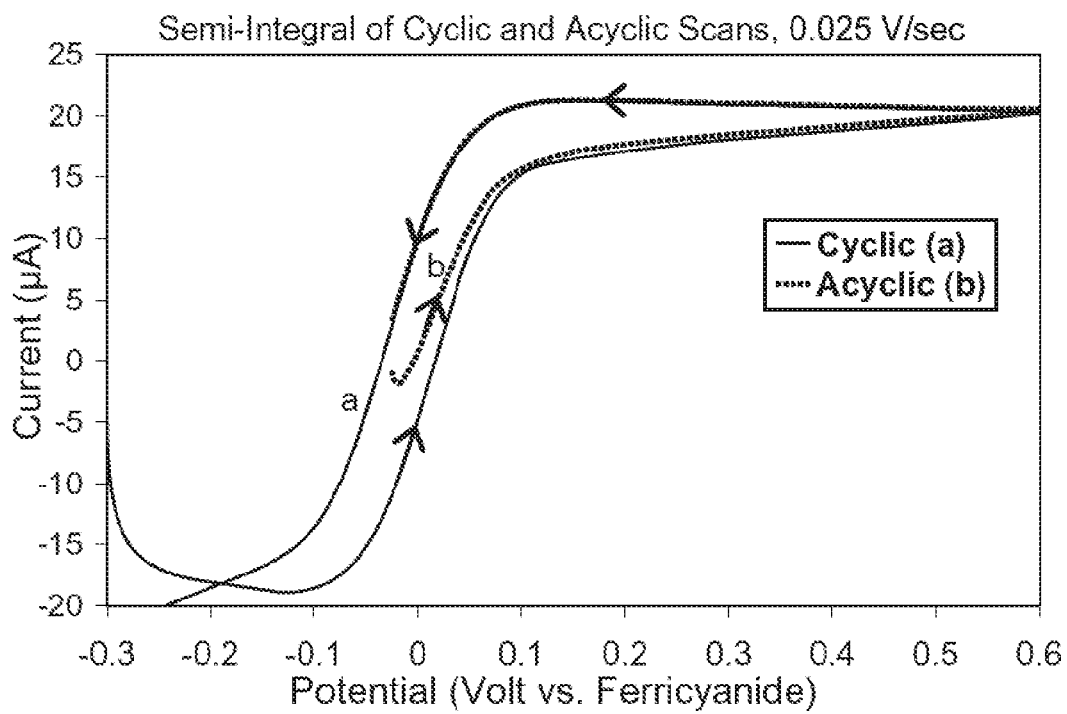
FIG. 10C presents the semi-integrals of the cyclic and acyclic excitations of FIG. 7B.

FIG. 10A presents the semi-integral plot of the cyclic voltammogram from FIG. 7A. Similarly, FIG. 10B presents the semi-integral plot of the acyclic voltammogram from FIG. 7C, where the reverse excitation terminated before initiation of the reverse current peak. FIG. 10C establishes that when the semi-integral of the cyclic and acyclic excitations of FIG. 7B are plotted, the DLC region of the return scan was readily established, permitting an accurate current reading in as little as 50 mV from the reversing point. Furthermore, the peak portion of the semi-integral plot was responsive to the hematocrit content of the sample and the magnitude of the peak may be quantitatively related to the hematocrit level.

Figure 10D:
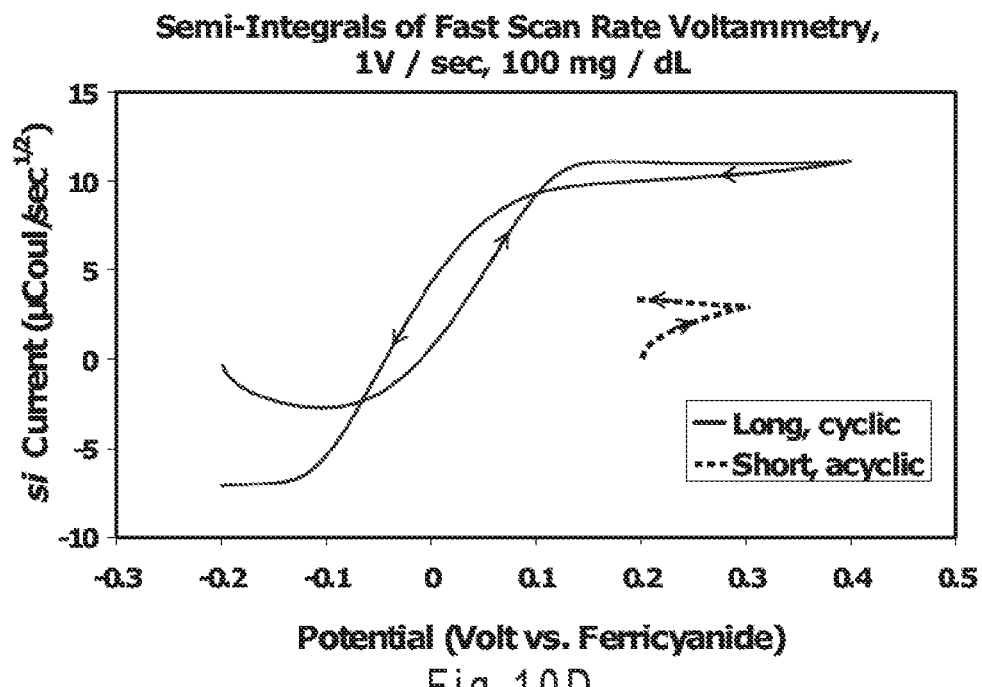
FIG. 10D shows the semi-integral and recorded current values for the acyclic excitation of FIG. 7D.

FIG. 10D shows the semi-integrals for the cyclic and 200 to 300 mV acyclic excitations of FIG. 7D. The shape of the si voltammogram from the short acyclic excitation differs from the voltammogram of the cyclic excitation because the region of oxidation-reduction transition is missing from the acyclic excitation. By starting the acyclic excitation in the DLC region, the background si current decreased at a faster rate in comparison to that observed for the cyclic voltammogram, thus improving the signal-to-background ratio for the acyclic excitation. Furthermore, the reverse si current from the acyclic excitation shows a plateau more accurately describing the analyte concentration of the sample than the forward si current. In this manner, the acyclic scan of the DLC region provided an increase in accuracy for the analysis when compared to the cyclic excitation.

Figure 11:
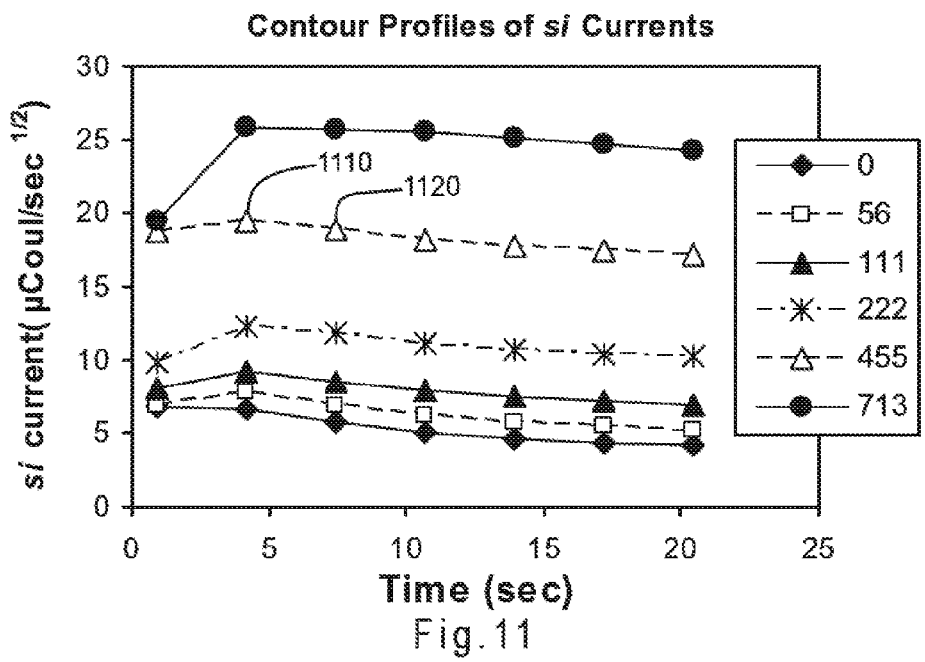
FIG. 11 shows contour profiles prepared by semi-integrating voltammograms from a seven excitation pulse sequence for WB samples containing varying amounts of glucose.

FIG. 11 shows contour profiles prepared by semi-integrating voltammograms from a seven excitation pulse sequence for WB samples containing 0, 56, 111, 221.75, 455.25, and 712.5 mg/dl of plasma glucose. For each of the glucose concentrations, equilibrium with regards to DBL rehydration was reached at the highest current value in the contour profile for each glucose concentration. Thus, readings 1110 (highest) and 1120 (lower) establish that equilibrium was reached regarding DBL rehydration at about four seconds for the 455 mg/dl glucose concentration.

Current values recorded at a relatively constant diffusion rate may minimize inaccuracies that would otherwise be introduced by variations in the rehydration and diffusion rates of the reagents. Thus, once a relatively constant diffusion rate is reached, the recorded current values may more accurately correspond to the concentration of the measurable species, and thus the analyte. Furthermore, for FIG. 11, the complete analysis may be completed in as few as seven seconds because once the highest current value 1110 of the contour profile is known, its value may be directly correlated to the analyte concentration. Additional data points may be obtained to reduce background error attributable to the mediator, as previously discussed with regard to RI.

Another form of data treatment that may be used to generate a contour profile is semi-derivatization. One implementation of a semi-derivative is to take a full step derivative of the semi-integral, as previously described in relation to equation (8). Unlike the plateau region representing the voltammetric scan in semi-integral plots, semi-derivative plots convert the voltammetric scan data into a peak centered at the transition of the redox pair.

Figure 12A:
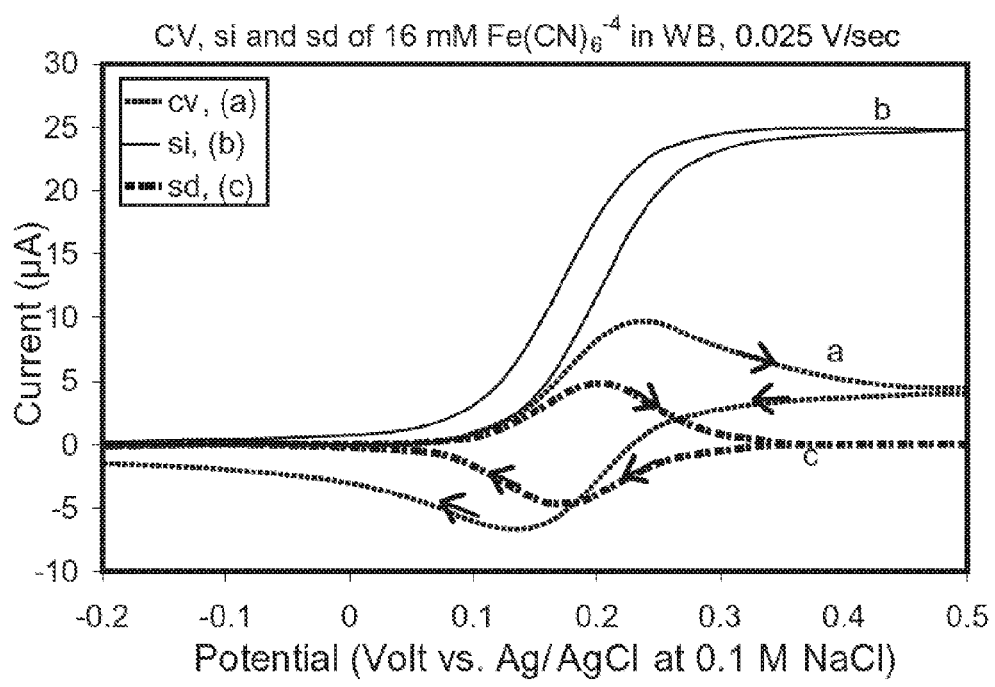
FIG. 12A depicts the cyclic voltammogram, semi-integral, and semi-derivative of 16 mM ferrocyanide in a 20% hematocrit WB sample.
Figure 12B:
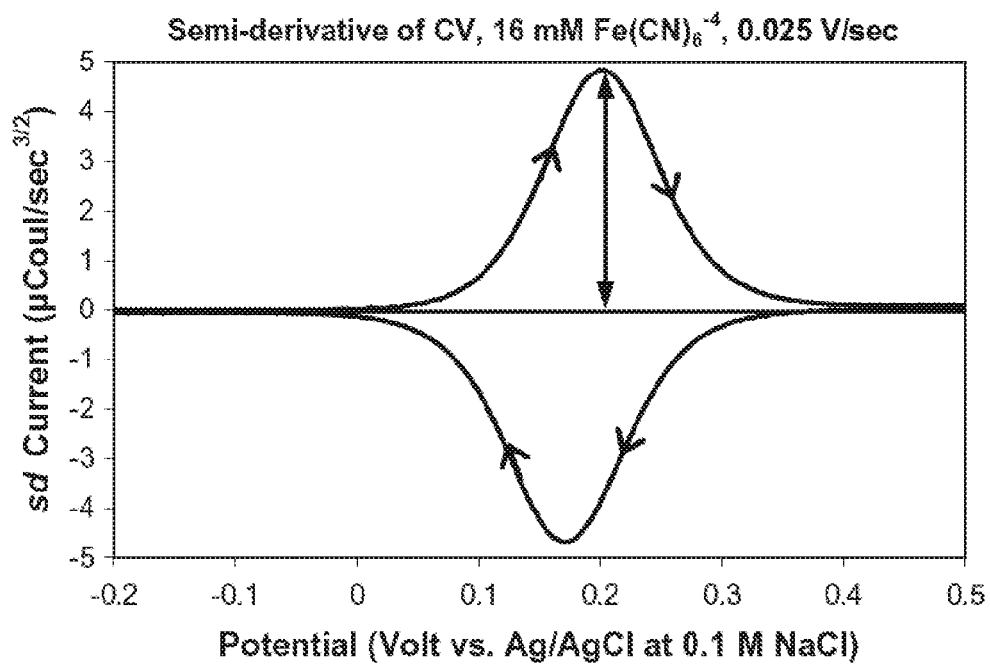
FIG. 12B is an enlargement of the semi-derivative curve of FIG. 12A.

FIG. 12A depicts the cyclic voltammogram (a), semi-integral (b), and semi-derivative (c) of 16 mM ferrocyanide in a 20% hematocrit WB sample. In this instance, the working electrode of the sensor strip lacked enzyme and oxidized mediator. FIG. 12B is an enlargement of the semi-derivative curve of FIG. 12A showing the peak height for the forward scan. The value of the forward or reverse scan peak height may be correlated with the analyte concentration of the sample. Furthermore, the semi-derivative data treatment may inherently provide hematocrit compensation for glucose determination, especially for samples including less than 40% hematocrit. A more detailed description of the application of semi-derivative data treatment to glucose analysis may be found in WO 2005/114164, filed May 16, 2005, entitled "Voltammetric Systems for Assaying Biological Analytes."

Figure 13A:
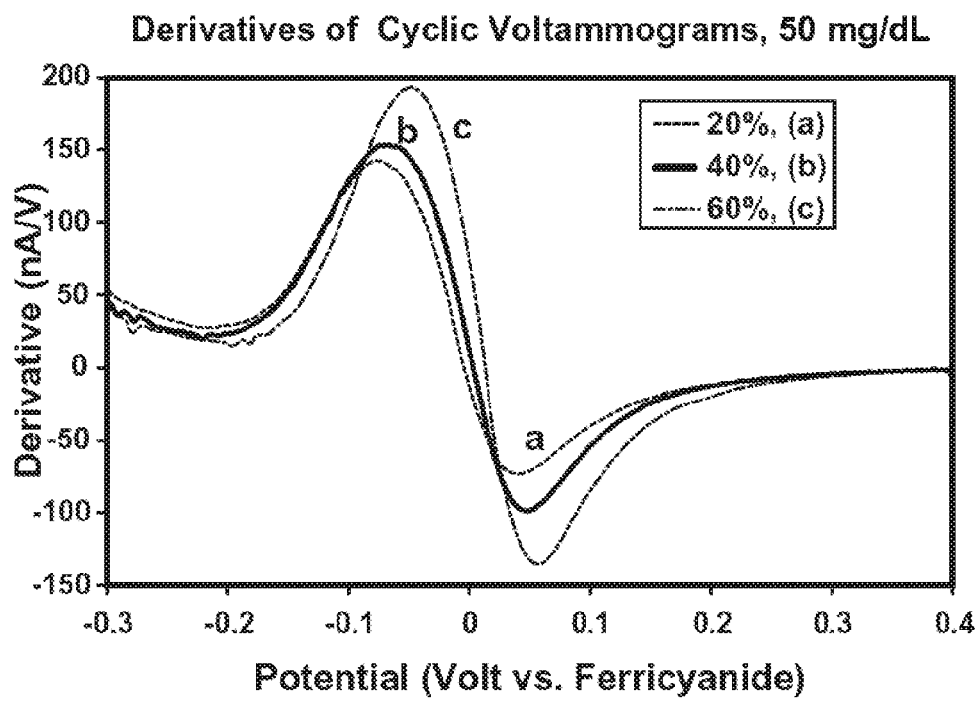
FIGS. 13A-13C depict the derivatives of cyclic voltammograms.
Figure 13B:
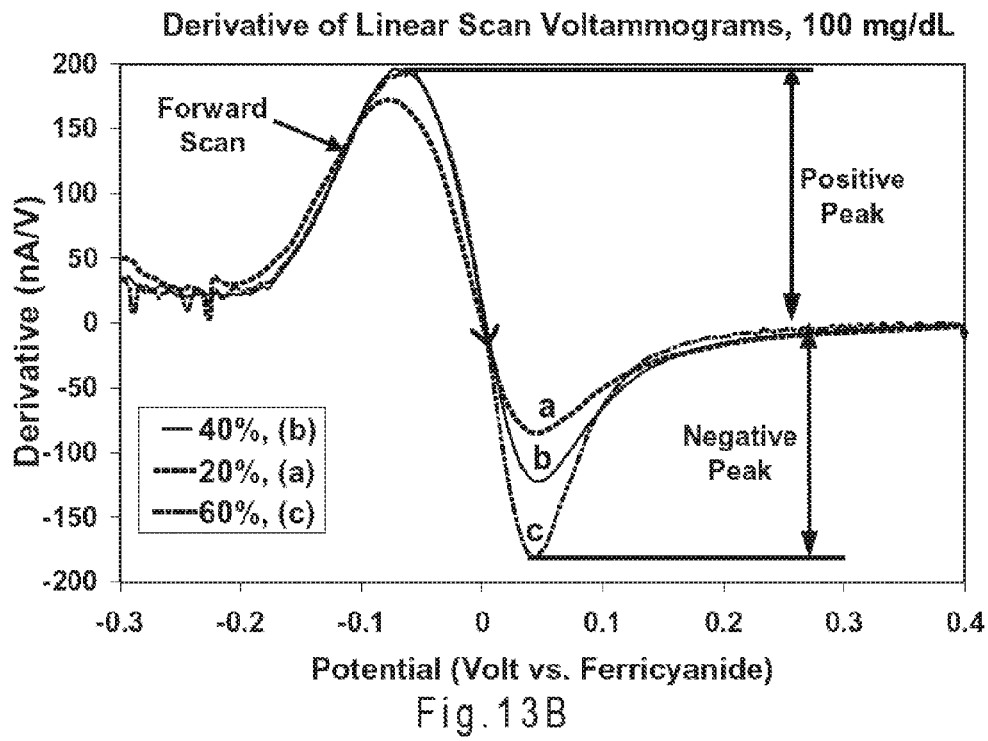
Figure 13C:
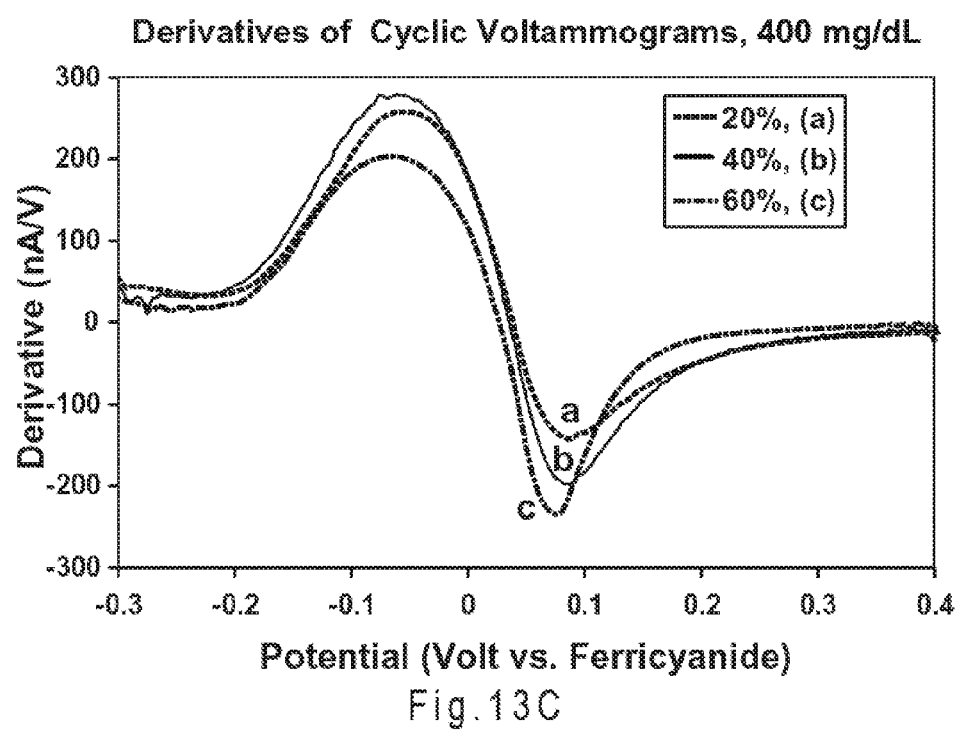

In addition to semi-integral and semi-derivative data treatments, a derivative data treatment also may be used to generate a contour profile, and thus determine the concentration of the analyte in the sample. FIGS. 13A-13C depict the derivatives of cyclic voltammograms for samples having 20, 40, and 60% hematocrit. These derivative plots show an initial increase in current as voltage increases, followed by a decrease, and finally a DLC region. The hematocrit effect may be seen in the negative peak located at about 0.1 volts in FIGS. 12A-12C, with higher RB cell concentrations reflected as more negative peak values.

While the values of the positive and negative derivative peaks, such as those depicted in the derivative plot of FIG. 13B, are concentration dependent, the ratio of the negative peak to the positive peak cancels out the concentration dependence, thus being hematocrit dependent. Because this ratio (HI-DER) is concentration independent and hematocrit dependent, the ratio indicates the percent hematocrit in the sample. Thus, this ratio of the derivative peaks may be used to determine a hematocrit compensation equation for analyte determination. A more detailed description of the application of derivative data treatment to glucose analysis may be found in WO 2005/114164.

In addition to the ability of the gated pulse sequences to reduce inaccuracy from the hematocrit effect and from the mediator background signal, the combination of the dynamic current profile of each excitation and the resulting contour profiles may be used to provide multiple sets of calibration constants to the sensor system, thus increasing the accuracy of the analysis. Each set of calibration constants obtained may be used to correlate a specific current reading to a specific concentration of measurable species in the sample. Thus, in one aspect, an increase in accuracy may be obtained by averaging the glucose values obtained using multiple sets of calibration constants.

Conventional electrochemical sensor systems generally use one set of calibration constants, such as slope and intercept, to convert current readings into a corresponding concentration of the analyte in the sample. However, a single set of calibration constants may result in inaccuracies in the analyte concentration determined from the recorded current values because random noise is included in the measurement.

Figure 14:
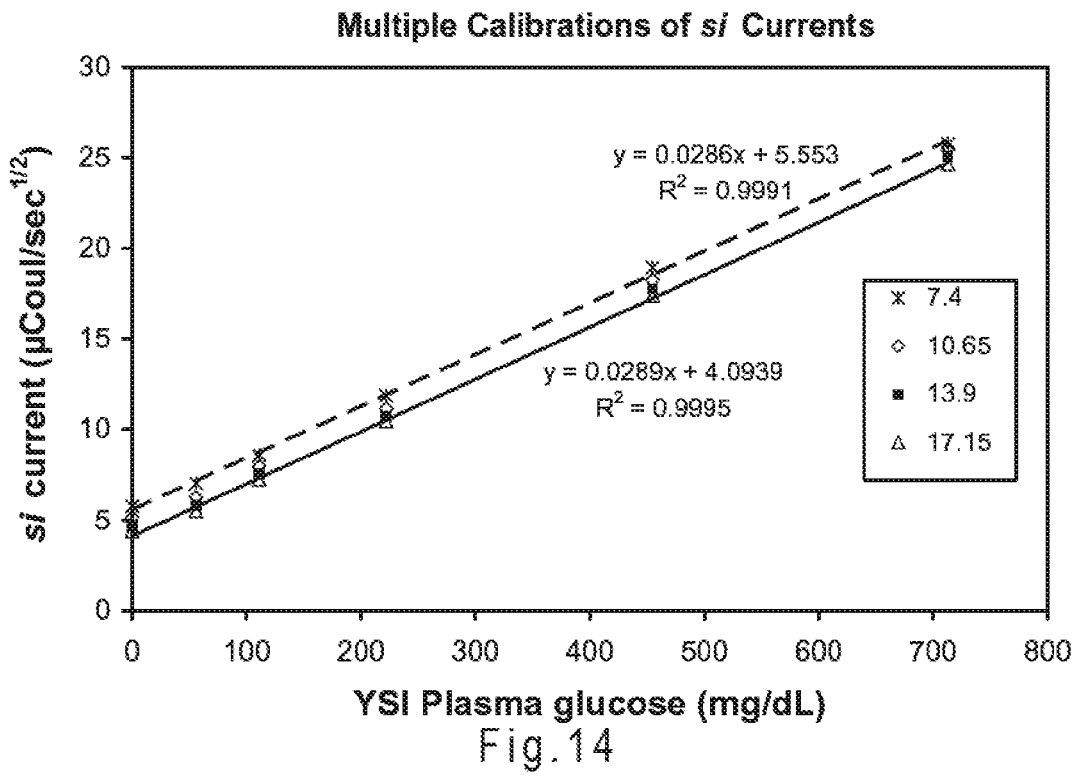
FIG. 14 plots the semi-integral currents recorded as a function of time for the contour profiles of FIG. 11.

By taking the current value or the transformed current value after data treatment at a fixed time within each duty cycle of a gated voltammetric pulse sequence, multiple sets of calibration constants may be established. FIG. 14 plots the semi-integral currents recorded at 7.4, 10.65, 13.9, and 17.15 seconds for the contour profiles of FIG. 11. Each of these four calibration lines are independent of the other and may be used in at least two ways.

First, the multiple sets of calibration constants may be used to determine the number of duty cycles that should be applied during the pulse sequence to obtain the desired accuracy and precision. For example, if the current values obtained from the first three excitations indicate a high glucose concentration, such as >150 or 200 mg/dL, the sensor system may terminate the analysis early, such as after the 4$^{th}$ excitation depicted in FIG. 11. In this manner, the time required for the analysis may be substantially shortened. Such a shortening may be possible because imprecision at high glucose concentrations is typically less than at lower glucose concentrations. Conversely, if the current values obtained from the first three excitations indicate a low glucose concentration, such as 150 or 100 mg/dL, the sensor system may extend the analysis to greater than 5 or 7 excitations. Thus, the accuracy and/or precision of the analysis may be increased by including 5 or more duty cycles.

Second, the multiple sets of calibration constants may be used to increase the accuracy and/or precision of the analysis by averaging. For example, if the target glucose measurement time is 17.15 seconds, the currents at 10.65, 13.9, and 17.15 seconds can be utilized to calculate the glucose concentrations using the slopes and intercepts from the corresponding calibration lines; therefore, $G_{10.65}=(i_{10.65}-\text{Int}_{10.65})/\text{Slope}_{10.65}$, $G_{13.9}=(i_{13.9}-\text{Int}_{13.9})/\text{Slope}_{13.9}$, and $G_{17.15}=(i_{17.15}-\text{Int}_{17.15})/\text{Slope}_{17.15}$. Theoretically, these three glucose values should be equivalent, differing only by random variations. Thus, the glucose values $G_{10.65}$, $G_{13.9}$, and $G_{17.15}$ may be averaged and the final glucose value of $(G_{10.65}+G_{13.9}+G_{17.15})/3$ may be calculated. Averaging the values from the calibration lines may provide a reduction in noise at the rate of $1/\sqrt{3}$).

An unexpected benefit of gated voltammetric pulse sequences including relatively short excitations and relatively long relaxations, such as that depicted in FIG. 6C, is the ability to simplify calibration. While the multiple sets of calibration constants that may be obtained from the dynamic and contour profiles may provide an advantage to the accuracy of the analysis, a pulse sequence such as depicted in FIG. 6C, may provide similar accuracy to that obtained using multiple sets of calibration constants from a single set of calibration constants. This effect may be observed in the contour profiles of FIG. 11 and the resulting calibration lines in FIG. 14.

This unexpected increase in accuracy may be attributable to the relatively long relaxation times in comparison to the short relaxations. In one aspect, excitation/relaxation time (ERT) ratios from 0.3 to 0.2 are preferred, with ERT ratios from 0.27 to 0.22 being more preferred. For example, a gated voltammetric pulse sequence having an ERT ratio of 0.25 (0.8 seconds/3.2 seconds), such as depicted in FIG. 6C, may be preferred to a pulse having an ERT ratio of greater than 0.3, such as the FIG. 6B pulse sequence having an ERT ratio of 0.56 (1.4 seconds/2.5 seconds). While not intending to be bound by any particular theory, the relatively long relaxation times may provide a state where the average consumption rate of measurable species during the excitation is balanced by the supply rate of measurable species diffusing into the DBL. In this manner, the multiple sets of calibration constants may collapse into a single set and the conversion of the recorded data into an analyte concentration may be simplified by carrying out the averaging process on the recorded current data before determining the analyte concentration.

The dynamic current profiles provided by the multiple duty cycles may be used to determine if the sensor strip has been under-filled with sample, thus allowing the user to add additional sample to the sensor strip. In addition to working and counter electrodes, conventional sensor systems may determine an under-fill condition through the use of a third electrode or electrode pair; however, the third electrode or electrode pair adds complexity and cost to the sensor system.

Conventional two electrode systems may be able to recognize that an analysis is "bad," but may not determine if the reason for the failed analysis was caused by under-fill or a defective sensor strip. The ability to determine if under-fill caused the failure of the analysis is beneficial because it may be corrected by adding additional sample to the same sensor strip and repeating the analysis, thus preventing a good strip from being discarded.

Figure 15:
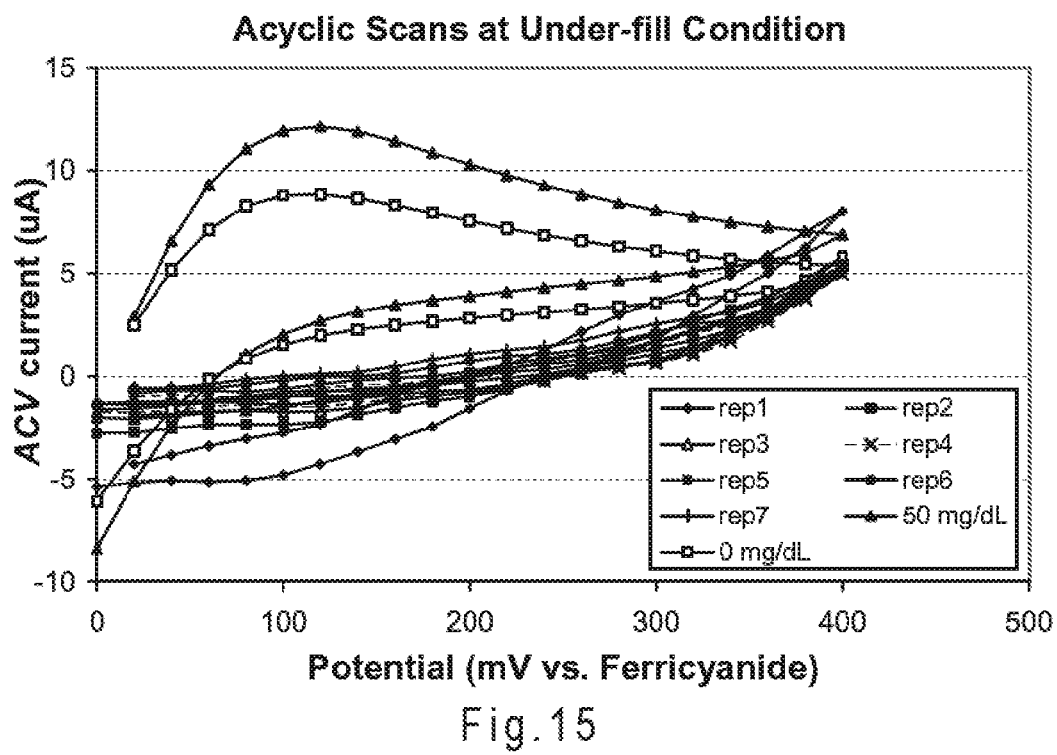
FIG. 15 depicts the cyclic voltammograms obtained from an under-filled sensor strip.

FIG. 15 depicts the cyclic voltammograms obtained from an under-filled sensor strip, while FIG. 8A depicts a series of seven cyclic voltammograms obtained with a gated voltammetric pulse sequence from a normal-filled sensor strip. In both instances, the scan rate was 1 V/sec. Even though the FIG. 8A sample lacked any glucose and the sample used for FIG. 15 included 400 mg/dL of glucose, the current values obtained from the under-filled strip having the 400 mg/dL glucose concentration were much lower than those from the normal-filled strip having no glucose. Thus, it may be determined by the second duty cycle of the pulse sequence that the currents obtained are lower than a previously selected value and that the sensor strip is under-filled. For example, for the system of FIG. 15, initial current values less than 0 signify that the sensor strip is under-filled.

In this manner, the gated voltammetric pulse sequences of the present invention allowed for under-fill detection in a two-electrode sensor strip, a function typically requiring a third electrode for conventional sensor systems. Furthermore, the under-fill determination may be made in less than 5 seconds, providing time for the measuring device to signal the user, such as by sending a signal to a light emitting device or a display, to add more sample to the strip.

A common problem for the accuracy of strip based analysis methods is that the reagents, especially the enzyme, degrade over time. One of the effects of enzyme degradation is a change in the calibration values, and thus the precision and/or accuracy of the analysis.

The dynamic current profiles provided by the multiple duty cycles of the present invention may be used to determine the active ionizing agent content of aged sensor strips, where the ionizing species may have degraded. Knowing the amount of ionizing agent available to react with the analyte may allow for the identification of defective sensor strips and for the correction of the analyte concentration value to provide the desired accuracy and precision to the analysis. In this manner, the accuracy and/or precision of the analysis obtained from sensor strips having varying amounts of active ionizing agent due to manufacturing variability or reagent degradation may be obtained.

Figure 16A:
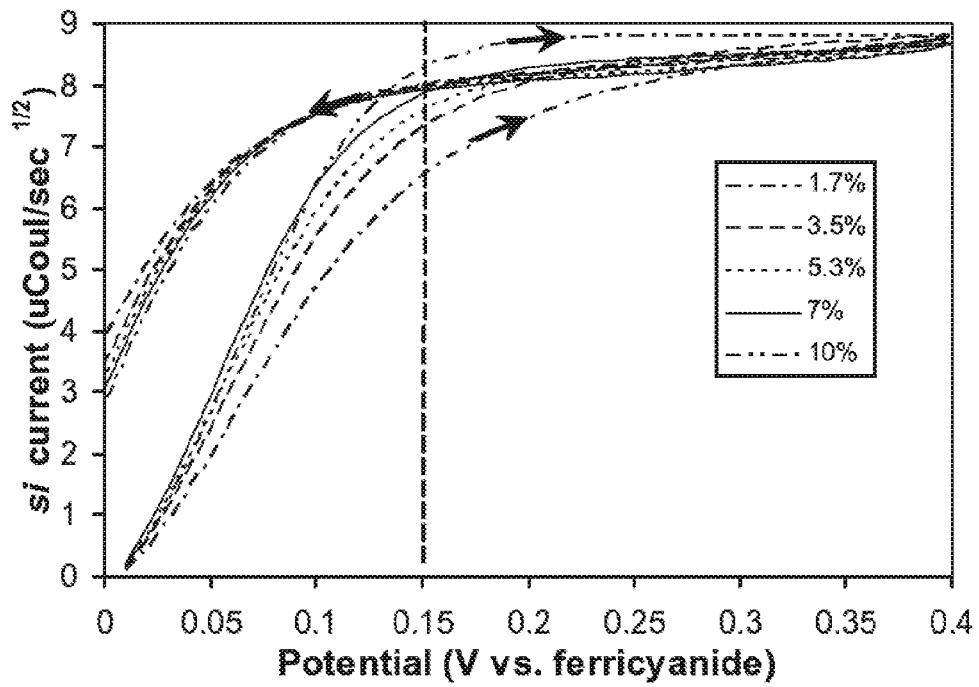
FIG. 16A depicts semi-integral plots of cyclic voltammograms obtained from five sensor strips with 1 V/sec scan rates for a sample including 100 mg/dL glucose and 40% hematocrit in WB.

FIG. 16A depicts semi-integral plots of cyclic voltammograms obtained from five sensor strips with 1 V/sec scan rates for a sample including 100 mg/dL glucose and 40% hematocrit in WB. While FIG. 16A presents acyclic voltammograms, the method also may be applied to cyclic scans. The ionizing agent used in the reagent layer for the sensor strips was the glucose oxidase (GO) enzyme. Each sensor strip included a dry weight percentage of 1.7, 3.5, 5.3, 7, or 10 percent (weight/weight) GO in relation to the total dry weight of the material forming the regent layer. As seen in the figure, the current values for the forward scans increase in relation to those for the reverse scans as the percentage of ionizing agent increases. Thus, the difference between the forward and reverse scan current values may be used to determine the percent of active ionizing agent present in the reagent layer of the sensor strip.

Figure 16B:
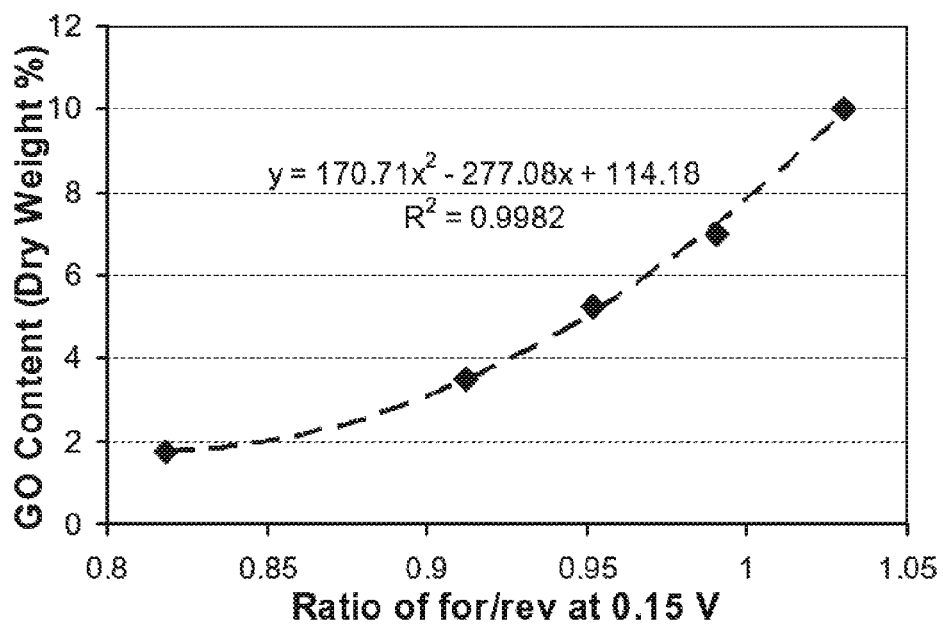
FIG. 16B plots the ratio of the forward and reverse scan current values taken at the 0.15 potential as a function of enzyme concentration.

FIG. 16B plots the ratio of the forward and reverse scan si current values taken at the 0.15 potential as a function of percent GO. Once the correlation between the forward and reverse current ratios and the percent active GO is determined, the amount of active GO present in a reagent layer may be determined from the current values measured for a strip. The ratio of the forward and reverse scans may be determined before or during the analyte analysis portion of the pulse sequence, thus allowing the user to be notified if the strip is defective.

Figure 16C:
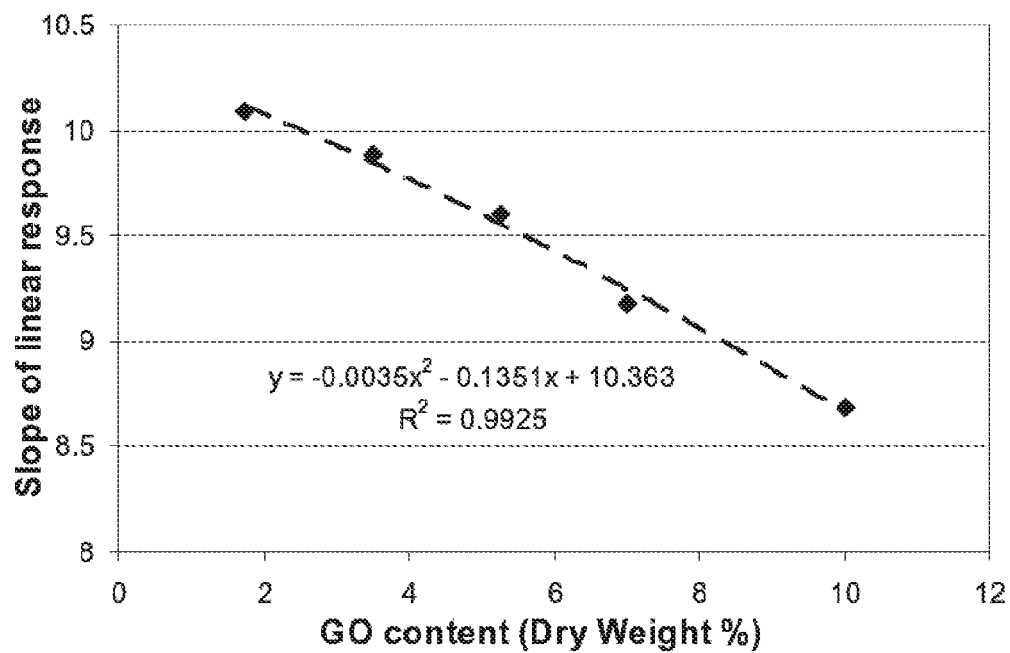
FIG. 16C depicts a typical response of the slope of the linear response calibration of the sensor strip as a function of the GO content (%-dry weight).

The actual active ionizing agent content of the strip may then be used to alter the calibration slope through a relationship such as shown in FIG. 16C. FIG. 16C depicts a typical response of the slope of the linear response calibration of the sensor strip as a function of the GO content (%-dry weight). This plot shows that as the GO content increases, the calibration slope decreases. Thus, if the actual GO content of the reagent layer is calculated from FIG. 16B, the affected slope of the GO-based sensor strip may be calculated from the $2^{nd}$ order polynomial of FIG. 16C using the GO content as the input. The output slope then may be used to correct the glucose concentration value in response to differing amounts of active ionizing agent present in the reagent layer of the sensor strip. In this manner, inaccuracy and/or imprecision that would otherwise result from enzyme degradation may be reduced.

Figure 17:
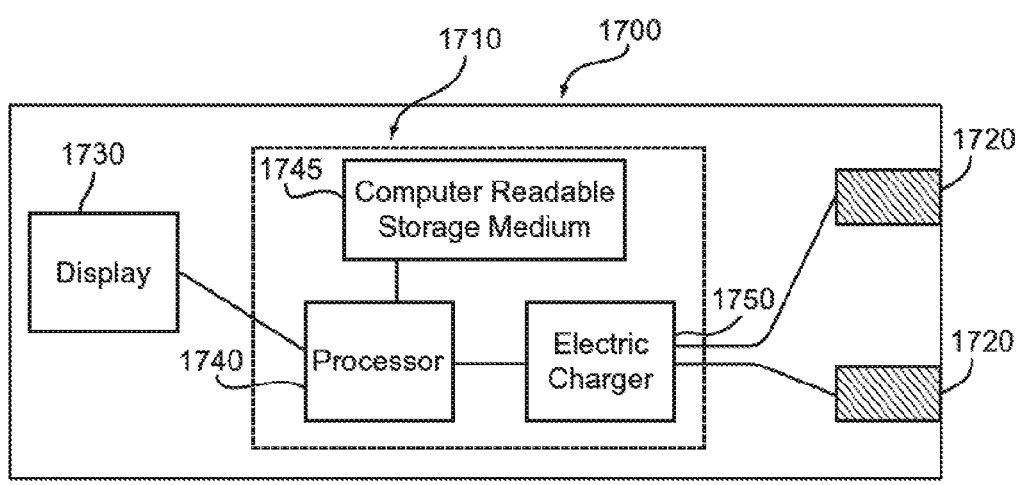
FIG. 17 is a schematic representation of a measuring device.

FIG. 17 is a schematic representation of a measuring device 1700 including contacts 1720 in electrical communication with electrical circuitry 1710 and a display 1730. In one aspect, the measuring device 1700 is portable and is adapted to be handheld and to receive a sensor strip, such as the strip 100 from FIG. 1A. In another aspect, the measuring device 1700 is a handheld measuring device adapted to receive a sensor strip and implement gated voltammetric pulse sequences.

The contacts 1720 are adapted to provide electrical communication with the electrical circuitry 1710 and the contacts of a sensor strip, such as the contacts 170 and 180 of the sensor strip 100 depicted in FIG. 1B. The electrical circuitry 1710 may include an electric charger 1750, a processor 1740, and a computer readable storage medium 1745. The electrical charger 1750 may be a potentiostat, signal generator, or the like. Thus, the charger 1750 may apply a voltage to the contacts 1720 while recording the resulting current to function as a charger-recorder.

The processor 1740 may be in electrical communication with the charger 1750, the computer readable storage medium 1745, and the display 1730. If the charger is not adapted to record current, the processor 1740 may be adapted to record the current at the contacts 1720.

The computer readable storage medium 1745 may be any storage medium, such as magnetic, optical, semiconductor memory, and the like. The computer readable storage medium 1745 may be a fixed memory device or a removable memory device, such as a removable memory card. The display 1730 may be analog or digital, in one aspect a LCD display adapted to displaying a numerical reading.

When the contacts of a sensor strip containing a sample are in electrical communication with the contacts 1720, the processor 1740 may direct the charger 1750 to apply a gated voltammetric pulse sequence to the sample, thus starting the analysis. The processor 1740 may start the analysis in response to the insertion of a sensor strip, the application of a sample to a previously inserted sensor strip, or in response to a user input, for example.

Instructions regarding implementation of the gated voltammetric pulse sequence may be provided by computer readable software code stored in the computer readable storage medium 1745. The code may be object code or any other code describing or controlling the functionality described in this application. The data that results from the gated voltammetric pulse sequence may be subjected to one or more data treatments, including the determination of decay rates, K constants, slopes, intercepts, and/or sample temperature in the processor 1740 and the results, such as a corrected analyte concentration, output to the display 1730. As with the instructions regarding the pulse sequence, the data treatment may be implemented by the processor 1740 from computer readable software code stored in the computer readable storage medium 1745.

EXAMPLES

Example 1

Collection of Voltammetric Data

The cyclic voltammogram of FIG. 7A was obtained from a CH Electrochemical Work Station by applying a potential between the working and counter electrodes of a sensor strip that varied linearly by 1 V/sec at a scan rate of 0.025 V/sec. The current generated at the working electrode during the application of the potential was recorded and plotted as a function of the applied potential. After the initial 0.8 second excitation, the potentiostat opened the circuit to provide a 3.2 second relaxation. Six additional excitations were applied to the strip using the pulse sequence of FIG. 6C. In this manner, seven acyclic voltammograms for glucose concentrations of 0, 50, 100, and 400 mg/dL, as shown in FIGS. 8A-8D, respectively, were obtained.

Example 2

Establishing Contour Plots for Multiple Data Treatments

FIGS. 9A, 9B, and 9C are contour plots from unprocessed voltammetric currents, semi-integral, and semi-derivative data treatments, respectively. In FIG. 9A, unprocessed current values at 0.3 V were taken from each forward scan to provide seven data points. The resulting contour plot presents the unprocessed current values as a function of time since each duty cycle included a 0.8 second excitation followed by a 3.2 second relaxation.

FIG. 9B presents a contour plot of the same voltammetric data converted with semi-integral data processing according to equation (3) and implemented with equations (5) and (6). The implemented semi-integral data processing was that present in the CH Electrochemical Work Station software package, version 4.07, revised Apr. 26, 2004, which accompanies the CH Instruments Electrochemical Workstation, model CHI 660A. After semi-integral processing, the semi-integral currents at 0.3 V were taken from the reverse portion of each scan and plotted as function of time, as previously described with regard to FIG. 9A.

FIG. 9C presents a contour plot of the same voltammetric data converted with semi-derivative data processing according to equation (8). The semi-derivative data processing used was that present in the CH Electrochemical Work Station software package, version 4.07, revised Apr. 26, 2004, which accompanies the CH Instruments Electrochemical Workstation, model CHI 660A. After semi-derivative processing, the peak current value was taken from each scan and plotted as function of time, as previously described with regard to FIGS. 9A and 9B. Thus, the Y-axis of FIG. 9C has the unit of uCoul/sec$^{3/2}$ for the semi-derivative currents.

Example 3

Constructing Calibration Plots and Determining Analyte Concentration

As shown in FIG. 14, a calibration plot for the semi-integral data processing method was formed by taking the semi-integral currents from the four different glucose concentration at 8.8, 12.8, 16.8, and 20.8 seconds from FIG. 9B and plotting the currents as a function of YSI plasma glucose concentration. Glucose sample concentrations were determined from the calibration plot by plugging in the semi-integral processed current from a sample measurement at a specific time into the slope and intercept of the calibration line.

Calibration plots for the unprocessed and semi-derivative processed data were generated similarly. The calibration plots were then used to determine glucose sample concentrations from unprocessed and semi-derivative processed measured current values taken at a specific time.

Example 4

Determining Analyte Concentration from Multiple Calibration Sets

FIG. 4 depicts at least four calibration lines for times up to 20.8 seconds. For an analysis time of 16.8 seconds, the calibration points at 8.8 and 12.8 seconds were used to calibrate the glucose values. The three glucose values calculated from the 8.8, 12.8 and 16.8 second calibration points were the result of independent oxidations separated by the relaxation time before the 8.8, 12.8 and 16.8 second excitation. While representing the same sample glucose concentration, the concentration values differ by the experimental noise. Thus, by averaging, $G=(G_{8.8}+G_{12.8}+G_{16.8})/3$, these values, the signal-to-noise ratio of the final glucose concentration value was increased.

While various embodiments of the invention have been described, it will be apparent to those of ordinary skill in the art that other embodiments and implementations are possible within the scope of the invention.

The invention claimed is:

1. A method of signaling a user to add additional sample to a sensor strip, the sensor strip including at least two electrodes, the method comprising:
    applying a gated voltammetric pulse sequence to the sample through the at least two electrodes of the sensor strip, the pulse sequence having at least two duty cycles,
        wherein each of the at least two duty cycles includes an excitation and a relaxation, and
        wherein the excitations of the at least two duty cycles include a potential varied with time and the relaxations of the at least two duty cycles include a current reduction to at least one-half the current flow at the excitation maxima;
    determining if the sensor strip is under-filled by comparing at least one current value recorded from the gated voltammetric pulse sequence including the at least two duty cycles to a pre-selected value; and
    signaling the user to add additional sample to the sensor strip if the sensor strip is under-filled.

2. The method of claim 1, wherein the determining is performed in less than five seconds.

3. The method of claim 1, wherein the at least one current value is lower than the pre-selected value if the sensor strip is under-filled.

4. The method of claim 1, wherein the pulse sequence comprises at least three duty cycles within 90 seconds or at least three duty cycles within 5 seconds.

5. The method of claim 1, wherein the at least two electrodes are a counter electrode and a working electrode and the working electrode includes a diffusion barrier layer.

6. The method of claim 1, wherein the potential varied with time is varied linearly at a rate of at least 2 mV/sec.

7. The method of claim 6, wherein the excitations are selected from the group consisting of linear, cyclic, acyclic, and combinations thereof.

8. The method of claim 1, wherein the excitations are acyclic and substantially exclude a reverse oxidation peak or a reverse reduction peak of a measurable species responsive to a concentration of an analyte in the sample.

9. The method of claim 1, wherein
the excitations are acyclic and terminate before initiation of a reverse current peak,
the excitations are acyclic and substantially exclude forward and reverse oxidation and reduction peaks of a measurable species responsive to a concentration of an analyte in the sample, or
the excitations are acyclic and are substantially within a diffusion limited current region of a redox pair.

10. A voltammetric method for determining a concentration of an analyte in a sample, the voltammetric method comprising:
applying a pulse sequence to the sample, the pulse sequence comprising at least two duty cycles having excitation/relaxation time ratios from 0.3 to 0.2, wherein each of the at least two duty cycles includes a relaxation, and the relaxations of the at least two duty cycles include a current reduction to at least one-half the current flow at the excitation maxima;
measuring resulting currents from the at least two duty cycles; and
determining the concentration of the analyte in the sample from the resulting currents.

11. The method of claim 10, wherein the concentration of the analyte determined from the voltammetric method is more accurate than a concentration of the analyte in the sample determined from another voltammetric method other than the voltammetric method wherein the excitation/relaxation time ratio of the pulse sequence is greater than 0.3.

12. The method of claim 10, wherein the determining is performed in less than five seconds.

13. The method of claim 10, wherein the pulse sequence comprises at least three duty cycles within 90 seconds or at least three duty cycles within 5 seconds.

14. The method of claim 10, wherein each of the at least two duty cycles includes an excitation, and wherein the excitations comprise a potential varied linearly at a rate of at least 2 mV/sec.

15. The method of claim 14, wherein the excitations are selected from the group consisting of linear, cyclic, acyclic, and combinations thereof.

16. The method of claim 10, wherein each of the at least two duty cycles includes an excitation, and wherein the excitations are acyclic and substantially exclude a reverse oxidation peak or a reverse reduction peak of a measurable species responsive to the concentration of the analyte in the sample.

17. The method of claim 10, wherein each of the at least two duty cycles includes an excitation, and wherein
the excitations are acyclic and terminate before initiation of a reverse current peak,
the excitations are acyclic and substantially exclude forward and reverse oxidation and reduction peaks of a measurable species responsive to the concentration of the analyte in the sample, or
the excitations are acyclic and are substantially within a diffusion limited current region of a redox pair.

18. A voltammetric method for determining a hematocrit concentration of a blood sample, the voltammetric method comprising:
applying a gated voltammetric pulse sequence to the blood sample, the pulse sequence having at least two duty cycles,
wherein each of the at least two duty cycles includes an excitation and a relaxation, and
wherein the excitations of the at least two duty cycles include a potential varied with time and the relaxations of the at least two duty cycles include a current reduction to at least one-half the current flow at the excitation maxima;
measuring resulting currents from at least one of the excitations;
applying a semi-integral data treatment to the resulting currents, the semi-integral data treatment providing a peak portion; and
quantitatively relating the peak portion to the hematocrit concentration of the blood sample.

19. The method of claim 18, wherein the excitations are acyclic and substantially exclude a reverse oxidation peak or a reverse reduction peak of a measurable species responsive to a concentration of an analyte in the blood sample.

20. The method of claim 18, wherein
the excitations are acyclic and terminate before initiation of a reverse current peak,
the excitations are acyclic and substantially exclude forward and reverse oxidation and reduction peaks of a measurable species responsive to a concentration of an analyte in the sample, or
the excitations are acyclic and are substantially within a diffusion limited current region of a redox pair.

21. A voltammetric method for determining a percent hematocrit of a blood sample, the voltammetric method comprising:
applying a gated voltammetric pulse sequence to the blood sample, the pulse sequence having at least two duty cycles,
wherein each of the at least two duty cycles includes an excitation and a relaxation, and
wherein the excitations of the at least two duty cycles include a potential varied with time and the relaxations of the at least two duty cycles include a current reduction to at least one-half the current flow at the excitation maxima;
measuring resulting currents from at least one of the excitations;
applying a derivative data treatment to the resulting currents, the derivative data treatment providing a negative derivative peak and a positive derivative peak;
determining a ratio of the negative derivative peak to the positive derivative peak; and
quantitatively relating the ratio to the percent hematocrit in the blood sample.

22. The method of claim 21, wherein the excitations are acyclic and substantially exclude a reverse oxidation peak or a reverse reduction peak of a measurable species responsive to a concentration of an analyte in the blood sample.

23. The method of claim 21, wherein
the excitations are acyclic and terminate before initiation of a reverse current peak,
the excitations are acyclic and substantially exclude forward and reverse oxidation and reduction peaks of a measurable species responsive to a concentration of an analyte in the sample, or
the excitations are acyclic and are substantially within a diffusion limited current region of a redox pair.

24. A method of determining an amount of active ionizing agent available to react with an analyte, the method comprising:
applying a gated voltammetric pulse sequence to a sample in a sensor strip through at least two electrodes, the pulse sequence having at least two duty cycles, the sample including an analyte and active ionizing agent,
wherein each of the at least two duty cycles includes an excitation and a relaxation,
wherein the excitations of the at least two duty cycles include a potential varied with time and the excitations include forward and reverse scans, and
wherein the relaxations of the at least two duty cycles include a current reduction to at least one-half the current flow at the excitation maxima;
measuring resulting currents from the forward and the reverse scans of at least one of the excitations;
determining a ratio of the resulting currents from the forward and the reverse scans;
comparing the determined ratio to a previously determined correlation ratio and a percent active ionizing agent; and
determining the amount of the active ionizing agent available to react with the analyte.

25. The method of claim 24, further comprising altering a calibration slope relating output current values to a concentration of the analyte in the sample with the determined amount of the active ionizing agent available to react with the analyte.

26. The method of claim 25, wherein the analyte concentration of the sample is determined from the altered calibration slope.

27. The method of claim 24, wherein the excitations are acyclic and substantially exclude a reverse oxidation peak or a reverse reduction peak of a measurable species responsive to a concentration of the analyte in the sample.

28. The method of claim 24, wherein
the excitations are acyclic and terminate before initiation of a reverse current peak,
the excitations are acyclic and substantially exclude forward and reverse oxidation and reduction peaks of a measurable species responsive to a concentration of an analyte in the sample, or
the excitations are acyclic and are substantially within a diffusion limited current region of a redox pair.

29. A voltammetric method for determining a concentration of an analyte in a sample, the voltammetric method comprising:
applying a pulse sequence to the sample, the pulse sequence comprising at least two duty cycles having excitation/relaxation time ratios from 0.3 to 0.2, wherein each of the at least two duty cycles includes an excitation, and wherein the excitations comprise a potential varied linearly at a rate of at least 2 mV/sec;
measuring resulting currents from the at least two duty cycles; and
determining the concentration of the analyte in the sample from the resulting currents.

30. A voltammetric method for determining a concentration of an analyte in a sample, the voltammetric method comprising:
applying a pulse sequence to the sample, the pulse sequence comprising at least two duty cycles having excitation/relaxation time ratios from 0.3 to 0.2, wherein each of the at least two duty cycles includes an excitation, and wherein the excitations are acyclic and substantially exclude a reverse oxidation peak or a reverse reduction peak of a measurable species responsive to the concentration of the analyte in the sample;
measuring resulting currents from the at least two duty cycles; and
determining the concentration of the analyte in the sample from the resulting currents.

31. A voltammetric method for determining a concentration of an analyte in a sample, the voltammetric method comprising:
applying a pulse sequence to the sample, the pulse sequence comprising at least two duty cycles having excitation/relaxation time ratios from 0.3 to 0.2, wherein each of the at least two duty cycles includes an excitation;
measuring resulting currents from the at least two duty cycles; and
determining the concentration of the analyte in the sample from the resulting currents, wherein
the excitations are acyclic and terminate before initiation of a reverse current peak,
the excitations are acyclic and substantially exclude forward and reverse oxidation and reduction peaks of a measurable species responsive to the concentration of the analyte in the sample, or
the excitations are acyclic and are substantially within a diffusion limited current region of a redox pair.

* * * * *

UNITED STATES PATENT AND TRADEMARK OFFICE
CERTIFICATE OF CORRECTION

PATENT NO. : 9,110,013 B2
APPLICATION NO. : 14/136286
DATED : August 18, 2015
INVENTOR(S) : Huan-Ping Wu It is certified that error appears in the above-identified patent and that said Letters Patent is hereby corrected as shown below:

ON THE TITLE PAGE

In Column 1, below "Related U.S. Application Data", Line 1 delete item "(60)" and insert item -- (62) --, therefor.

In Item (56), under "OTHER PUBLICATIONS", in Column 2, Line 1, delete "Opionion" and insert -- Opinion --, therefor.

On Page 7, in Item (56), under "OTHER PUBLICATIONS", in Column 2, Line 4, delete "accurancy and Percision" and insert -- Accuracy and Precision --, therefor.

On Page 7, in Item (56), under "OTHER PUBLICATIONS", in Column 2, Line 6, delete "Low-Potenetail" and insert -- Low-Potential --, therefor.

IN THE SPECIFICATION

In Column 1, Line 6, delete "2013," and insert -- 2013, now Pat. No. 8,647,489, --, therefor.

In Column 1, Line 8, delete "2008," and insert -- 2008, now Pat. No. 8,404,100, --, therefor.

In Column 9, Line 22, delete "+5%." and insert -- ± 5%. --, therefor.

In Column 11, Line 5, delete "shows" and insert -- show --, therefor.

In Column 11, Line 8, delete "glucose" and insert -- glucose. --, therefor.

In Column 14, Line 66, delete "reagent layer 175" and insert -- reagent layer 275 --, therefor.

In Column 15, Line 14, delete "DBUreagent" and insert -- DBL/reagent --, therefor.

Signed and Sealed this
Twenty-ninth Day of March, 2016

Michelle K. Lee
*Director of the United States Patent and Trademark Office*

CERTIFICATE OF CORRECTION (continued)
U.S. Pat. No. 9,110,013 B2

IN THE SPECIFICATION

In Column 15, Line 17, delete "DBUreagent" and insert -- DBL/reagent --, therefor.

In Column 15, Line 19, delete "DBUreagent" and insert -- DBL/reagent --, therefor.

In Column 15, Line 36, delete "DBUreagent" and insert -- DBL/reagent --, therefor.

In Column 16, Line 5, delete "DBL 320," and insert -- DBL 305, --, therefor.

In Column 16, Line 10, delete "sensor strip 300" and insert -- sensor strip --, therefor.

In Column 21, Line 30, delete "Joul/(mole*K)," and insert -- Joule/(mole*K), --, therefor.

In Column 27, Line 66, delete "as 150" and insert -- as ≤ 150 --, therefor.

In Column 28, Line 18, delete "1/√3)." and insert -- 1/√3. --, therefor.

In Column 30, Line 25, delete "contacts 170" and insert -- conductors 170 --, therefor.

In Column 31, Line 55, delete "uCoul/sec3/2" and insert -- μCoul/sec3/2 --, therefor.